(12) United States Patent
Lam et al.

(10) Patent No.: US 11,192,978 B2
(45) Date of Patent: Dec. 7, 2021

(54) REVERSIBLY CROSSLINKED MICELLE SYSTEMS

(71) Applicant: The Regents of the University of California, Oakland, CA (US)

(72) Inventors: Kit S. Lam, Davis, CA (US); Yuanpei Li, Davis, CA (US); Juntao Luo, Jamesville, NY (US); Kai Xiao, Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 87 days.

(21) Appl. No.: 16/131,644

(22) Filed: Sep. 14, 2018

(65) Prior Publication Data

US 2019/0112423 A1    Apr. 18, 2019

Related U.S. Application Data

(63) Continuation of application No. 14/117,570, filed as application No. PCT/US2012/037994 on May 14, 2012, now Pat. No. 10,106,650.

(60) Provisional application No. 61/487,953, filed on May 19, 2011, provisional application No. 61/485,774, filed on May 13, 2011.

(51) Int. Cl.
| | |
|---|---|
| *A61K 47/60* | (2017.01) |
| *C08G 83/00* | (2006.01) |
| *A61K 47/28* | (2006.01) |
| *C08G 65/334* | (2006.01) |
| *C08G 65/329* | (2006.01) |
| *C08L 71/02* | (2006.01) |
| *A61K 9/107* | (2006.01) |
| *A61K 45/06* | (2006.01) |
| *A61K 47/34* | (2017.01) |
| *A61K 31/337* | (2006.01) |
| *A61K 9/127* | (2006.01) |

(52) U.S. Cl.
CPC ........ *C08G 65/3348* (2013.01); *A61K 9/1075* (2013.01); *A61K 31/337* (2013.01); *A61K 45/06* (2013.01); *A61K 47/28* (2013.01); *A61K 47/34* (2013.01); *A61K 47/60* (2017.08); *C08G 65/329* (2013.01); *C08G 83/004* (2013.01); *C08L 71/02* (2013.01); *A61K 9/1271* (2013.01); *Y10T 428/2982* (2015.01)

(58) Field of Classification Search
CPC .... C08G 65/337; C08G 83/004; A61K 47/60; A61K 47/28
See application file for complete search history.

(56) References Cited

U.S. PATENT DOCUMENTS

| | | |
|---|---|---|
| 2006/0127310 A1 | 6/2006 | Gregory et al. |
| 2008/0188399 A1 | 8/2008 | Sinko et al. |

FOREIGN PATENT DOCUMENTS

| | | |
|---|---|---|
| EP | 1230934 A1 | 8/2002 |
| EP | 2087912 A1 | 8/2009 |
| JP | 2001146556 A | 5/2001 |
| JP | 2012503603 A | 2/2012 |
| WO | 2008062909 A1 | 5/2008 |
| WO | 2010039496 A2 | 4/2010 |
| WO | 2010148346 A2 | 12/2010 |
| WO | 2012158622 A2 | 11/2012 |

OTHER PUBLICATIONS

Li et al.; "Well-Defined, Reversible Boronate Crosslinked Nanocarriers for Targeted Drug Delivery in Response to Acidic pH Values"; 2012; Angew. Chem. Int. Ed.; 51:2864-2869 DOI: 10.1002/anie.201107144 (Year: 2012).*
European Search Report for European Application No. EP 12 78 6464 dated Oct. 29, 2014, 7 pages.
Heffernan, et al., "Disulfide-Crosslinked Polyion Micelles for Delivery of Protein Therapeutics", Annals of Biomedical Engineering, vol. 37, No. 10, pp. 1993-2002 (Jun. 2009).
International Search Report and Written Opinion for PCT/US2012/037794, 8 pages, dated Jan. 28, 2013.
Li, et al., "Well-defined, reversible disulfide cross-linked micelles for on-demand paclitaxel delivery," Biomaterials, vol. 32(27), pp. 6633-6645 (2011).
Li, et al., "Well-Defined, Reversible Boronate Crosslinked Nanocarriers for Targeted Drug Delivery in Response to Acidic pH Values and cis-Diols," Angewandte Chemie, vol. 124(12), pp. 2918-2923 (2012).

* cited by examiner

*Primary Examiner* — Timothy P Thomas
(74) *Attorney, Agent, or Firm* — Mintz Levin Cohn Ferris Glovsky and Popeo, P.C.

(57) ABSTRACT

The present invention provides amphiphilic telodendrimers that aggregate to form nanocarriers characterized by a hydrophobic core and a hydrophilic exterior. The nanocarrier core may include amphiphilic functionality such as cholic acid or cholic acid derivatives, and the exterior may include branched or linear poly(ethylene glycol) segments. Nanocarrier cargo such as hydrophobic drugs and other materials may be sequester in the core via non-covalent means or may be covalently bound to the telodendrimer building blocks. Telodendrimer structure may be tailored to alter loading properties, interactions with materials such as biological membranes, and other characteristics.

1 Claim, 40 Drawing Sheets

SCALE BARS = 100 nm

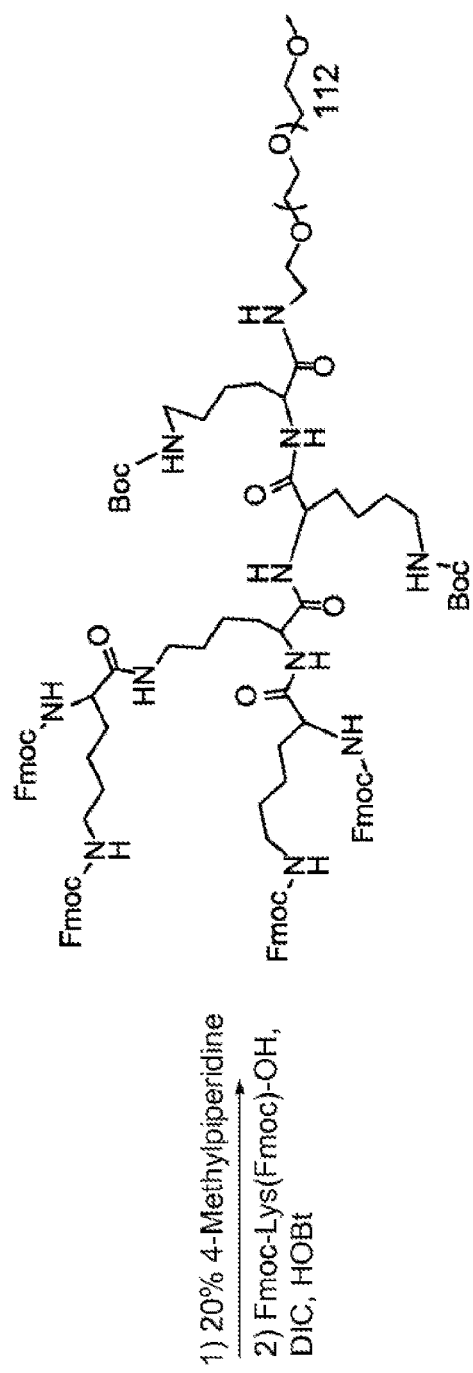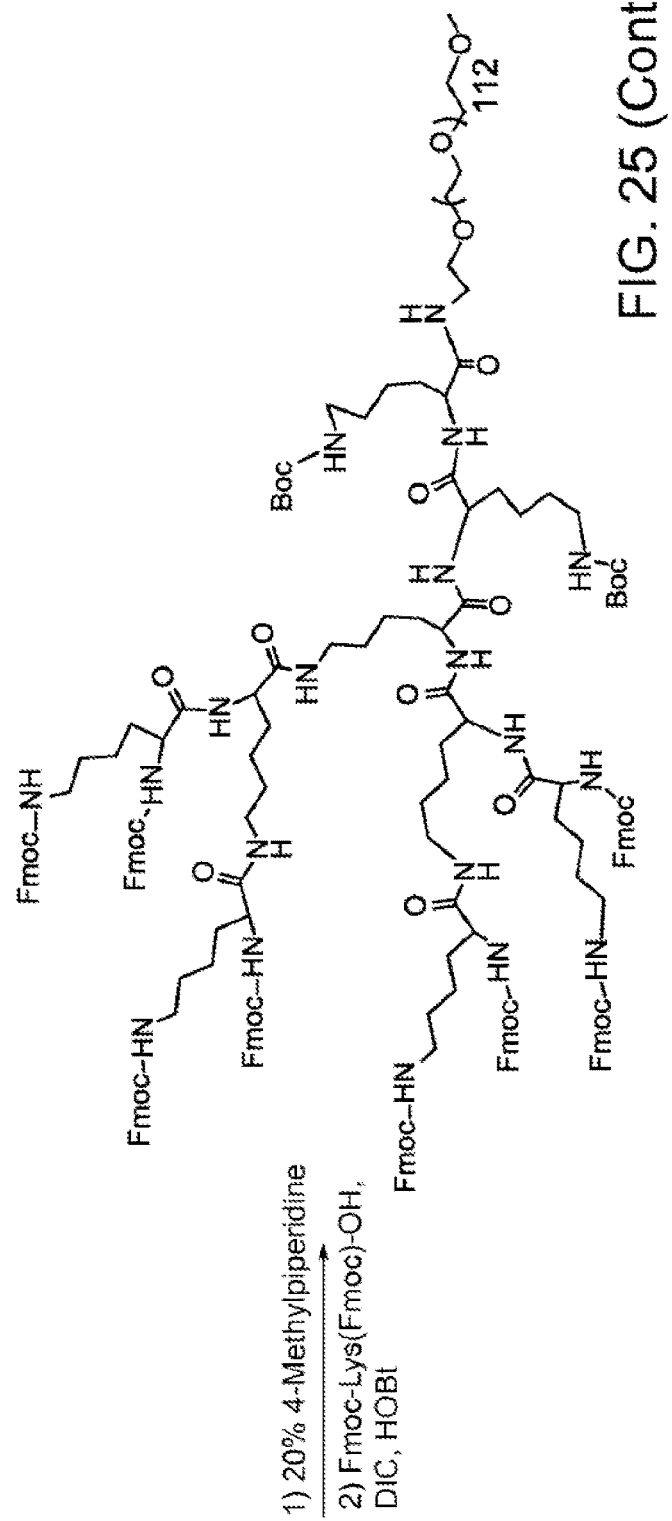
FIG. 25 (Cont. 1)

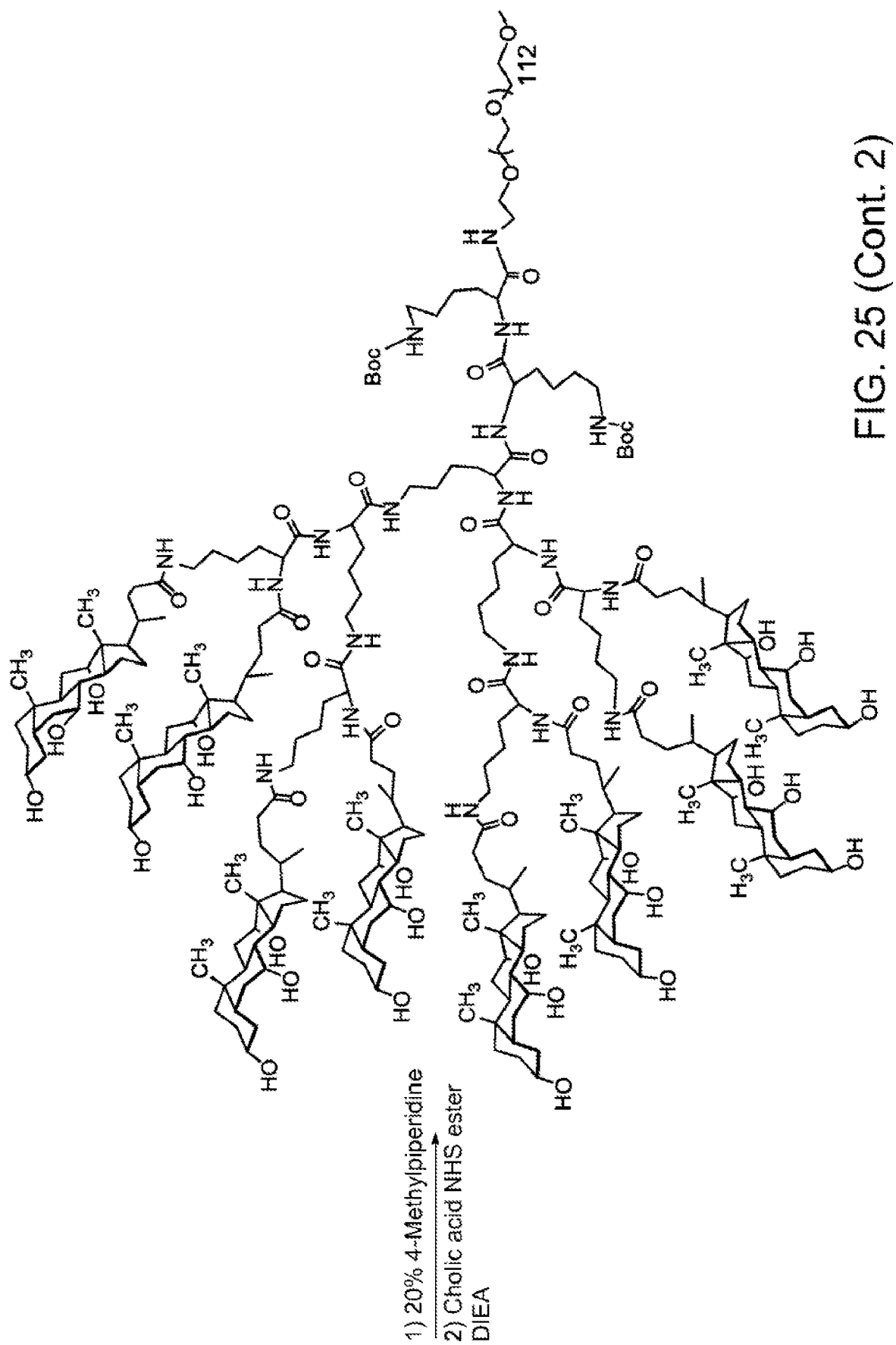
FIG. 25 (Cont. 2)

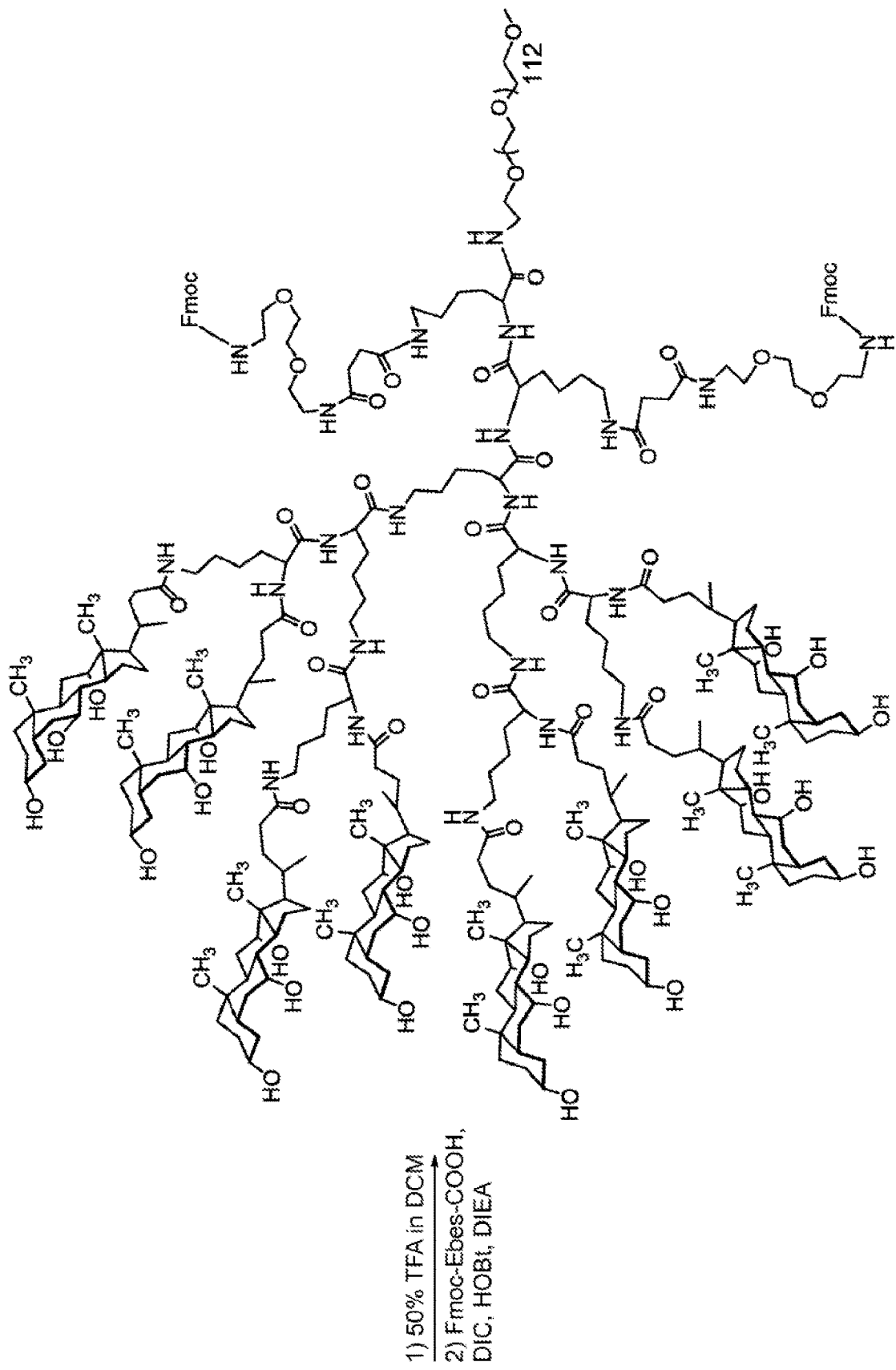
FIG. 25 (Cont. 3)

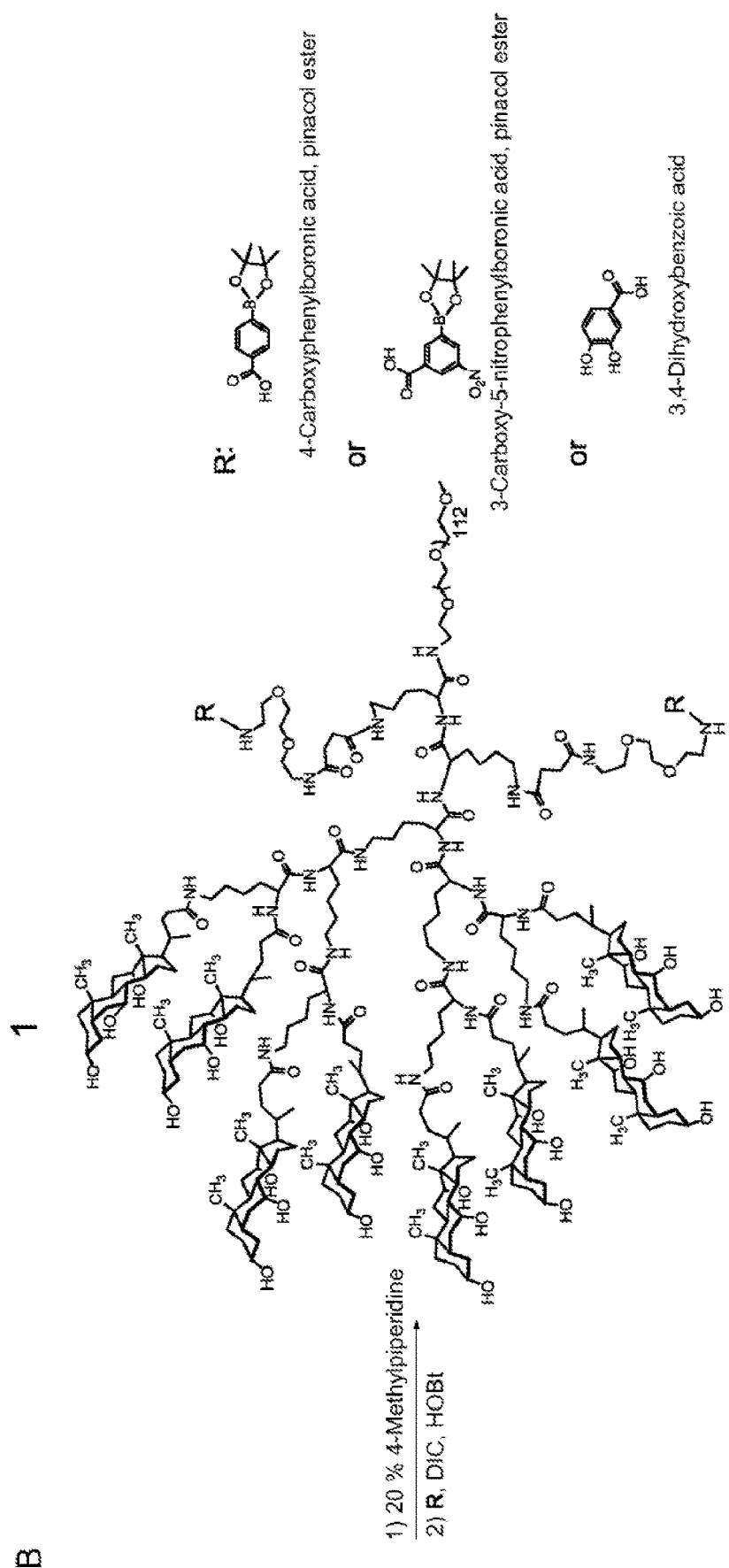
FIG. 25 (Cont. 4)

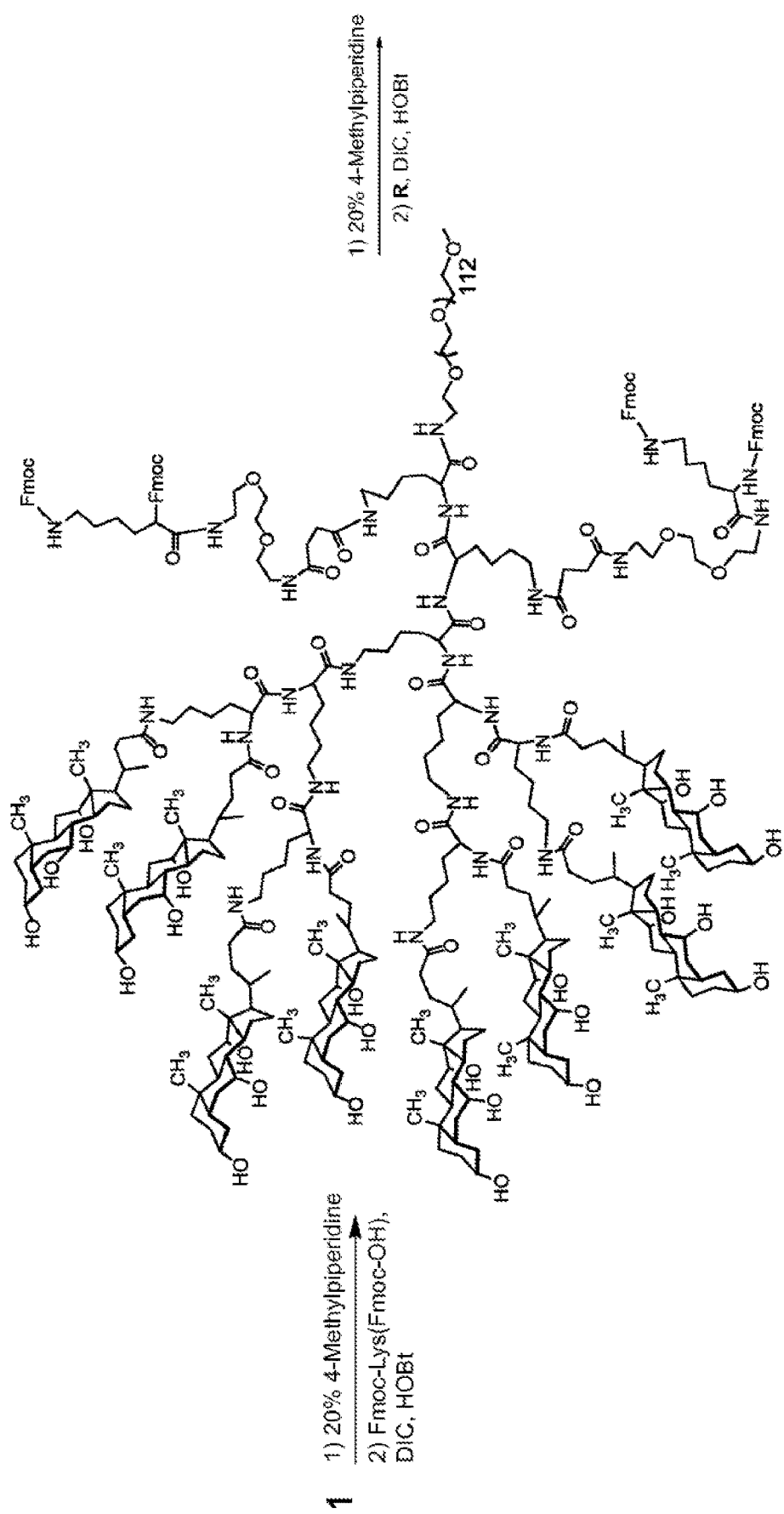
FIG. 25 (Cont. 5)

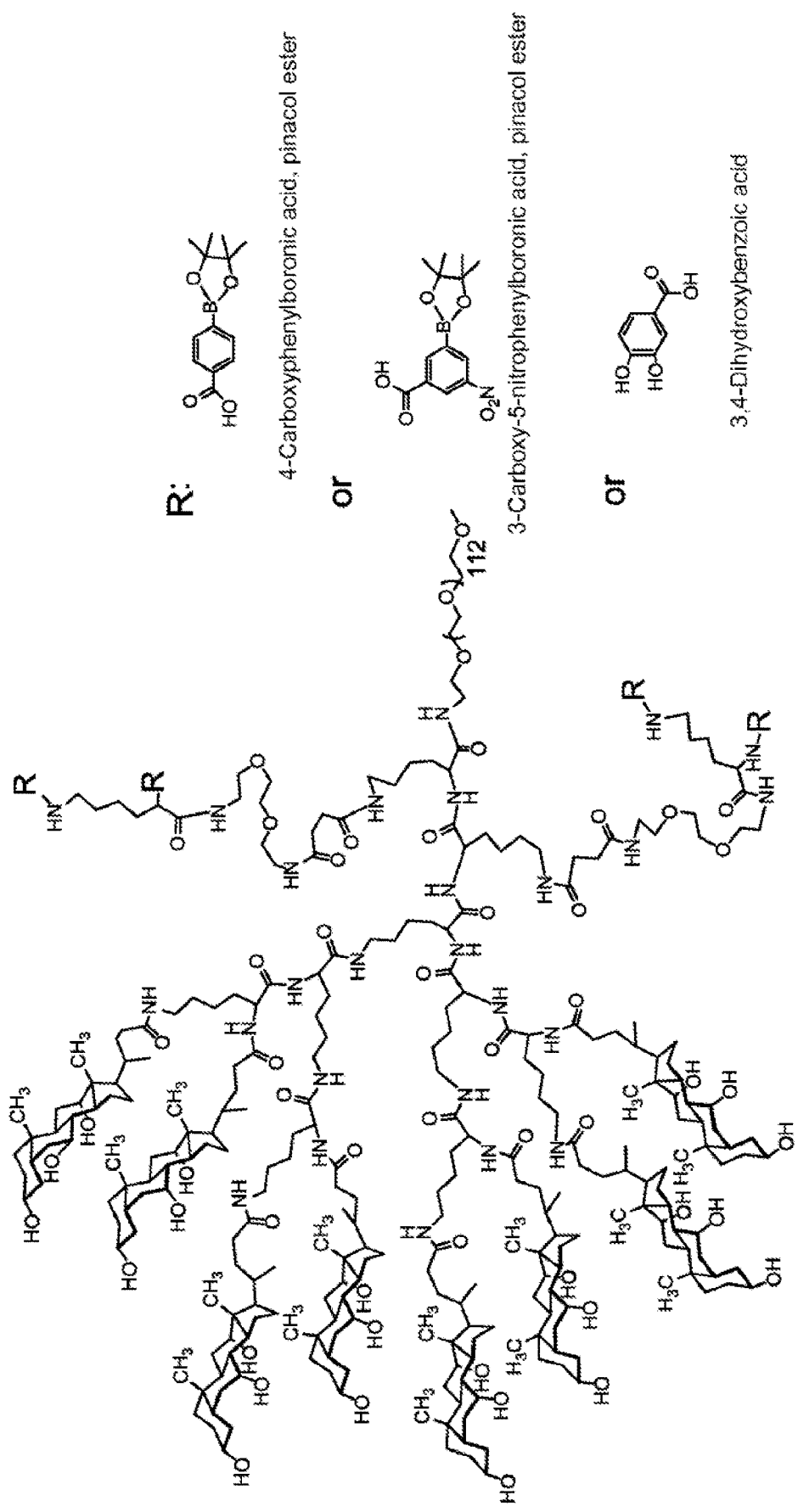
FIG. 25 (Cont. 6)

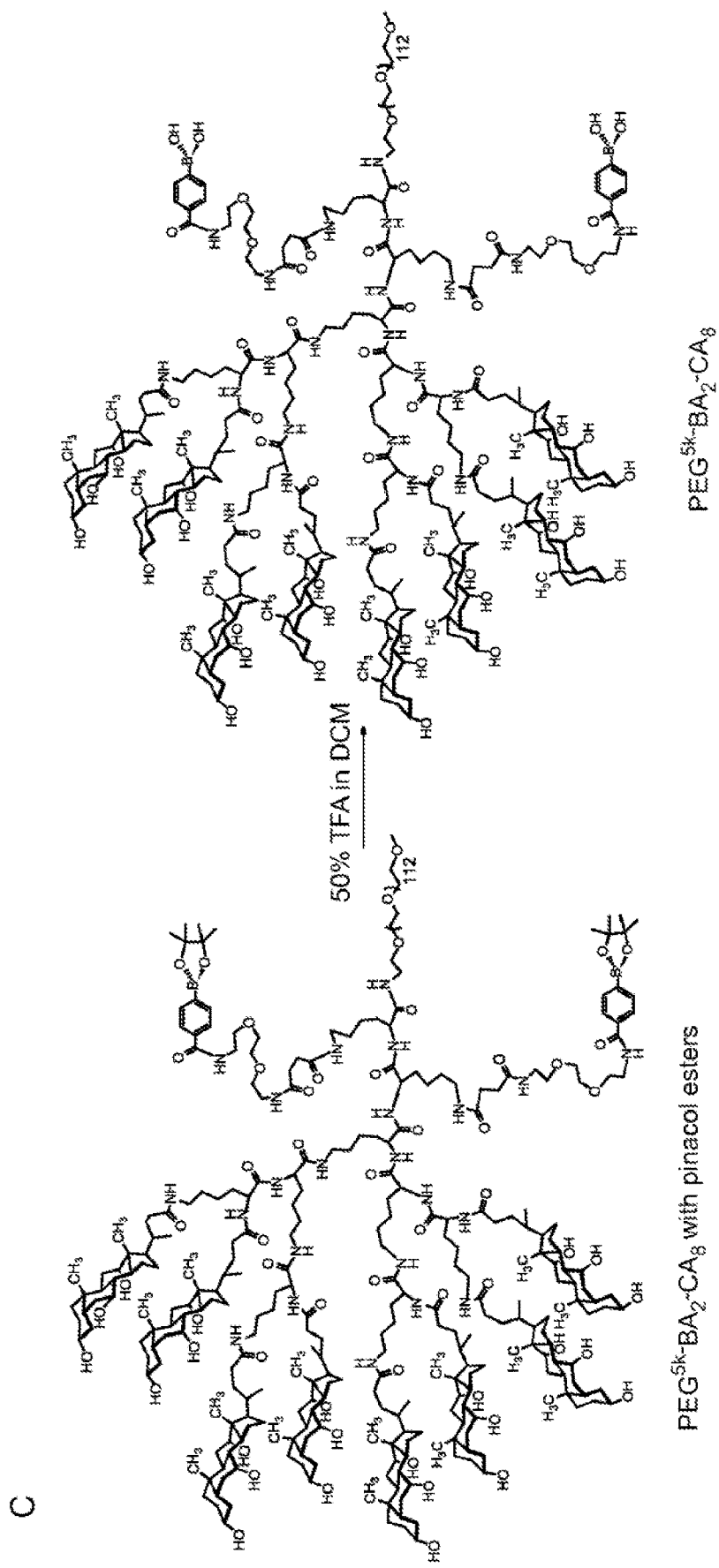
FIG. 25 (Cont. 7)

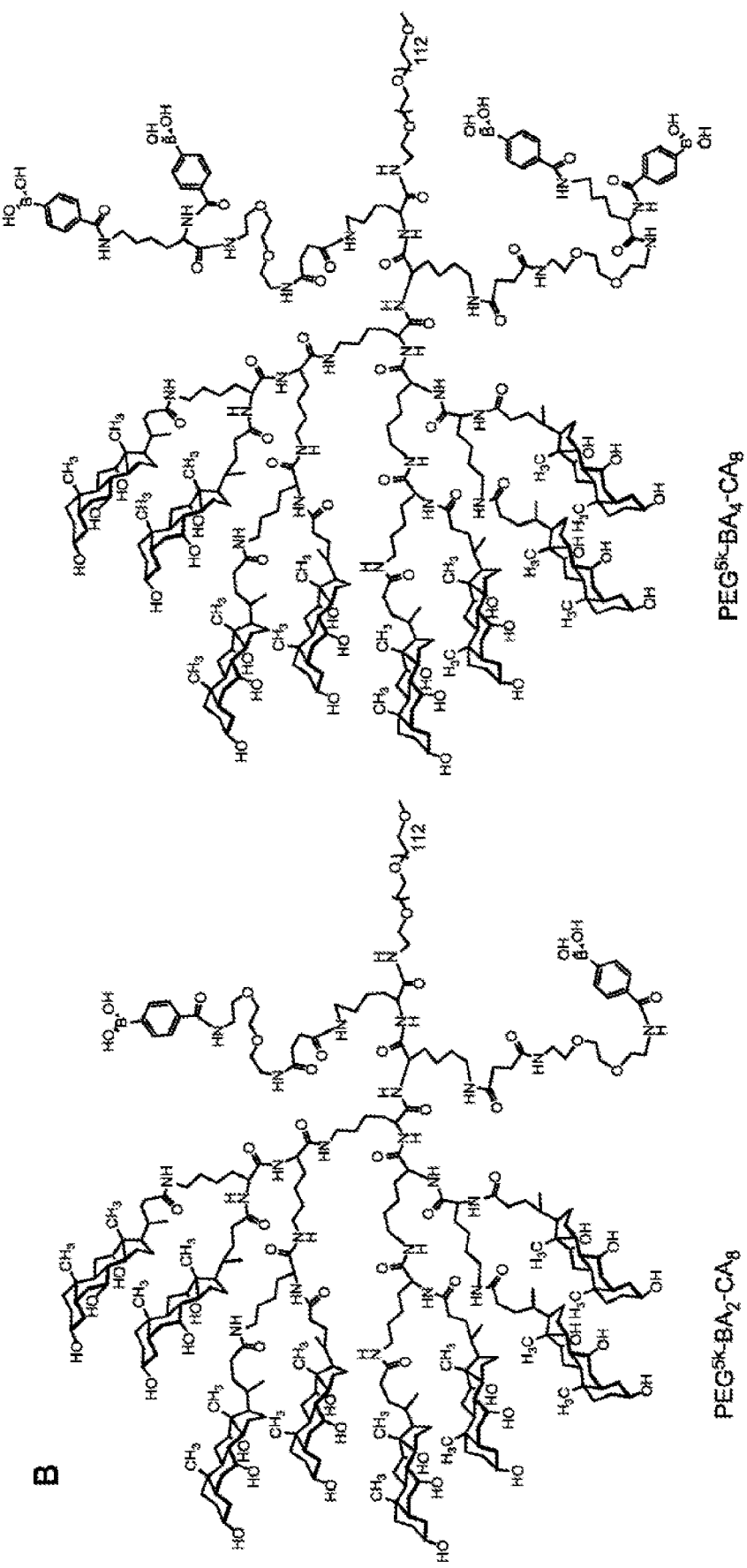
FIG. 26 (Cont. 1)

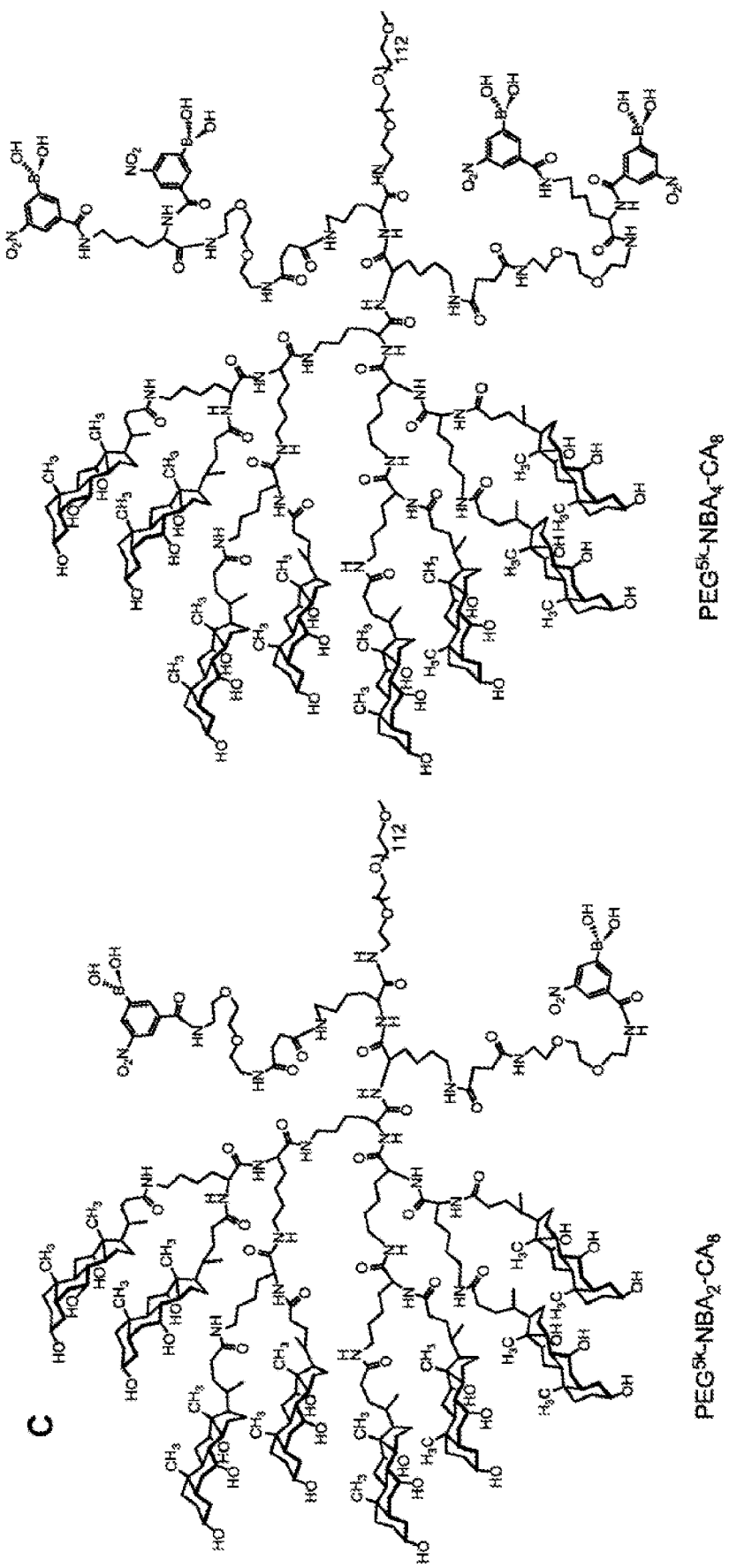
FIG. 26 (Cont. 2)

REVERSIBLY CROSSLINKED MICELLE SYSTEMS

CROSS-REFERENCES TO RELATED APPLICATIONS

This application claims priority to U.S. Provisional Application Nos. 61/485,774, filed May 13, 2011, and 61/487,953, filed May 19, 2011, which are incorporated in their entirety herein for all purposes.

STATEMENT AS TO RIGHTS TO INVENTIONS MADE UNDER FEDERALLY SPONSORED RESEARCH AND DEVELOPMENT

This invention was made with Government support under Grant Nos. CA115483 and CA140449 awarded by the National Institutes of Health. The Government has certain rights in this invention.

BACKGROUND OF THE INVENTION

Several effective chemotherapeutic agents for treatment of various cancer types are very insoluble in water, requiring formulations that induce unwanted side effects. Recently, nanotherapeutic formulations such as Abraxane® (paclitaxel-loaded albumin nanoparticles), Doxil® (doxorubicin-loaded liposomes), and others have been shown to improve the clinical toxicity profiles of the drugs, but their anti-tumor effects are only marginally better than the original drug formulations. This has been attributed in part to the relatively large size of the nanotherapeutic formulations (generally >100 nm), which limits the extent to which the drugs can penetrate into tumor mass. In some cases, this large size also causes nanotherapeutics to be trapped in the liver and reticuloendothelial system (RES). Accordingly, there is a need to develop smaller (20-80 nm) stealth and biocompatible nanocarriers for effective delivery anti-cancer drugs in vivo.

We have recently developed several novel nanocarriers for paclitaxel (PTX) or other hydrophobic drugs. These novel nanocarriers, comprising poly(ethylene glycol) (PEG) and oligo-cholic acids, can self-assemble under aqueous conditions to form core-shell (cholane-PEG) structures that can carry PTX in the hydrophobic interior. These amphiphilic drug-loaded nanoparticles are therapeutic by themselves with improved clinical toxicity profiles. More importantly, when decorated with cancer cell surface targeting ligands and/or tumor blood vessel ligands, these nanocarriers will be able to deliver toxic therapeutic agents to the tumor sites. The final size of the nanocarriers (10 to 100 nm) is tunable by using various, or a combination of, different cholane-PEG preparations. The nanocarrier components, PEG and cholic acid, are all biocompatible and largely non-toxic. Indeed, the PTX nanotherapeutics exhibited safe profile in in vivo administration for anticancer treatment in mouse models and companion dogs. However, some nanocarriers exhibited some hemolytic activity both in vitro and in vivo, as well as reduced stability and loading capacity for certain drugs. Therefore, there is a need to develop nanocarriers with improved stability, biocompatibility and versatility.

The present invention is based on the surprising discovery that certain crosslinkable functional groups can be introduced into telodendrimers, therefore crosslinking the nanoparticles reversibly to minimize premature drug release and increase in vitro and in vivo stability of the nanotherapeutics. The crosslinked nanotherapeutics improve the therapeutic properties without disrupting nanocarrier assembly and drug loading capacity and stability, therefore addressing the needs described above.

BRIEF SUMMARY OF THE INVENTION

In some embodiments, the invention provide a compound of formula I:

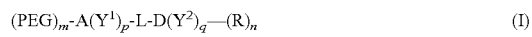

$$(PEG)_m\text{-}A(Y^1)_p\text{-}L\text{-}D(Y^2)_q\text{---}(R)_n \qquad (I)$$

wherein radical A of formula I is linked to at least one PEG group. Radical D of formula I is a dendritic polymer having a single focal point group, a plurality of branched monomer units X and a plurality of end groups. Radical L of formula I is a bond or a linker linked to the focal point group of the dendritic polymer. Each PEG of formula I is a polyethyleneglycol (PEG) polymer, wherein each PEG polymer has a molecular weight of 1-100 kDa. Each R of formula I can be the end group of the dendritic polymer, a hydrophobic group, a hydrophilic group, an amphiphilic compound or a drug, such that when R is not an end group then each R is linked to one of the end groups. Each $Y^1$ and $Y^2$ of formula I is a crosslinkable group that can be any of boronic acid, dihydroxybenzene or a thiol. Subscript m of formula I is an integer from 0 to 20. Subscript n of formula I is an integer from 2 to 20, wherein subscript n is equal to the number of end groups on the dendritic polymer, and wherein at least half the number n of R groups that can each be a hydrophobic group, a hydrophilic group, an amphiphilic compound or a drug. And, each of subscripts p and q are 0 or from 2 to 8, such that one of subscripts p and q is from 2 to 8.

In some embodiments, the invention provides a nanocarrier having an interior and an exterior, the nanocarrier including at least two conjugates, wherein each conjugate includes a polyethylene glycol (PEG) polymer, at least two amphiphilic compounds having both a hydrophilic face and a hydrophobic face, at least two crosslinking groups, and a dendritic polymer covalently attached to the PEG, the amphiphilic compounds and the crosslinking groups, wherein each conjugate self-assembles in an aqueous solvent to form the nanocarrier such that a hydrophobic pocket is formed in the interior of the nanocarrier, wherein the PEG of each compound self-assembles on the exterior of the nanocarrier, and wherein at least two conjugates are reversibly crosslinked via the crosslinking groups.

In some embodiments, the present invention provides a method of reversing the cross-linking of the reversibly crosslinked nanocarrier of the present invention, by contacting the reversibly crosslinked nanocarrier with a bond cleavage component suitable for cleaving the cross-linked bond, thereby reversing the cross-linking of the reversibly crosslinked nanocarrier.

In some embodiments, the present invention provides a method of treating a disease, including administering to a subject in need of such treatment, a therapeutically effective amount of a nanocarrier of the present invention, wherein the nanocarrier includes a drug. The drug can be a covalently attached to a conjugate of the nanocarrier.

In some embodiments, the present invention provides a method of delivering a drug to a subject in need thereof by administering a nanocarrier of the present invention to the subject, wherein the nanocarrier includes the drug and a plurality of cross-linked bonds. The method also includes cleaving the cross-linked bonds using a bond cleavage component, such that the drug is released from the nanocarrier, thereby delivering the drug to the subject.

In some embodiments, the present invention provides a method of imaging, including administering to a subject to be imaged, an effective amount of a nanocarrier of the present invention, wherein the nanocarrier includes an imaging agent.

$CA_8$ (0.1 mM) with different ratios of $PEG^{5k}$-Catechol$_4$-$CA_8$ (0-0.5 mM) in PBS at pH7.4. Excitation: 468 nm. (B) Continuous dynamic light scattering measurements of NCM in SDS and BCM4 in SDS for 120 min, at which time mannitol was added or pH of the solution was adjusted to 5.0 (see arrow). TEM images of BCM4 in PBS(C1), BCM4 in SDS for 120 min (C2), BCM4 in SDS for 120 mM and then adjusted the pH of the solution to 5.0 for 20 min (C3), and BCM4 in SDS for 120 mM and then treated with mannitol (100 mM) for 20 min (C4), (scale bar: 100 nm).

Figure 23:
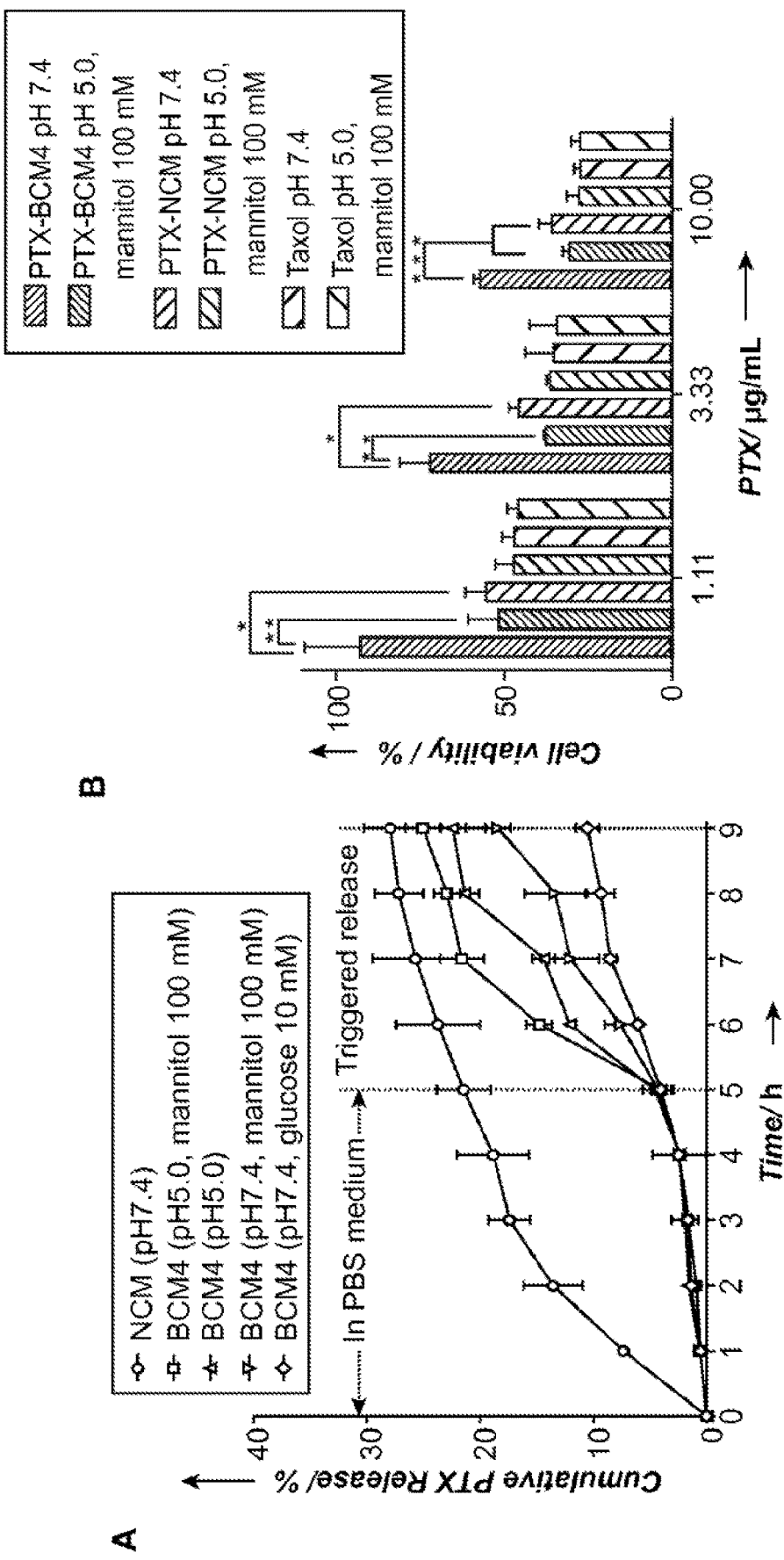

FIG. 23 shows (A) pH- and diol-responsive paclitaxel (PTX) release profiles of BCM4 by treating with diols (mannitiol and glucose) and/or pH 5.0 at 5 hr compared with that of NCM. (B) MTT assays showing the viability of SKOV-3 cells after 1 hr incubation with Taxol®, PTX-NCM and PTX-BCM4 with or without treatment with 100 mM mannitol at pH5.0, followed by 3 times wash with PBS and additional 23 hr incubation. *: p<0.05, : p<0.01, *: p<0.001.

Figure 24:
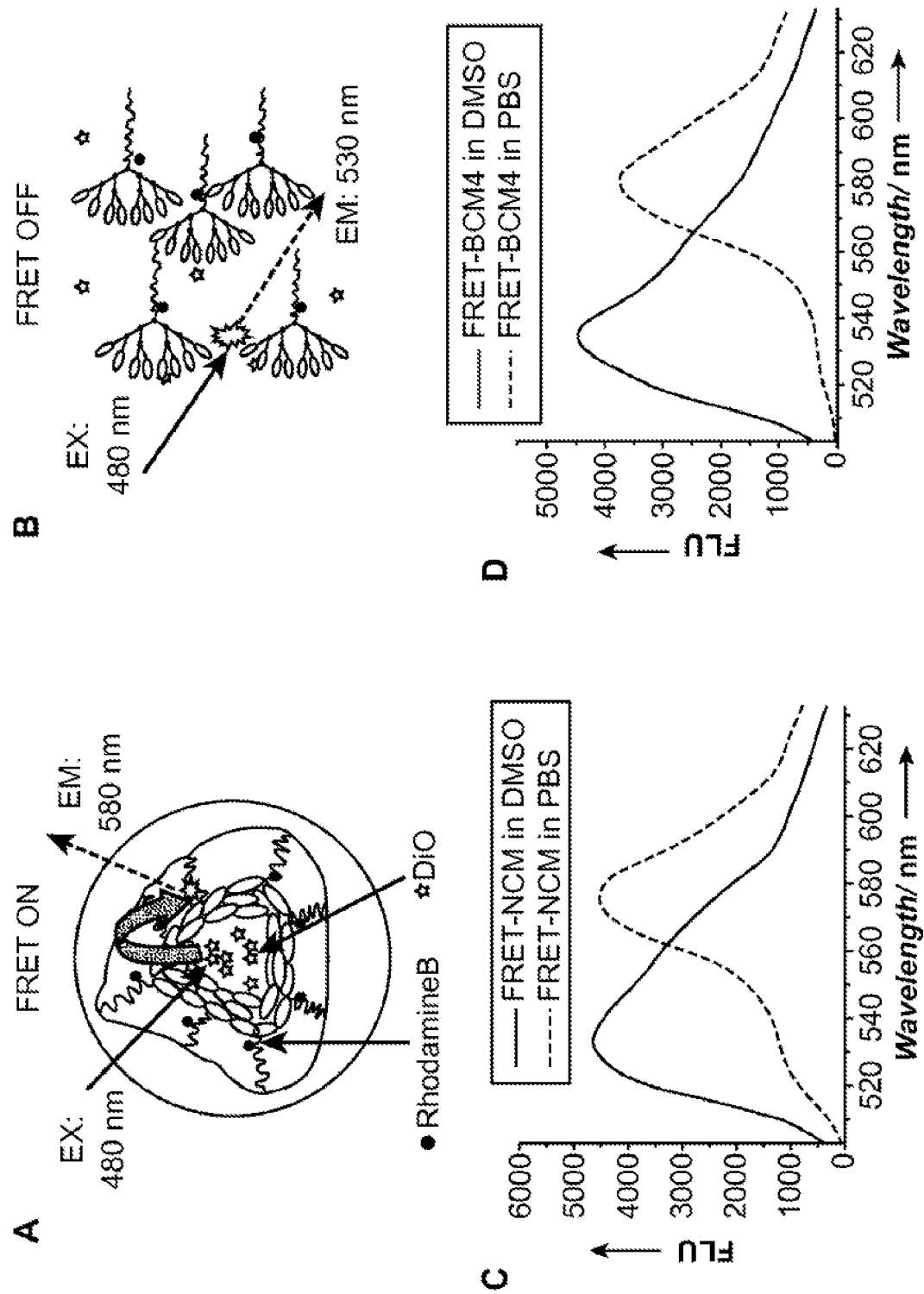
Figure 24:
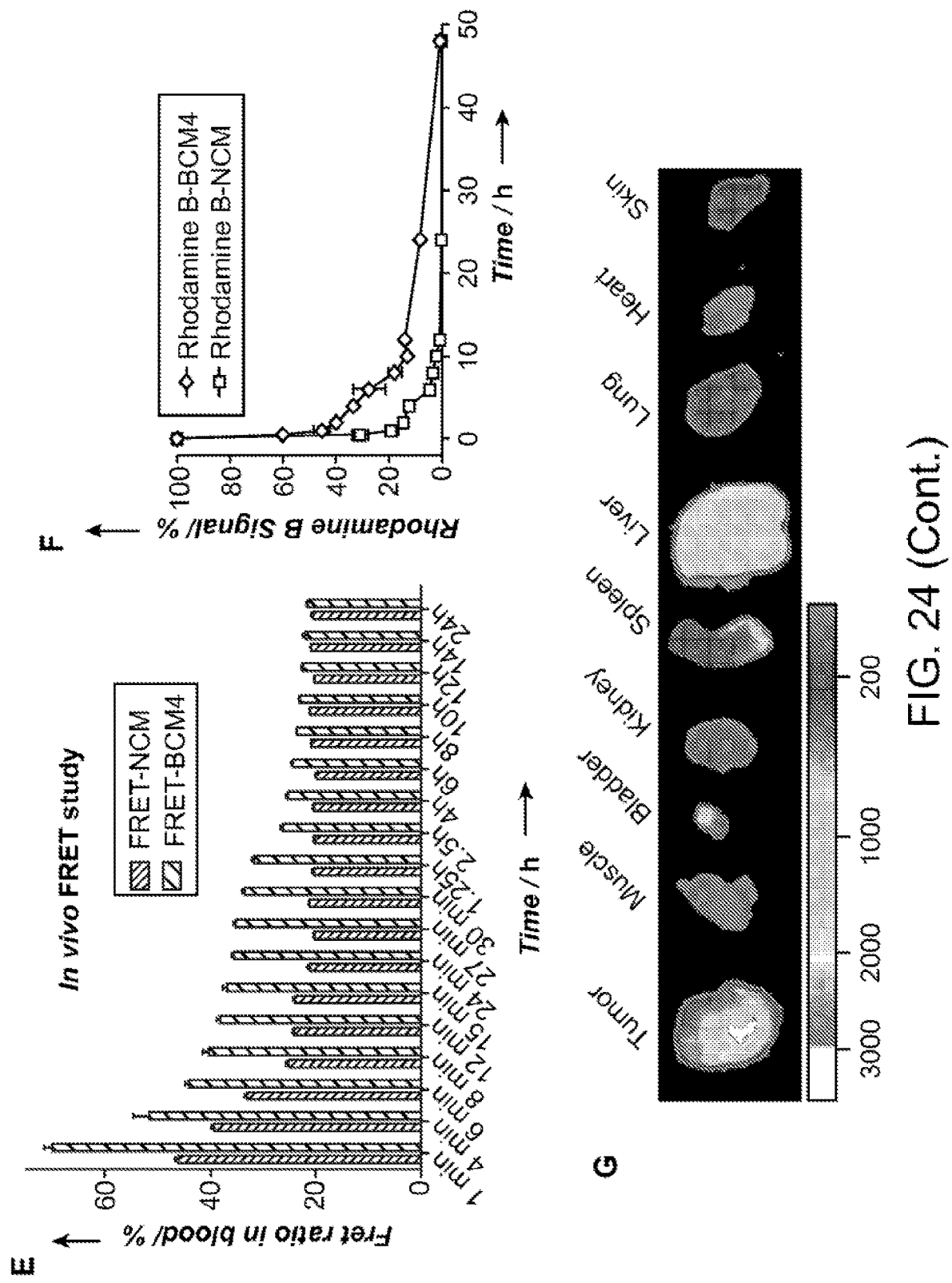

FIG. 24 shows schematic illustration of FRET-NCM in PBS (A) and in DMSO (B) at pH7.4; (C) Fluorescence emission spectra of FRET-NCM in PBS (red line) and DMSO (black line) with 480 nm excitation. (D) Emission spectra of FRET-BCM4 in PBS (red line) and DMSO (black line) with 480 nm excitation. (E) The FRET ratio ($I_{rfhodamine\ B}/(I_{rhodamine\ B}+I_{DiO})$) in blood of nude mice (n=3) over time after intravenous injection of 100 μL FRET-NCM and FRET-BCM4 (2.0 mg/mL). Excitation: 480 nm. (F) The fluorescence signal changes of rhodamine B conjugated NCM and BCM4 in the blood collected at different time points after intravenous injection in the nude mice (n=3). Excitation: 540 nm. (G) Ex vivo near infrared fluorescence (NIRF) images of SKOV-3 xenograft bearing mouse obtained after intravenous injection of BCM4 co-loaded with PTX and DiD.

Figure 25:
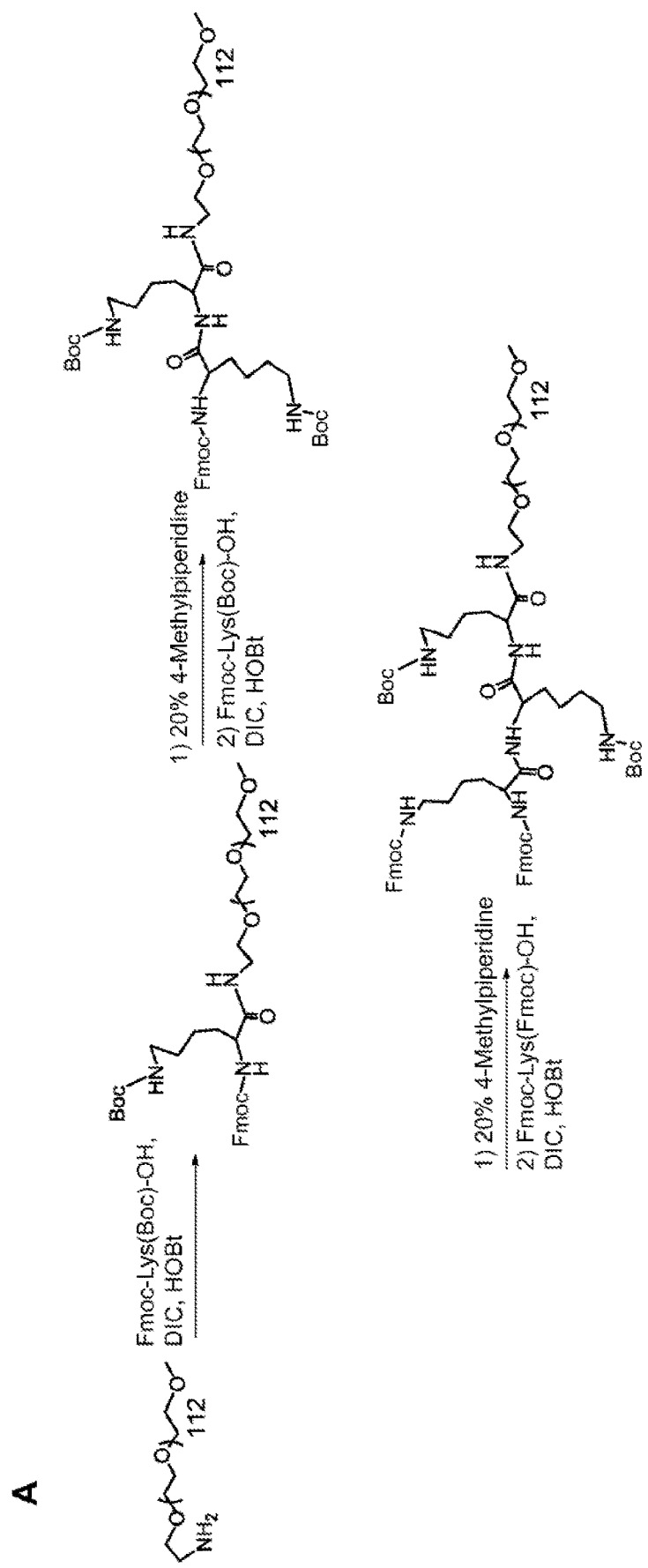

FIG. 25 shows synthetic schemes (A, B and C) for the catechol containing telodendrimers and boronic acid containing telodendrimers. The pinacol esters of boronic acid containing telodendrimers were removed via DCM/TFA (1/1, v/v) at the last step. The synthetic scheme of $PEG^{5k}$-$BA_2$-$CA_8$ was shown as an example.

Figure 26:
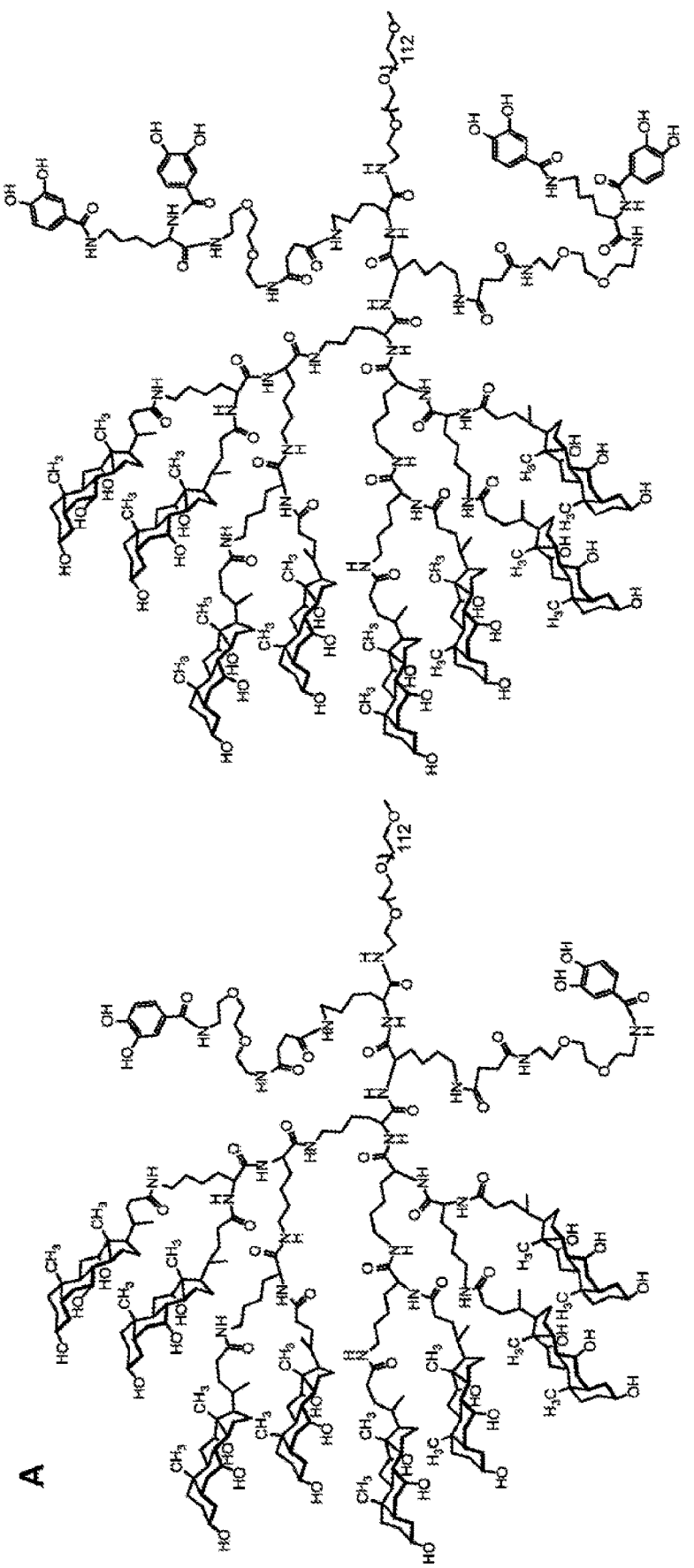

FIG. 26 shows the chemical structure of the catechol (A) containing telodendrimers and boronic acid (B and C) containing telodendrimers.

Figure 27:
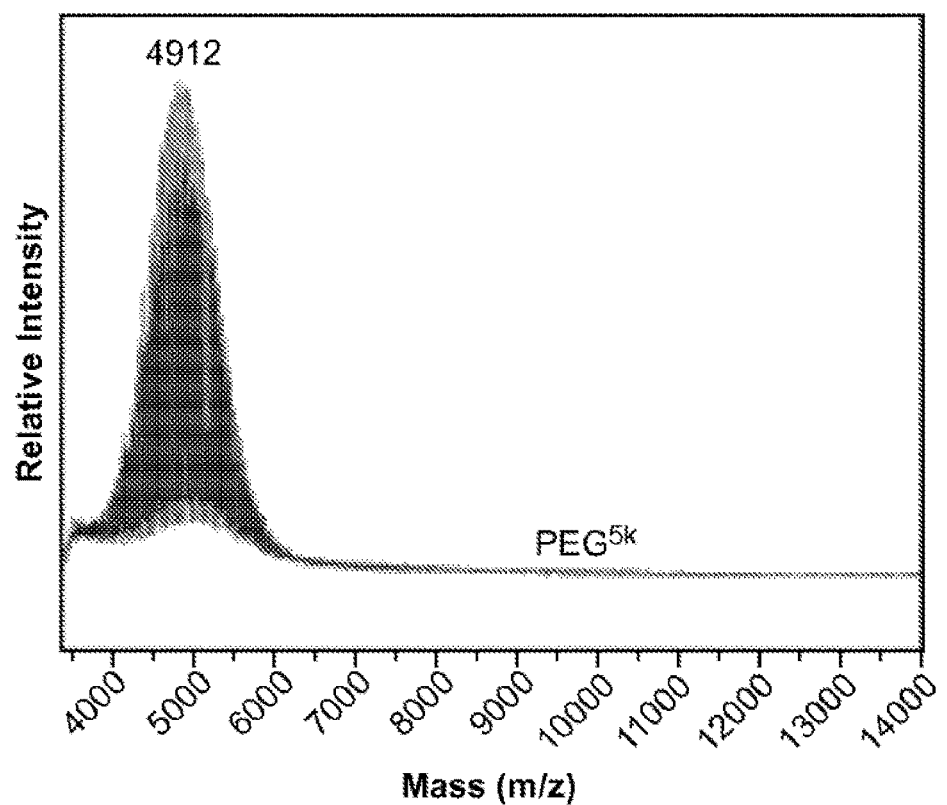
Figure 27:
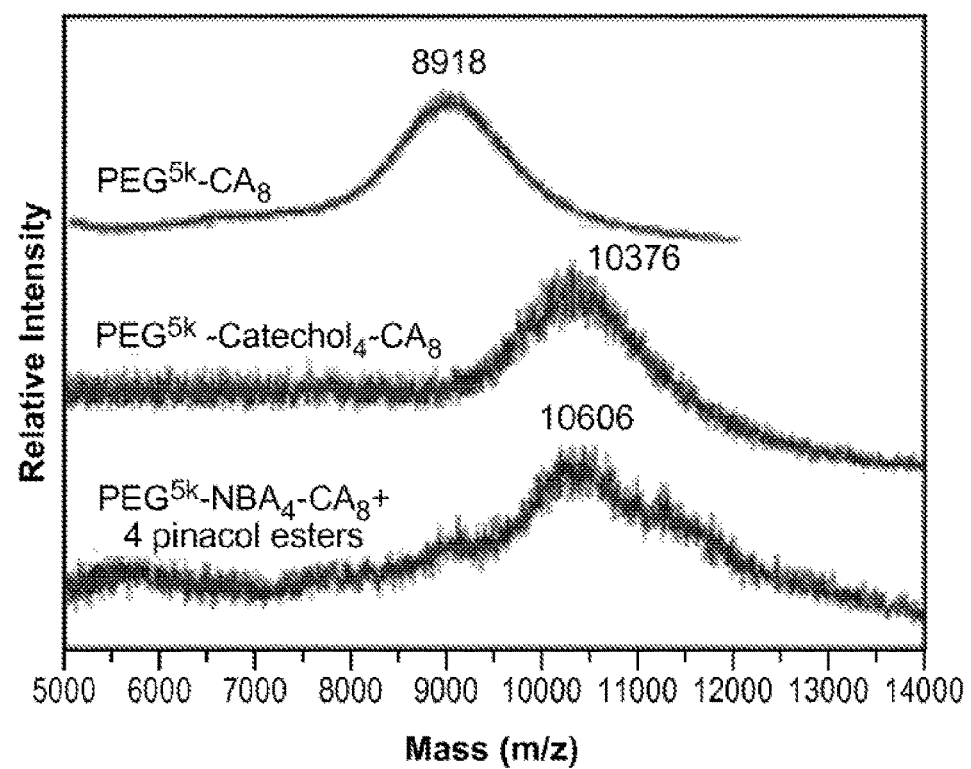

FIG. 27 shows the MALDI-TOF MS of the starting PEG and the representative telodendrimer pair ($PEG^{5k}$-$NBA_4$-$CA_8$/$PEG^{5k}$-Catechol$_4$-$CA_8$) comparing with $PEG^{5k}$-$CA_8$ telodendrimer. The pinacol ester form of $PEG^{5k}$-$NBA_4$-$CA_8$ was shown.

Figure 28:
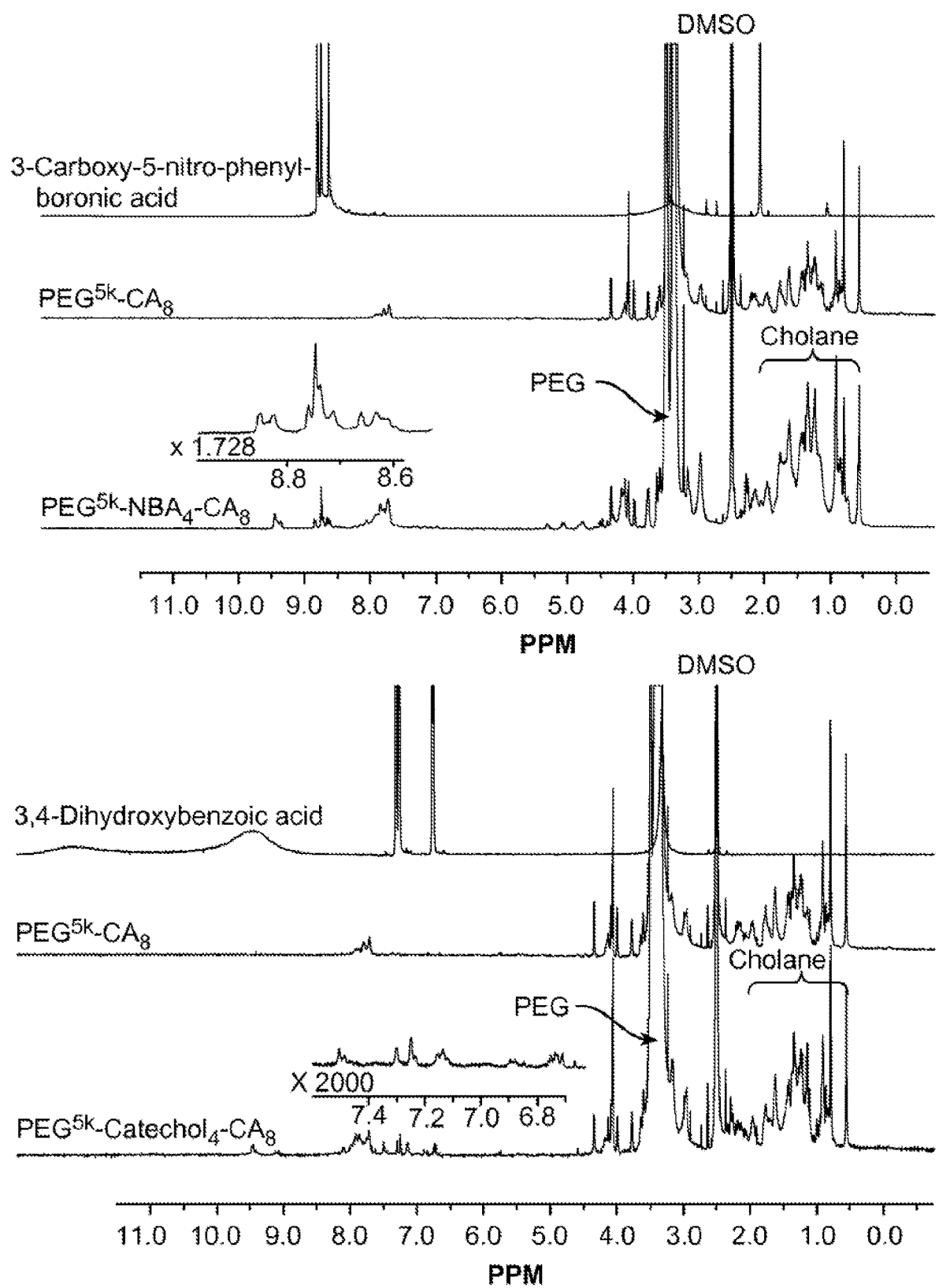

FIG. 28 shows $^1$H NMR spectra of the representative telodendrimer pair ($PEG^{5k}$-$NBA_4$-$CA_8$/$PEG^{5k}$-Catechol$_4$-$CA_8$) comparing with the corresponding small molecular 3-Carboxy-5-nitrophenylboronic acid and 3,4-Dihydroxybenzoic acid as well as $PEG^{5k}$-$CA_8$ telodendrimer recorded in DMSO-d6.

Figure 29:
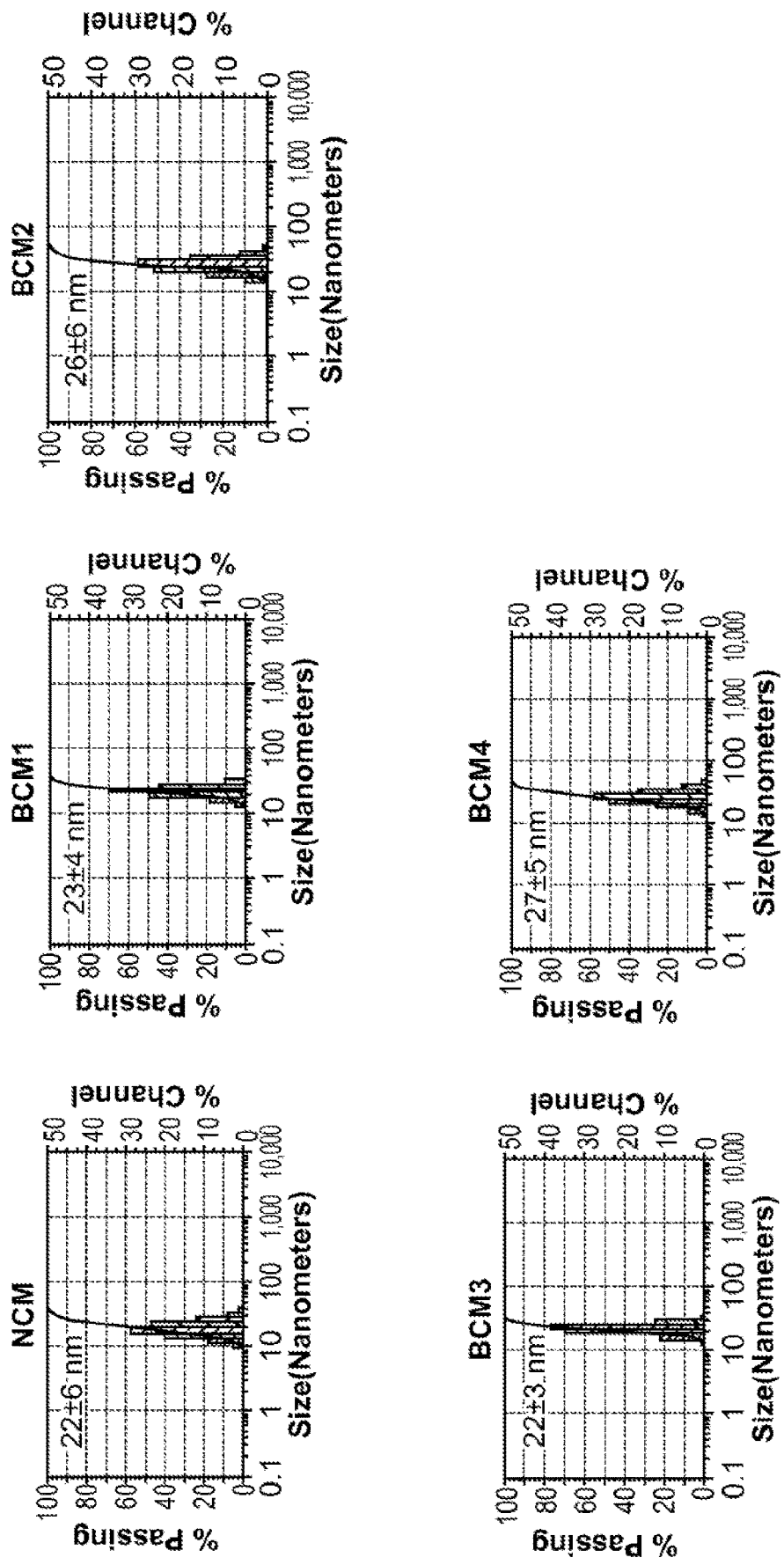

FIG. 29 shows the particle size of NCM, BCM1, BCM2, BCM3 and BCM4, measured by dynamic light scattering (Microtrac®).

Figure 30:
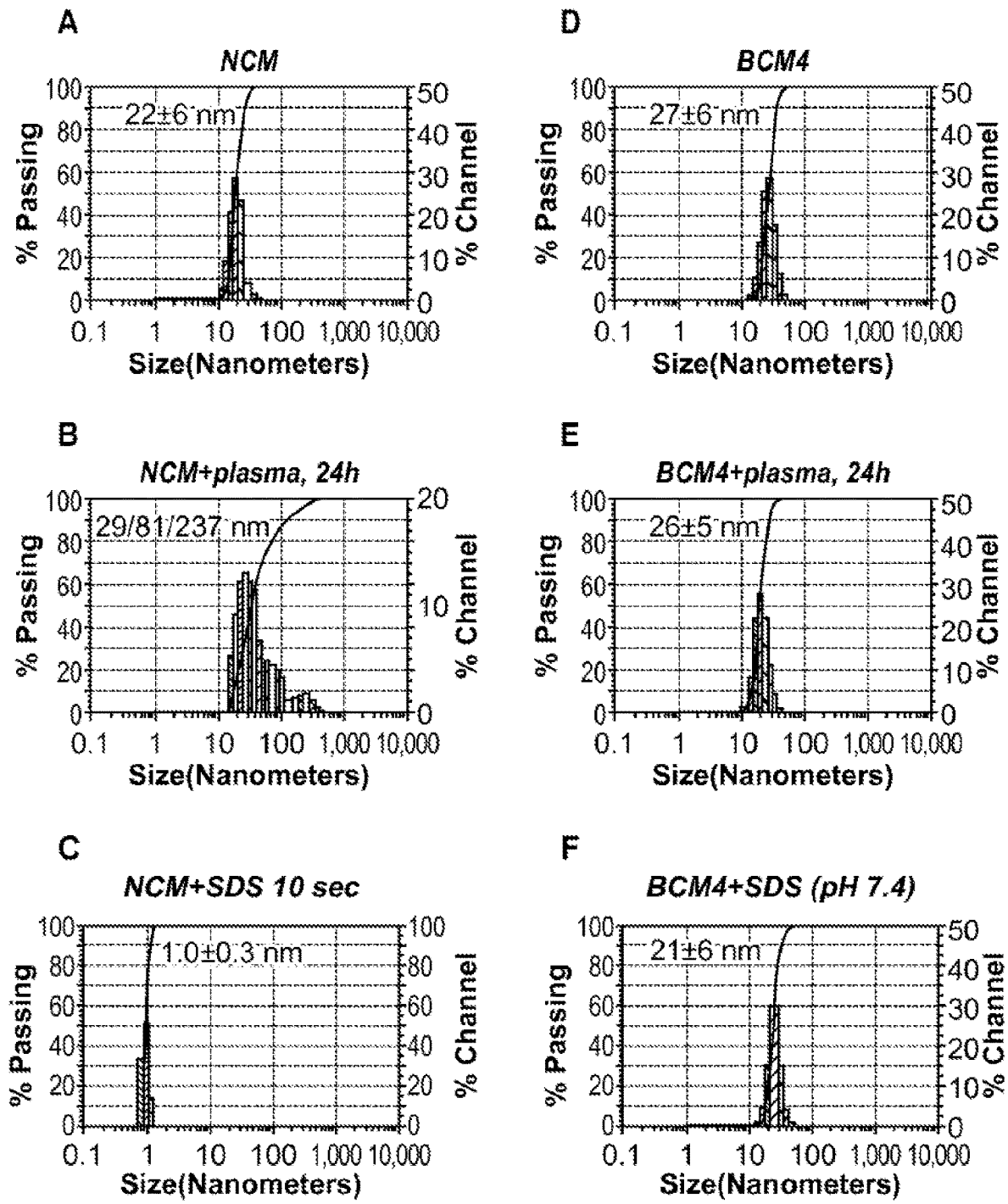
Figure 30:
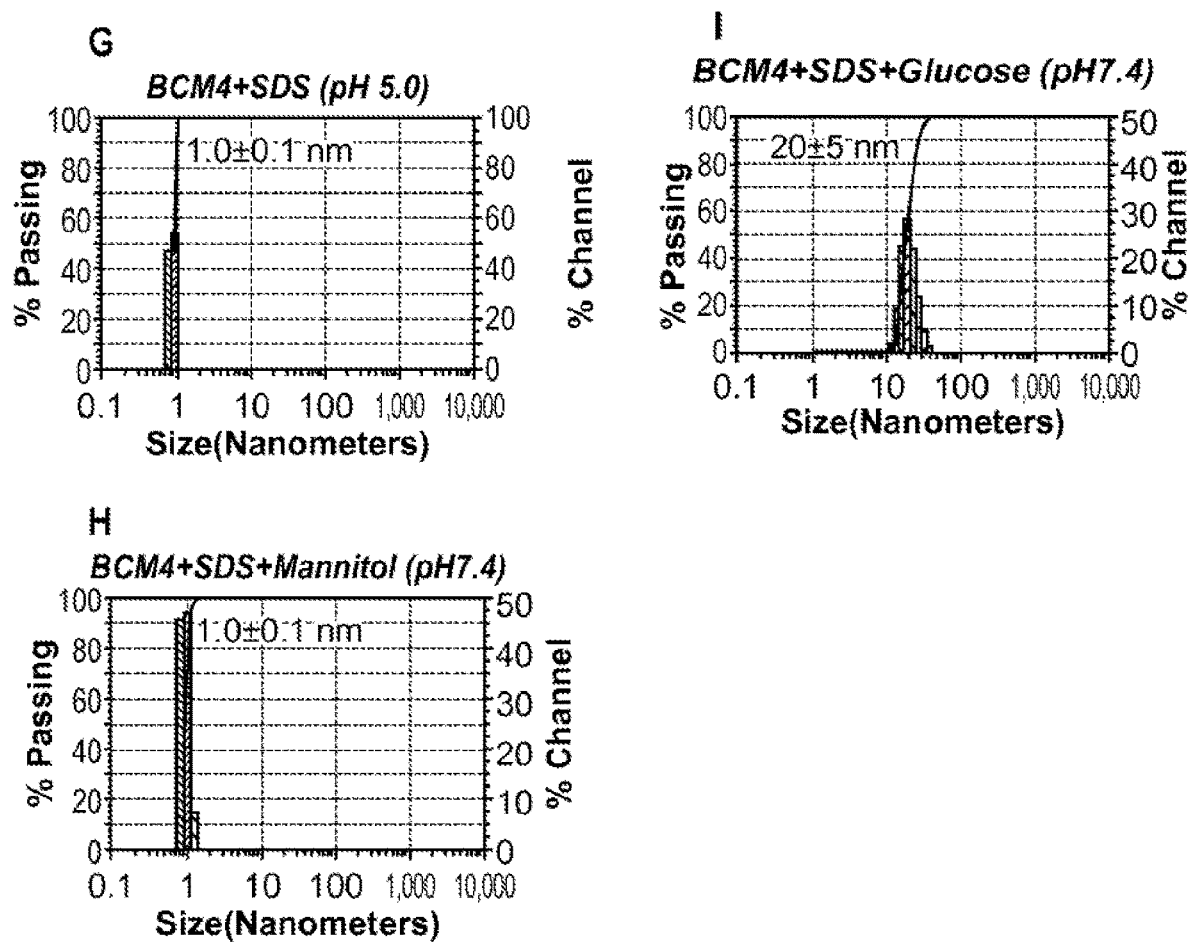

FIG. 30 shows the particle size of NCM in the absence (A) and in the presence (B) of plasma 50% (v/v) for 24 h; The particle size of NCM in the presence of 2.5 mg/mL SDS for 10 sec (C); The particle size of BCM4 in the absence (D) and in the presence of plasma 50% (v/v) for 24ll (E); The particle size of BCM4 in the presence of 2.5 mg/mL SDS for 120 min (F); The particle size of BCM4 in SDS for 120 min and then adjusted the pH of the solution to 5.0 for 20 min (G), The particle size of BCM4 in SDS for 120 min and then treated with mannitol (100 mM) for 20 min (H) The particle size of BCM4 in SDS for 120 min and then treated with glucose (100 mM) for 20 min (I). The particle size was measured by dynamic light scattering (Microtrac). The concentration of micelles was kept at 1.0 mg/mL in PBS.

Figure 31:
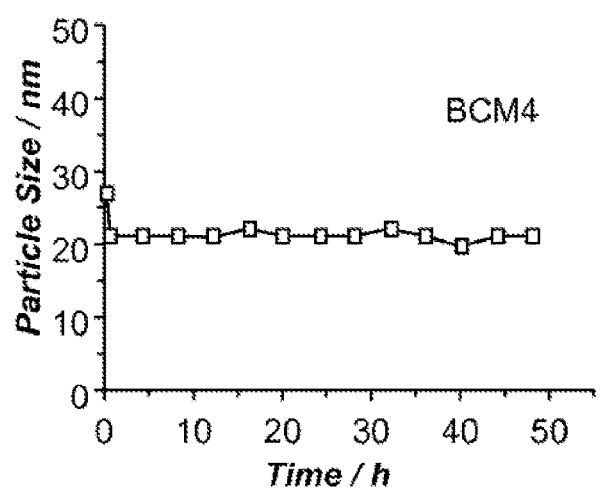

FIG. 31 shows continuous particle size measurements of BCM4 in the presence of 2.5 mg/mL SDS at pH 7.4 via DLS. The concentration of micelles was kept at 1.0 mg/mL.

Figure 32:
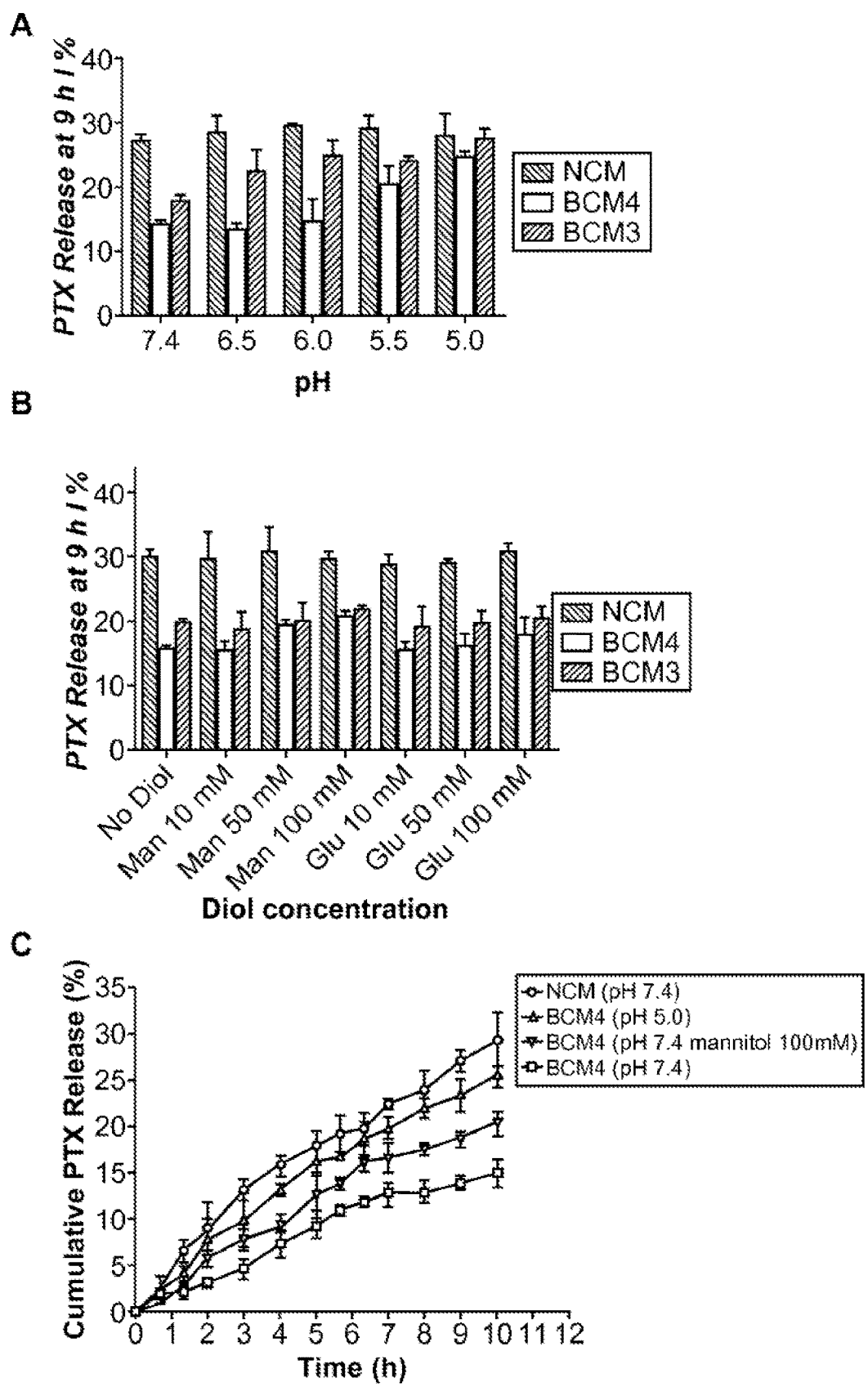

FIG. 32 shows PTX release from NCM, BCM3 and BCM4 at 9 h (A) at different pH levels and (B) in the presence of different concentrations of mannitol (Man) or glucose (Glu). (C) Cumulative PTX release profiles of BCM4 at different pH levels (5.0 and 7.4) and in the presence of mannitol (100 mM) compared with that of NCM at pH7.4.

Figure 33:
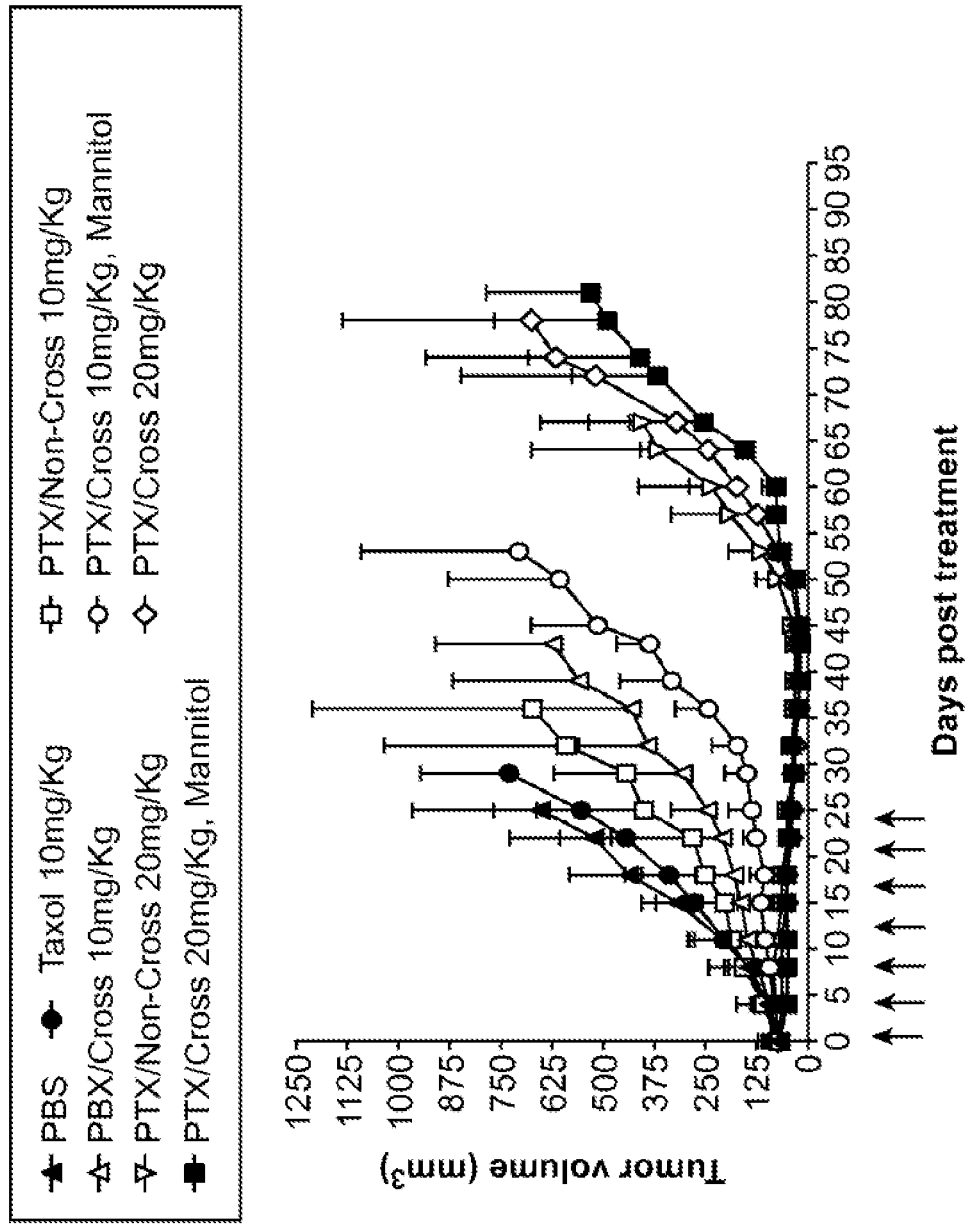

FIG. 33 shows therapeutic efficacies (tumor size) of various formulations of paclitaxel, non-cross-linked and boronate-catechol cross-inked nanoparticles, with and without mannitol given 24 hr after each dose of nanoparticle drug.

Figure 34:
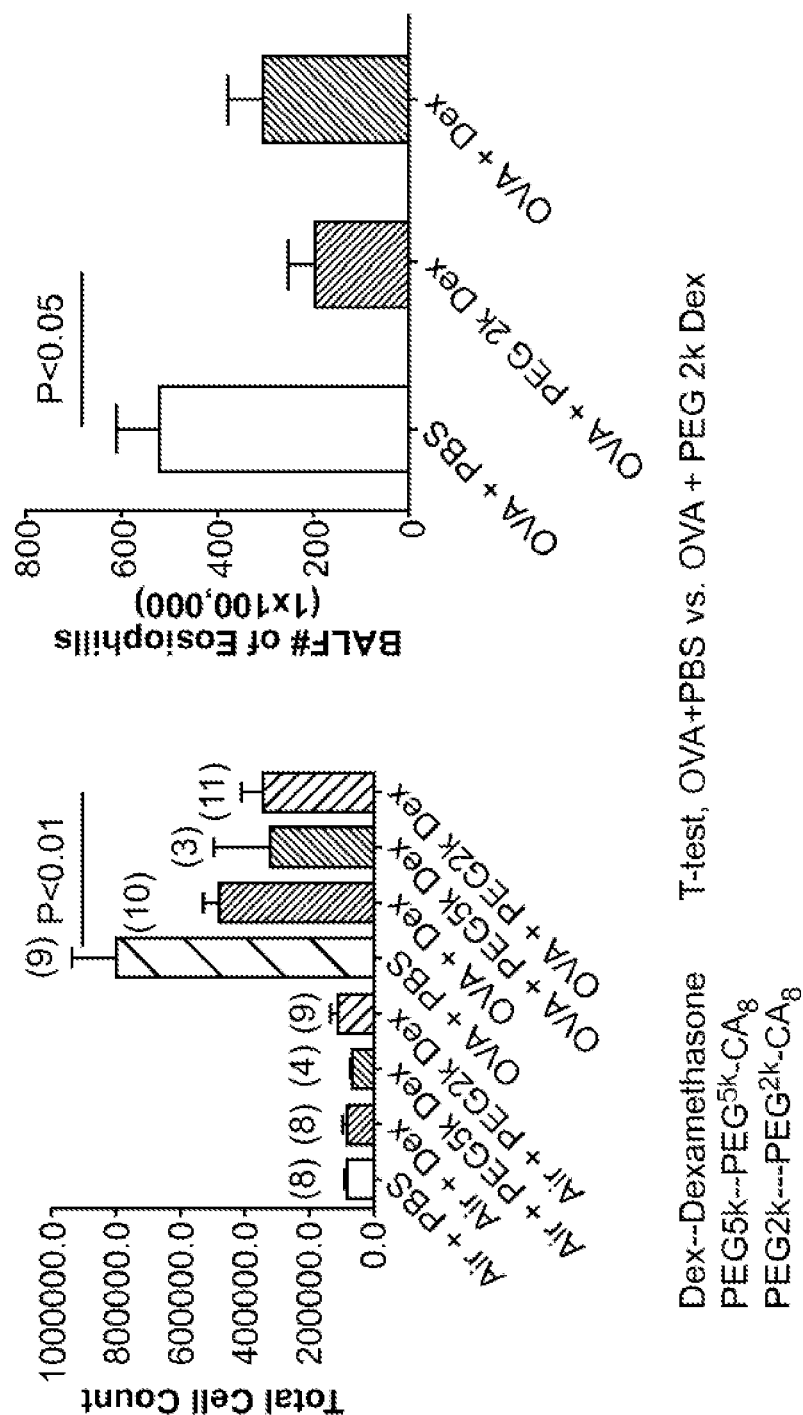

FIG. 34 shows intravenous dexamethasone (Dex) loaded into nanocarriers decreases lung lavage eosinophil counts to a greater degree than equivalent doses of iv Dex alone.

DETAILED DESCRIPTION OF THE INVENTION

I. General

The present invention provides telodendrimers having crosslinking groups such that the nanocarrier micelles formed from the telodendrimers are crosslinked to improve stability of the nanocarrier micelle. The crosslinking groups can be on the dendritic polymer itself, or on the linking portion between the dendritic polymer and the PEG group. Any suitable crosslinking group can be used, such as those capable of reacting with themselves, or a complementary pair of functional groups that react with each other.

II. Definitions

As used herein, the terms "dendrimer" and "dendritic polymer" refer to branched polymers containing a focal point, a plurality of branched monomer units, and a plurality of end groups. The monomers are linked together to form arms (or "dendrons") extending from the focal point and terminating at the end groups. The focal point of the dendrimer can be attached to other segments of the compounds of the invention, and the end groups may be further functionalized with additional chemical moieties.

As used herein, the term "telodendrimer" refers to a dendrimer containing a hydrophilic PEG segment and one or more chemical moieties covalently bonded to one or more end groups of the dendrimer. These moieties can include, but are not limited to, hydrophobic groups, hydrophilic groups, amphiphilic compounds, and drugs. Different moieties may be selectively installed at a desired end group using orthogonal protecting group strategies.

As used herein, the term "bow-tie dendrimer" or "bow-tie telodendrimer" refers to a dendrimer containing two branched segments, such as a dendrimer and a branched PEG moiety, that are linked together at their focal points using a linker moiety.

As used herein, the term "nanocarrier" refers to a micelle resulting from aggregation of die dendrimer conjugates of the invention. The nanocarrier has a hydrophobic core and a hydrophilic exterior.

As used herein, the terms "monomer" and "monomer unit" refer to a diamino carboxylic acid, a dihydroxy carboxylic acid and a hydroxyl amino carboxylic acid. Examples of diamino carboxylic acid groups of the present invention include, but are not limited to, 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl) butyric acid and 5-amino-2-(3-aminopropyl) pentanoic acid. Examples of dihydroxy carboxylic acid groups of the present invention include, but are not limited to, glyceric acid, 2,4-dihydroxybutyric acid, glyceric acid, 2,4-dihydroxybutyric acid, 2,2-Bis(hydroxymethyl)propionic acid and 2,2-Bis(hydroxymethyl) butyric acid. Examples of hydroxyl amino carboxylic acids include, but are not limited to, serine and homoserine. One of skill in the art will appreciate that other monomer units are useful in the present invention.

As used herein, the term "amino acid" refers to a carboxylic acid bearing an amine functional group. Amino acids include the diamino carboxylic acids described above. Amino acids include naturally occurring α-amino acids, wherein the amine is bound to the carbon adjacent to the carbonyl carbon of the carboxylic acid. Examples of naturally occurring α-amino acids include, but are not limited to, L-aspartic acid, L-glutamic acid, L-histidine, L-lysine, and L-arginine. Amino acids may also include the D-enantiomers of naturally occurring α-amino acids, as well as β-amino acids and other non-naturally occurring amino acids.

As used herein, the term "linker" refers to a chemical moiety that links one segment of a dendrimer conjugate to another. The types of bonds used to link the linker to the segments of the dendrimers include, but are not limited to, amides, amines, esters, carbamates, ureas, thioethers, thiocarbamates, thiocarbonate and thioureas. One of skill in the art will appreciate that other types of bonds are useful in the present invention.

As used herein, the term "oligomer" refers to five or fewer monomers, as described above, covalently linked together. The monomers may be linked together in a linear or branched fashion. The oligomer may function as a focal point for a branched segment of a telodendrimer.

As used herein, the term "hydrophobic group" refers to a chemical moiety that is water-insoluble or repelled by water. Examples of hydrophobic groups include, but are not limited to, long-chain alkanes and fatty acids, fluorocarbons, silicones, certain steroids such as cholesterol, and many polymers including, for example, polystyrene and polyisoprene.

As used herein, the term "hydrophilic group" refers to a chemical moiety that is water-soluble or attracted to water. Examples of hydrophilic groups include, but are not limited to, alcohols, short-chain carboxylic acids, quaternary amines, sulfonates, phosphates, sugars, and certain polymers such as PEG.

As used herein, the term "amphiphilic compound" refers to a compound having both hydrophobic portions and hydrophilic portions. For example, the amphiphilic compounds of the present invention can have one hydrophilic face of the compound and one hydrophobic face of the compound. Amphiphilic compounds useful in the present invention include, but are not limited to, cholic acid and cholic acid analogs and derivatives.

As used herein, the term "cholic acid" refers to (R)-4-((3R,5S,7R,8R,9S,10S,12S,13R,14S,17R)-3,7,12-trihydroxy-10,13-dimethylhexadecahydro- 1H-cyclopenta[a]phenanthren-17-yl)pentanoic acid. Cholic acid is also known as 3α,7α,12α-trihydroxy-5β-cholanoic acid; 3-α,7-α,12-α-Trihydroxy-5-β-cholan-24-oic acid; 17-β-(1-methyl-3-carboxypropyl)etiocholane-3 α,7 α,12 α-triol; cholalic acid; and cholalin. Cholic acid derivatives and analogs, such as allocholic acid, pythocholic acid, avicholic acid, deoxycholic acid, chenodeoxycholic acid, are also useful in the present invention. Cholic acid derivatives can be designed to modulate the properties of the nanocarriers resulting from telodendrimer assembly, such as micelle stability and membrane activity. For example, the cholic acid derivatives can have hydrophilic faces that are modified with one or more glycerol groups, aminopropanediol groups, or other groups.

As used herein, the terms "drug" or "therapeutic agent" refers to an agent capable of treating and/or ameliorating a condition or disease. A drug may be a hydrophobic drug, which is any drug that repels water. Hydrophobic drugs useful in the present invention include, but are not limited to, paclitaxel, doxorubicin, etoposide, irinotecan, SN-38, cyclosporin A, podophyllotoxin, Carmustine, Amphotericin, Ixabepilone, Patupilone (epothelone class), rapamycin and platinum drugs. The drugs of the present invention also include prodrug forms. One of skill in the art will appreciate that other drugs are useful in the present invention.

As used herein, the term "crosslinkable group" or "crosslinking group" refers to a functional group capable of binding to a similar or complementary group on another molecule, for example, a first crosslinkable group on a first dendritic polymer linking to a second crosslinkable group on a second dendritic polymer. Groups suitable as crosslinkable and crosslinking groups in the present invention include thiols such as cysteine, boronic acids and 1,2-diols including 1,2-dihydroxybenzenes such as catechol. When the crosslinkable and crosslinking groups combine, they form cross-linked bonds such as disulfides and boronic esters. Other crosslinkable and crosslinking groups are suitable in the present invention.

As used herein, the term "bond cleavage component" refers to an agent capable of cleaving the cross-linked bonds formed using the crosslinkable and crosslinking groups of the present invention. The bond cleavage component can be a reducing agent, such as glutathione, when the cross-linked bond is a disulfide, or mannitol when the cross-linked bond is formed from a boronic acid and 1,2-diol.

As used herein, the term "imaging agent" refers to chemicals that allow body organs, tissue or systems to be imaged. Exemplary imaging agents include paramagnetic agents, optical probes, and radionuclides.

As used herein, the terms "treat", "treating" and "treatment" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter; including, e.g., the result of a physical examination.

As used herein, the term "subject" refers to animals such as mammals, including, but not limited to, primates (e.g., humans), cows, sheep, goats, horses, dogs, cats, rabbits, rats, mice and the like. In certain embodiments, the subject is a human.

As used herein, the terms "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

III. Telodendrimers

The present invention provides crosslinkable telodendrimer conjugates having a hydrophilic poly(ethylene glycol) (PEG) segment and a hydrophobic segment. The PEG segment can have a branched or linear architecture including one or more PEG chains. The hydrophobic segment of the telodendrimer can be provided by cholic acid, which has a hydrophobic face and a hydrophilic face. The cholic acid and the PEG are connected by oligomers and/or polymers that can contain a variety of acid repeats units. Typically, the oligomers and polymers comprise a diamino carboxylic acid, lysine. The telodendrimers are also functionalized with a crosslinkable group. The telodendrimers can aggregate in solution to form micelles with a hydrophobic interior and a hydrophilic exterior, and can be used as nanocarriers to deliver drugs or other agents having low water solubility. Following micelle formation, the telodendrimers can be crosslinked using the crosslinkable groups, forming a more stable micelle.

The present invention provides a PEGylated dendrimer, referred to as a telodendrimer, containing cholic acid groups and other moieties at the dendrimer periphery, and crosslinkable groups. In some embodiments, the invention provide a compound of formula I:

$$(PEG)_m\text{-}A(Y^1)_p\text{-}L\text{-}D(Y^2)_q\text{-}(R)_n \qquad (I)$$

wherein radical A of formula I is linked to at least one PEG group. Radical D of formula I is a dendritic polymer having a single focal point group, a plurality of branched monomer units X and a plurality of end groups. Radical L of formula I is a bond or a linker linked to the focal point group of the dendritic polymer. Each PEG of formula I is a polyethyleneglycol (PEG) polymer, wherein each PEG polymer has a molecular weight of 1-100 kDa. Each R of formula I can be the end group of the dendritic polymer, a hydrophobic group, a hydrophilic group, an amphiphilic compound or a drug, such that when R is not an end group then each R is linked to one of the end groups. Each $Y^1$ and $Y^2$ of formula I is a crosslinkable group that can be any of boronic acid, dihydroxybenzene or a thiol. Subscript m of formula I is an integer from 0 to 20. Subscript n of formula I is an integer from 2 to 20, wherein subscript n is equal to the number of end groups on the dendritic polymer, and wherein at least half the number n of R groups that can each be a hydrophobic group, a hydrophilic group, an amphiphilic compound or a drug. And, each of subscripts p and q are 0 or from 2 to 8, such that one of subscripts p and q is from 2 to 8.

Radical A can be any suitable group capable of linking the PEG to the linker or dendritic polymer D. Suitable A groups include the monomer units X described below for the dendritic polymer. In some embodiments, radical A is a monomer or oligomer of lysine. In some embodiments, radical A is lysine. Radical A can be linked to a crosslinkable group or an imaging agent, either directly or via a linker. In some embodiments, radical A can also include at least one imaging agent. Imaging agents useful for attachment to the telodendrimers of the present invention include, but are not limited to, fluorescent dyes, chelates and radiometals.

The dendritic polymer can be any suitable dendritic polymer. The dendritic polymer can be made of branched monomer units including amino acids or other bifunctional AB2-type monomers, where A and B are two different functional groups capable of reacting together such that the resulting polymer chain has a branch point where an A-B bond is formed. In some embodiments, each branched monomer unit X can be a diamino carboxylic acid, a dihydroxy carboxylic acid and a hydroxyl amino carboxylic acid. In some embodiments, each diamino carboxylic acid can be 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl) butyric acid or 5-amino-2-(3-aminopropyl) pentanoic acid. In some embodiments, each dihydroxy carboxylic acid can be glyceric acid, 2,4-dihydroxybutyric acid, 2,2-Bis(hydroxymethyl)propionic acid, 2,2-Bis(hydroxymethyl)butyric acid, serine or threonine. In some embodiments, each hydroxyl amino carboxylic acid can be serine or homoserine. In some embodiments, the diamino carboxylic acid is an amino acid. In some embodiments, each branched monomer unit X is lysine.

The dendritic polymer of the telodendrimer can be any suitable generation of dendrimer, including generation 1, 2, 3, 4, 5, or more, where each "generation" of dendrimer refers to the number of branch points encountered between the focal point and the end group following one branch of the dendrimer. The dendritic polymer of the telodendrimer can also include partial-generations such as 1.5, 2.5, 3.5, 4.5, 5.5, etc., where a branch point of the dendrimer has only a single branch. The various architectures of the dendritic polymer can provide any suitable number of end groups, including, but not limited to, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or 32 end groups.

The focal point of a telodendrimer or a telodendrimer segment may be any suitable functional group. In some embodiments, the focal point includes a functional group that allows for attachment of the telodendrimer or telodendrimer segment to another segment. The focal point functional group can be a nucleophilic group including, but not limited to, an alcohol, an amine, a thiol, or a hydrazine. The focal point functional group may also be an electrophile such as an aldehyde, a carboxylic acid, or a carboxylic acid derivative including an acid chloride or an N-hydroxysuccinimidyl ester.

The R groups installed at the telodendrimer periphery can be any suitable chemical moiety, including hydrophilic groups, hydrophobic groups, or amphiphilic compounds. Examples of hydrophobic groups include, but are not limited to, long-chain alkanes and fatty acids, fluorocarbons, silicones, certain steroids such as cholesterol, and many polymers including, for example, polystyrene and polyisoprene. Examples of hydrophilic groups include, but are not limited to, alcohols, short-chain carboxylic acids, amines, sulfonates, phosphates, sugars, and certain polymers such as PEG. Examples of amphiphilic compounds include, but are not limited to, molecules that have one hydrophilic face and one hydrophobic face.

Amphiphilic compounds useful in the present invention include, but are not limited to, cholic acid and cholic acid analogs and derivatives. "Cholic acid" refers to (R)-4-((3R,5S,7R,8R,9S,10S,12S,13R,14S,17R)-3,7,12-trihydroxy-10,13-dimethylhexadecahydro-1H-cyclopenta[a]phenanthren-17-yl)pentanoic acid, having the structure:

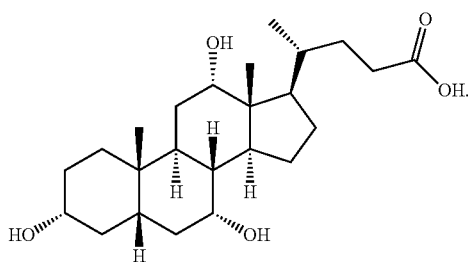

Cholic acid derivatives and analogs include, but are not limited to, allocholic acid, pythocholic acid, avicholic acid, deoxycholic acid, and chenodeoxycholic acid. Cholic acid derivatives can be designed to modulate the properties of the nanocarriers resulting from telodendrimer assembly, such as micelle stability and membrane activity. For example, the cholic acid derivatives can have hydrophilic faces that are modified with one or more glycerol groups, aminopropanediol groups, or other groups.

Telodendrimer end groups may also include drugs such as paclitaxel, doxorubicin, etoposide, irinotecan, SN-38, cyclosporin A, podophyllotoxin, carmustine, amphotericin, ixabepilone, patupilone (epothelone class), rapamycin and platinum drugs. One of skill in the art will appreciate that other drugs are useful in the present invention.

In some embodiments, each R can be cholic acid, (3α,5β,7α,12α)-7,12-dihydroxy-3-(2,3-dihydroxy-1-propoxy)-cholic acid, (3α,5β,7α,12α)-7-hydroxy-3,12-di(2,3-dihydroxy-1-propoxy)-cholic acid, (3α,5β,7α,12α)-7,12-dihydroxy-3-(3-amino-2-hydroxy-1-propoxy)-cholic acid, cholesterol formate, doxorubicin, or rhein. In some embodiments, each R can be cholic acid.

The telodendrimer backbone can vary, depending on the number of branches and the number and chemical nature of the end groups and R groups, which will modulate solution conformation, rheological properties, and other characteristics. The telodendrimers can have any suitable number n of end groups and any suitable number of R groups. In some embodiments, n can be 2-70, or 2-50, or 2-30, or 2-10. Subscript n can be about 2, 3, 4, 5, 6, 7, 8, 9, 10, 15, or 20. In some embodiments, subscript n can be from 2 to 10, 2 to 8, or 4 to 8. In some embodiment, 71 is 2-20.

The telodendrimer can have a single type of R group on the periphery, or any combination of R groups in any suitable ratio. For example, at least half the number n of R groups can be a hydrophobic group, a hydrophilic group, an amphiphilic compound, a drug, or any combination thereof. In some embodiments, half the number n of R groups are amphiphilic compounds.

In some embodiments, each R group is the same. In some embodiments, at least two different R groups are present, such as two different amphiphilic groups, or an amphiphilic group and a drug, or an amphiphilic group and a dendritic polymer end group, or two different drugs, or a drug and a dendritic end group.

The linker L can include any suitable linker. In general, the linkers are bifunctional linkers, having two functional groups for reaction with each of two telodendrimer segments. In some embodiments, the linker can be a heterobifunctional linker. In some embodiments, the linker can be a homobifunctional linker. In some embodiments, the linker L can be polyethylene glycol, polyserine, polyglycine, poly(serine-glycine), aliphatic amino acids, 6-amino hexanoic acid, 5-amino pentanoic acid, 4-amino butanoic acid or beta-alanine. One of skill in the art will recognize that the size and chemical nature of the linker can be varied based on the structures of the telodendrimer segments to be linked.

In some embodiments, linker L is the Ebes linker having the formula:

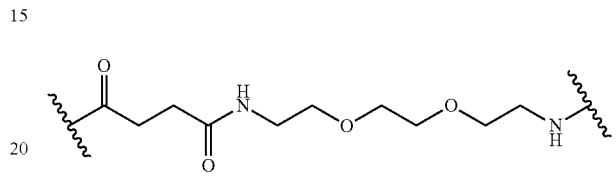

Polyethylene glycol (PEG) polymers of any size and architecture are useful in the nanocarriers of the present invention. In some embodiments, the PEG is from 1-100 kDa. In other embodiments, the PEG is from 1-10 kDa. In some other embodiments, the PEG is about 3 kDa. In still other embodiments, additional PEG polymers are linked to the amphiphilic compounds. For example, when the amphiphilic compound is cholic acid, up to 3 PEG polymers are linked to each cholic acid. The PEG polymers linked to the amphiphilic compounds are from 200-10,000 Da in size. In yet other embodiments, the PEG polymers linked to the amphiphilic compounds are from 1-5 kDa in size. One of skill in the art will appreciate that other PEG polymers and other hydrophilic polymers are useful in the present invention. PEG can be any suitable length.

Any suitable number of PEG groups can be present. For example, subscript m can be 0, 1, 2, 3, 4, 5, 10, 15, or 20. Subscript m can also be from 0 to 5, 0 to 4, 0 to 3, 0 to 2, 1 to 5, 1 to 4, or 1 to 3. In some embodiments, subscript m is 1.

Crosslinkable groups suitable in the compounds of the present invention include any functional group capable of forming a covalent bond with the same functional group on another telodendrimer, or with a complementary functional group on another telodendrimer. Functional groups capable of forming a covalent bond with the same functional group include thiols. Thiols useful in the compounds of the present invention include any thiols, such as cysteine.

Complementary functional groups capable of forming a covalent bond include boronic acid and a 1,2-diol. Boronic acids useful in the compounds of the present invention include, but are not limited to, phenylboronic acid, 2-thienylboronic acid, methylboronic acid, and propenylboronic acid. Suitable 1,2-diols include alkyl-1,2-diol and phenyl-1,2-diols such as catechol.

In some embodiments, each crosslinkable group $Y^1$ and $Y^2$ can be any of boronic acid, dihydroxybenzene or a thiol. In some embodiments, each crosslinkable group $Y^1$ and $Y^2$ can be any of boronic acid or dihydroxybenzene. In some embodiments, each crosslinkable group $Y^1$ and $Y^2$ can be phenylboronic acid or dihydroxybenzene. In some embodiments, each crosslinkable group $Y^1$ can be phenylboronic acid or dihydroxybenzene. In some embodiments, each crosslinkable group $Y^1$ can be carboxyphenylboronic acid, carboxynitrophenyl boronic acid or 3,4-dihydroxybenzoic acid. In some embodiments, each crosslinkable group $Y^1$ and $Y^2$ can be a thiol. In some embodiments, each crosslinkable group $Y^1$ and $Y^2$ can be cysteine. In some embodiments, each crosslinkable group $Y^2$ can be cysteine.

In some embodiments, the compound of formula I has the structure:

wherein subscript p is an integer from 2 to 8 and subscript q is 0.

In some embodiments, the compound of formula has the structure:

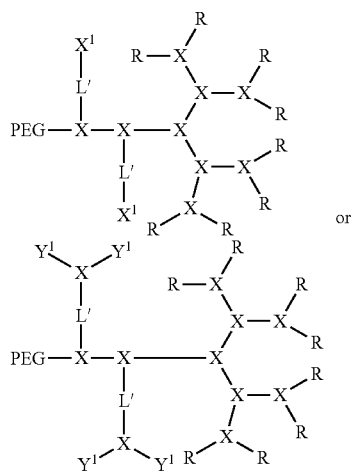

wherein each L' is a linker Ebes, PEG is PEG5k, each R is cholic acid, each branched monomer unit X is lysine, and $Y^1$ can be carboxyphenylboronic acid, carboxynitrophenyl boronic acid and 3,4-dihydroxybenzoic acid.

In other embodiments, the compound of formula I has the structure:

wherein subscript p is 0 and subscript q is an integer from 2 to 8.

In some embodiments, the compound of formula has the structure:

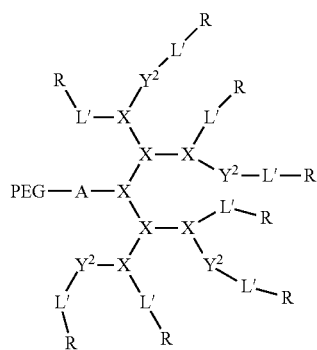

wherein A is lysine, each L' is a linker Ebes, PEG is PEG5k, each R is cholic acid, each branched monomer unit X is lysine, and each $Y^2$ is cysteine.

The compounds and conjugates of the present invention can be prepared by methods known to one of skill in the art. For example, the well-established stepwise Fmoc peptide chemistry method was employed in the preparation of the compounds and conjugates of the present invention, with the resulting thiolated telodendrimers having well-defined polymer structure. In one example, the compound and conjugate is designated as $PEG^{5k}$-$Cys_4$-$L_8$-$CA_8$ corresponding to length of PEG and the number of cysteines, hydrophilic spacers and cholic acids in the structure. As shown in the figures, $PEG^{5k}$-$Cys_4$-$L_8$-$CA_8$ includes a dendritic oligomer of cholic acids attached to one terminus of the linear PEG through a poly(lysine-cysteine-Ebes) backbone. The thiol free telodendrimer, $PEG^{5k}$-$CA_8$ was also synthesized for comparison as described previously. Fluorescent dyes such as BODIPY can be attached to the ε-amino group of the lysine at the junction between the PEG and the oligo-cholic acid chains after removal of Dde protecting group.

IV. Nanocarriers

The telodendrimers of the present invention aggregate to form nanocarriers with a hydrophobic core and a hydrophilic exterior, where the crosslinkable groups are subsequently crosslinked to provide additional stability to the resulting nanocarrier.

In some embodiments, the invention provides a nanocarrier having an interior and an exterior, the nanocarrier including at least two conjugates, wherein each conjugate includes a polyethylene glycol (PEG) polymer, at least two amphiphilic compounds having both a hydrophilic face and a hydrophobic face, at least two crosslinking groups, and a dendritic polymer covalently attached to the PEG, the amphiphilic compounds and the crosslinking groups, wherein each conjugate self-assembles in an aqueous solvent to form the nanocarrier such that a hydrophobic pocket is formed in the interior of the nanocarrier, wherein the PEG of each compound self-assembles on the exterior of the nanocarrier, and wherein at least two conjugates are reversibly crosslinked via the crosslinking groups.

In some embodiments, each conjugate can be a conjugate of the present invention.

The crosslinking groups can be any suitable crosslinking group, as described above. In some embodiments, the crosslinking groups can be thiol, boronic acid or dihydroxybenzene. In some embodiments, the crosslinking groups can be thiol. In some embodiments, a first set of conjugates includes boronic acid crosslinking groups, and a second set of conjugates includes dihydroxybenzene crosslinking groups.

In some embodiments, the nanocarrier also includes a hydrophobic drug or an imaging agent, such that the hydrophobic drug or imaging agent is sequestered in the hydrophobic pocket of the nanocarrier. Hydrophobic drugs useful in the nanocarrier of the present invention includes any drug having low water solubility. In some embodiments, the hydrophobic drug in the nanocarrier can be bortezomib, paclitaxel, SN38, camptothecin, etoposide and doxorubicin, docetaxel, daunorubicin, VP16, prednisone, dexamethasone, vincristine, vinblastine, temsirolimus and carmusine.

In some embodiments, the nanocarrier includes at least one monomer unit that is optionally linked to an optical probe, a radionuclide, a paramagnetic agent, a metal chelate or a drug. The drug can be a variety of hydrophilic or hydrophobic drugs, and is not limited to the hydrophobic drugs that are sequestered in the interior of the nanocarriers of the present invention.

Drugs that can be sequestered in the nanocarriers or linked to the conjugates of the present invention include, but are not limited to, cytostatic agents, cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil); anti-metabolites (such as methotrexate); alkylating agents (such as temozolomide (TEMODAR™ from Schering-Plough Corporation, Kenilworth, N.J.), cyclophosphamide); aromatase combinations; ara-C, adriamycin, cytoxan, and gemcitabine. Other drugs useful in the nanocarrier of the present invention include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN™ from Sanofi-Synthelabo Pharmaceuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17.alpha.-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, or Hexamethylmelamine. Prodrug forms are also useful in the present invention.

Other drugs useful in the present invention also include radionuclides, such as $^{67}$Cu, $^{90}$Y, $^{123}$I, $^{125}$I, $^{131}$I, $^{177}$Lu, $^{188}$Re, $^{186}$Re and $^{211}$At. In some embodiments, a radionuclide can act therapeutically as a drug and as an imaging agent.

Imaging agents include paramagnetic agents, optical probes and radionuclides. Paramagnetic agents include iron particles, such as iron nanoparticles that are sequestered in the hydrophobic pocket of the nanocarrier. In some embodiments, the imaging agent can include organic fluorescent dyes, quantum dots (QDs), super paramagnetic iron oxide nanoparticles (SPIO-NPs), or gold nanoparticles. In some embodiments, the imaging agent is a radionuclide.

Some embodiments of the invention provide nanocarriers wherein each amphiphilic compound can be any of cholic acid, allocholic acid, pythocholic acid, avicholic acid, deoxycholic acid, or chenodeoxycholic acid. In some embodiments, each amphiphilic compound can be cholic acid.

The crosslinking groups of the nanocarrier telodendrimers can be crosslinked by any suitable means known to one of skill in the art. For example, when the crosslinkable group is a thiol, a disulfide bond can be formed between two conjugates of the present invention by oxidation of the thiols. Any suitable oxidation agent can be used, such as oxygen. For other crosslinking groups, such as the complementary groups boronic acid and 1,2-diols such as dihydroxybenzene, the crosslinking occurs spontaneously and without the need for additional reactants.

The crosslinking in the nanocarriers of the present invention is reversible to facilitate delivery of a drug, for example, to a target site. Reversing the crosslinking of the crosslinked nanocarrier requires contacting the crosslinked nanocarrier with a suitable bond cleavage component. In some embodiments, the present invention provides a method of reversing the cross-linking of the reversibly crosslinked nanocarrier of the present invention, by contacting the reversibly crosslinked nanocarrier with a bond cleavage component suitable for cleaving the cross-linked bond, thereby reversing the cross-linking of the reversibly crosslinked nanocarrier. In some embodiments, the contacting is performed in vivo.

Any suitable bond cleavage component can be used in the present invention. In some embodiments, the bond cleavage component can be N-acetyl cysteine (NAC), glutathione, 2-mercaptoethane sulfonate sodium (MESNA), mannitol or acid. When the crosslinked bond is a disulfide, any disulfide reducing agent is suitable. In some embodiments, the bond cleavage component can be N-acetyl cysteine or 2-mercaptoethane sulfonate when the compounds and conjugates of the present invention include a thiol. In some embodiments, the bond cleavage component can be mannitol when the crosslinking groups of the compounds and conjugates of the present invention include boronic acid and dihydroxybenzene.

V. Method of Treating

The nanocarriers of the present invention can be used to treat any disease requiring the administration of a drug, such as by sequestering a hydrophobic drug in the interior of the nanocarrier, or by covalent attachment of a drug to a conjugate of the nanocarrier. The nanocarriers can also be used for imaging, by sequestering an imaging agent in the interior of the nanocarrier, or by attaching the imaging agent to a conjugate of the nanocarrier.

In some embodiments, the present invention provides a method of treating a disease, including administering to a subject in need of such treatment, a therapeutically effective amount of a nanocarrier of the present invention, wherein the nanocarrier includes a drug. The drug can be a covalently attached to a conjugate of the nanocarrier. In some embodiments, the drug is a hydrophobic drug sequestered in the interior of the nanocarrier.

Any suitable drug can be used with the nanocarriers of the present invention. In some embodiments, the hydrophobic drug can be bortezomib, paclitaxel, SN38, camptothecin, etoposide and doxorubicin, docetaxel, daunorubicin, VP16, prednisone, dexamethasone, vincristine, vinblastine, temsirolimus, carmusine, lapatinib, sorafenib, fenretinide, or actinomycin D.

In some embodiments, the nanocarrier also includes an imaging agent. The imaging agent can be a covalently attached to a conjugate of the nanocarrier, or the imaging agent can be sequestered in the interior of the nanocarrier. In some other embodiments, both a hydrophobic drug and an imaging agent are sequestered in the interior of the nanocarrier. In still other embodiments, both a drug and an imaging agent are covalently linked to a conjugate or conjugates of the nanocarrier. In yet other embodiments, the nanocarrier can also include a radionuclide.

The nanocarriers of the present invention can be administered to a subject for treatment, e.g., of hyperproliferative disorders including cancer such as, but not limited to: carcinomas, gliomas, mesotheliomas, melanomas, lymphomas, leukemias, adenocarcinomas, breast cancer, ovarian cancer, cervical cancer, glioblastoma, leukemia, lymphoma, prostate cancer, and Burkitt's lymphoma, head and neck cancer, colon cancer, colorectal cancer, non-small cell lung cancer, small cell lung cancer, cancer of the esophagus, stomach cancer, pancreatic cancer, hepatobiliary cancer, cancer of the gallbladder, cancer of the small intestine, rectal cancer, kidney cancer, bladder cancer, prostate cancer, penile cancer, urethral cancer, testicular cancer, cervical cancer, vaginal cancer, uterine cancer, ovarian cancer, thyroid cancer, parathyroid cancer, adrenal cancer, pancreatic endocrine cancer, carcinoid cancer, bone cancer, skin cancer, retinoblastomas, multiple myelomas, Hodgkin's lymphoma, and non-Hodgkin's lymphoma (see, CANCER: PRINCIPLES AND PRACTICE (DeVita, V. T. et al. eds 2008) for additional cancers). In some embodiments, the disease is cancer.

Other diseases that can be treated by the nanocarriers of the present invention include: (I) inflammatory or allergic diseases such as systemic anaphylaxis or hypersensitivity responses, drug allergies, insect sting allergies; inflammatory bowel diseases, such as Crohn's disease, ulcerative colitis, ileitis and enteritis; vaginitis; psoriasis and inflammatory dermatoses such as dermatitis, eczema, atopic dermatitis, allergic contact dermatitis, urticaria; vasculitis; spondyloarthropathies; scleroderma; respiratory allergic diseases such as asthma, allergic rhinitis, hypersensitivity lung diseases, and the like, (2) autoimmune diseases, such as arthritis (rheumatoid and psoriatic), osteoarthritis, multiple sclerosis, systemic lupus erythematosus, diabetes mellitus, glomerulonephritis, and the like, (3) graft rejection (including allograft rejection and graft-v-host disease), and (4) other diseases in which undesired inflammatory responses are to be inhibited (e.g., atherosclerosis, myositis, neurological conditions such as stroke and closed-head injuries, neurodegenerative diseases, Alzheimer's disease, encephalitis, meningitis, osteoporosis, gout, hepatitis, nephritis, sepsis, sarcoidosis, conjunctivitis, otitis, chronic obstructive pulmonary disease, sinusitis and Behcet's syndrome). In some embodiments, the disease is asthma.

In addition, the nanocarriers of the present invention are useful for the treatment of infection by pathogens such as viruses, bacteria, fungi, and parasites. Other diseases can be treated using the nanocarriers of the present invention.

A. Formulations

The nanocarriers of the present invention can be formulated in a variety of different manners known to one of skill in the art. Pharmaceutically acceptable carriers are determined in part by the particular composition being administered, as well as by the particular method used to administer the composition. Accordingly, there are a wide variety of suitable formulations of pharmaceutical compositions of the present invention (see, e.g., *Remington's Pharmaceutical Sciences*, 20$^{th}$ ed., 2003, supra). Effective formulations include oral and nasal formulations, formulations for parenteral administration, and compositions formulated for with extended release.

Formulations suitable for oral administration can consist of (a) liquid solutions, such as an effective amount of a compound of the present invention suspended in diluents, such as water, saline or PEG 400; (b) capsules, sachets, depots or tablets, each containing a predetermined amount of the active ingredient, as liquids, solids, granules or gelatin; (c) suspensions in an appropriate liquid; (d) suitable emulsions; and (e) patches. The liquid solutions described above can be sterile solutions. The pharmaceutical forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents. Preferred pharmaceutical preparations can deliver the compounds of the invention in a sustained release formulation.

Pharmaceutical preparations useful in the present invention also include extended-release formulations. In some embodiments, extended-release formulations useful in the present invention are described in U.S. Pat. No. 6,699,508, which can be prepared according to U.S. Pat. No. 7,125,567, both patents incorporated herein by reference.

The pharmaceutical preparations are typically delivered to a mammal, including humans and non-human mammals. Non-human mammals treated using the present methods include domesticated animals (i.e., canine, feline, murine, rodentia, and lagomorpha) and agricultural animals (bovine, equine, ovine, porcine).

In practicing the methods of the present invention, the pharmaceutical compositions can be used alone, or in combination with other therapeutic or diagnostic agents.

B. Administration

The nanocarriers of the present invention can be administered as frequently as necessary, including hourly, daily, weekly or monthly. The compounds utilized in the pharmaceutical method of the invention are administered at the initial dosage of about 0.0001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. For example, dosages can be empirically determined considering the type and stage of disease diagnosed in a particular patient. The dose administered to a patient, in the context of the present invention should be sufficient to effect a beneficial therapeutic response in the patient over time. The size of the dose also will be determined by the existence, nature, and extent of any adverse side-effects that accompany the administration of a particular compound in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired. Doses can be given daily, or on alternate days, as determined by the treating physician. Doses can also be given on a regular or continuous basis over longer periods of time (weeks, months or years), such as through the use of a subdermal capsule, sachet or depot, or via a patch or pump.

The pharmaceutical compositions can be administered to the patient in a variety of ways, including topically, parenterally, intravenously, intradermally, subcutaneously, intramuscularly, colonically, rectally or intraperitoneally. Preferably, the pharmaceutical compositions are administered parenterally, topically, intravenously, intramuscularly, subcutaneously, orally, or nasally, such as via inhalation.

In practicing the methods of the present invention, the pharmaceutical compositions can be used alone, or in combination with other therapeutic or diagnostic agents. The additional drugs used in the combination protocols of the present invention can be administered separately or one or more of the drugs used in the combination protocols can be administered together, such as in an admixture. Where one or more drugs are administered separately, the timing and schedule of administration of each drug can vary. The other therapeutic or diagnostic agents can be administered at the same time as the compounds of the present invention, separately or at different times.

The nanocarriers of the present invention can be used to administer any suitable drug to a subject in need of treatment. In some embodiments, the present invention provides a method of delivering a drug to a subject in need thereof by administering a nanocarrier of the present invention to the subject, wherein the nanocarrier includes the drug and a plurality of cross-linked bonds. The method also includes cleaving the cross-linked bonds using a bond cleavage component, such that the drug is released from the nanocarrier, thereby delivering the drug to the subject. Any suitable bond cleavage component can be used, as described above.

VI. Method of Imaging

In some embodiments, the present invention provides a method of imaging, including administering to a subject to be imaged, an effective amount of a nanocarrier of the present invention, wherein the nanocarrier includes an imaging agent. In other embodiments, the method of treating and the method of imaging are accomplished simultaneously using a nanocarrier having both a drug and an imaging agent.

Exemplary imaging agents include paramagnetic agents, optical probes, and radionuclides. Paramagnetic agents imaging agents that are magnetic under an externally applied field. Examples of paramagnetic agents include, but are not limited to, iron particles including nanoparticles. Optical probes are fluorescent compounds that can be detected by excitation at one wavelength of radiation and detection at a second, different, wavelength of radiation. Optical probes useful in the present invention include, but are not limited to, Cy5.5, Alexa 680, Cy5, DiD (1,1'-dioctadecyl-3,3,3',3'-tetramethylindodicarbocyanine perchlorate) and DiR (1,1'-dioctadecyl-3,3,3',3'-tetramethylindotricarbocyanine iodide). Other optical probes include quantum dots. Radionuclides are elements that undergo radioactive decay. Radionuclides useful in the present invention include, but are not limited to, $^{3}H$, $^{11}C$, $^{13}N$, $^{18}F$, $^{19}F$, $^{60}Co$, $^{64}Cu$, $^{67}Cu$, $^{68}Ga$, $^{82}Rb$, $^{90}Sr$, $^{90}Y$, $^{99}Tc$, $^{99m}Tc$, $^{111}In$, $^{123}I$, $^{124}I$, $^{125}I$, $^{129}I$, $^{131}I$, $^{137}Cs$, $^{177}Lu$, $^{186}Re$, $^{188}Re$, $^{211}At$, $^{186}Re$, $^{188}Re$, $^{211}At$, Rn, Ra, Th, U, Pu and $^{241}Am$.

VII. Examples

Materials

Monomethylterminated poly(ethylene glycol) monoamine (MeO-PEG-NH$_2$, M$_w$: 5000 Da) was purchased from Rapp Polymere (Germany). PTX was purchased from AK Scientific Inc. (Mountain View, Calif.). Taxol® (Mayne Pharma, Paramus, N.J.) was obtained from the Cancer Center of University of California, Davis. Vincristine sulfate was purchased from AvaChem Scientific (San Antonio, Tex.). The conventional (clinical) formulation of vincristine sulfate was obtained from the Cancer Center of University of California, Davis. (Fmoc)lys(Boc)-OH, (Fmoc)Lys(Dde)-OH, (Fmoc)Lys(Fmoc)-OH, (Fmoc)Cys(Trt)-OH and (Fmoc)Ebes-OH were obtained from AnaSpec Inc. (San Jose, Calif.). 1,1'-dioctadecyl-3,3,3',3'-tetramethylindodicarboeyanine perchlorate (DiD), BODIPY650/665 and 4,6-cliamidino-2-phenylindole (DAPI, blue) were purchased from Invitrogen. Tetrazolium compound [3-(4,5-dimethylthiazol-2-yl)-5-(3 carboxymethoxyphenyl)-2-(4-sulfophenyl)-2H-tetrazolium, MTS] and phenazine methosulfate (PMS) were purchased from Promega (Madison, Wis.). Cholic acid, MTT [3-(4,5-dimethyldiazol-2-yl)-2,5 diphenyl tetrazolium bromide], Ellman's reagent [DTNB, 5,59-dithiobis(2-nitrobenzoic acid)] and all other chemicals were purchased from Sigma-Aldrich (St. Louis). Non-crosslinked micelle (NCM), disulfide crosslinked micelle (DCM) and boronate crosslinked micelle (BCM).

Animal Model

Female athymic nude mice (Nu/Nu strain), 6-8 weeks age, were purchased from Harlan (Livermore, Calif.). All animals were kept under pathogen-free conditions according to AAALAC guidelines and were allowed to acclimatize for at least 4 days prior to any experiments. All animal experiments were performed in compliance with institutional guidelines and according to protocol No. 07-13119 and No. 09-15584 approved by the Animal Use and Care Statistical Analysis Statistical analysis was performed by Student's t-test for two groups, and one-way ANOVA for multiple groups. All results were expressed as the mean±standard error (SEM) unless otherwise noted. A value of P<0.05 was considered statistically significant.

Example 1. Preparation of Thiolated Conjugate (PEG$^{5k}$-Cys$_4$-L$_8$-CA$_8$)

Figure 10:
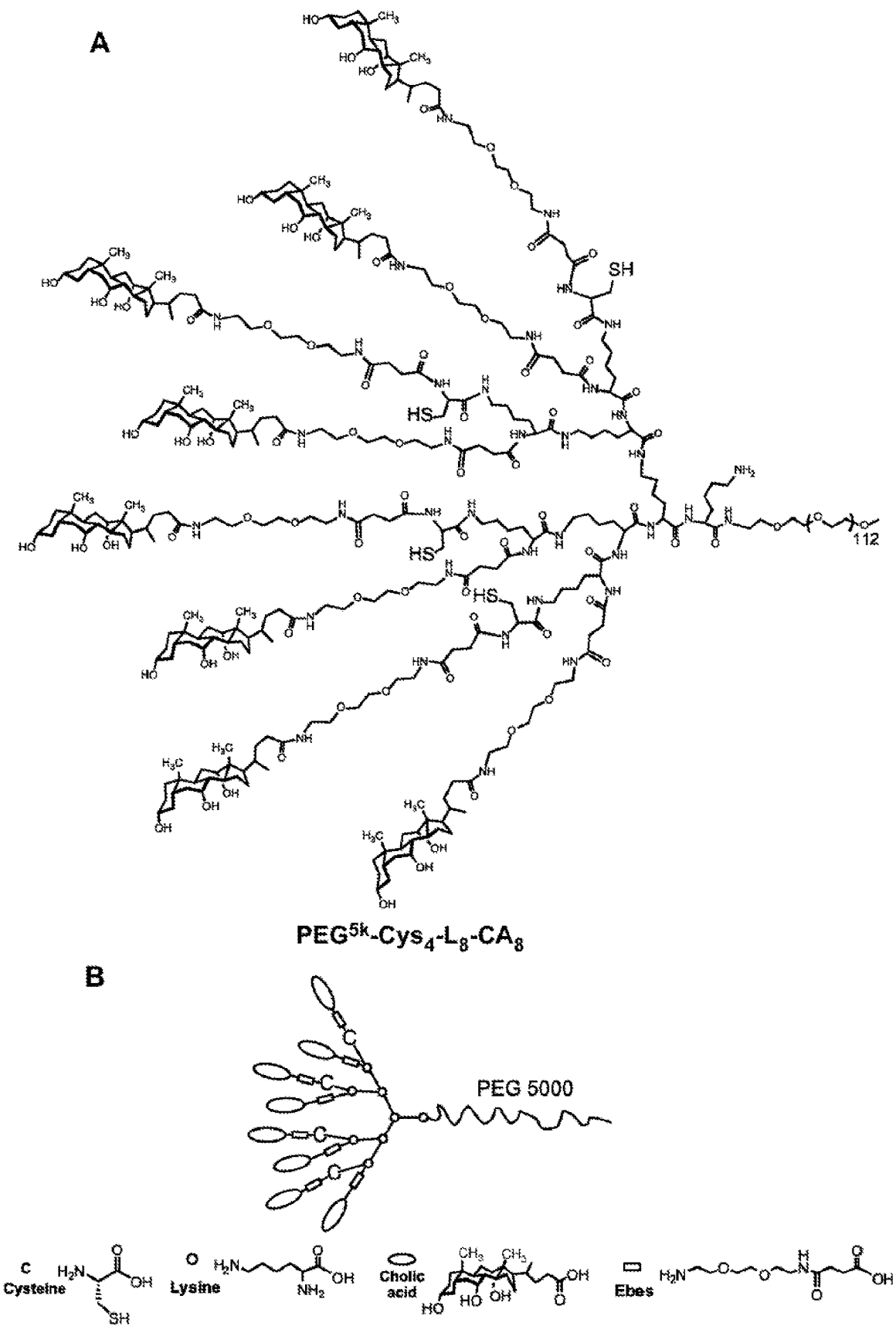
FIG. 10 shows the chemical structure (A) and schematic representation (B) of PEG$^{5k}$-Cys$_4$-L$_8$-CA$_8$.
Figure 11:
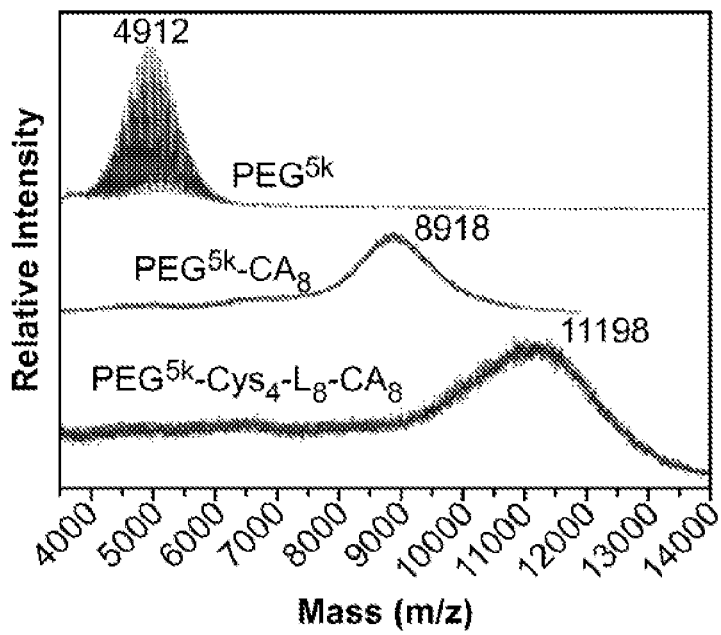
FIG. 11 shows the MALDI-TOF MS of PEG$^{5k}$-Cys$_4$-L$_4$-CA$_8$ telodendrimer comparing with the starting PEG 5000 and PEG$^{5k}$-CA$_8$ telodendrimer.
Figure 12:
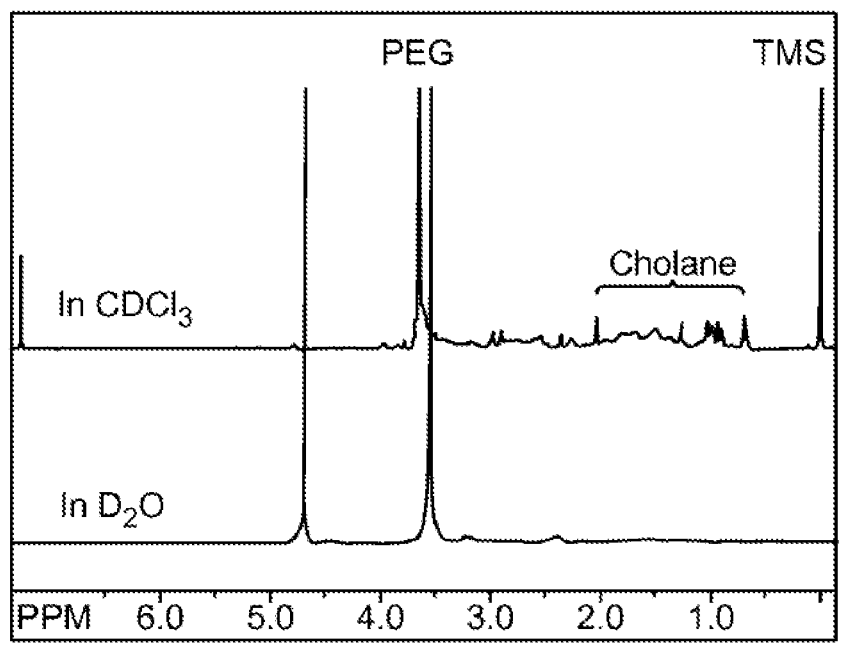
FIG. 12 shows NMR spectra of PEG$^{5k}$-Cys$_4$-L$_8$-CA$_8$ telodendrimer recorded in CDCl$_3$ and D$_2$O.

The thiolated telodendrimer (named as PEG$^{5k}$-Cys$_4$-L$_8$-CA$_8$) was synthesized via solution-phase condensation reactions from MeO-PEG-NH$_2$ utilizing stepwise peptide chemistry. The typical procedure for synthesis of PEG$^{5k}$-Cys$_4$-L$_8$-CA$_8$ was as follows: (Fmoc)Lys(Dde)-OH (3 eq.) was coupled onto the N terminus of PEG using DIC and HOBt as coupling reagents until a negative Kaiser test result was obtained, thereby indicating completion of the coupling reaction. PEGylated molecules were precipitated by adding cold ether and then washed with cold ether twice. Fmoc groups were removed by the treatment with 20% (v/v) 4-methylpiperidine in dimethylformamide (DMF), and the PEGylated molecules were precipitated and washed three times by cold ether. White powder precipitate was dried under vacuum and two coupling of (Fmoc)Lys(Fmoc)-OH and one coupling of (Fmoc)lys(Boc)-OH were carried out respectively to generate a third generation of dendritic polylysine terminated with four Boc and Fmoc groups on one end of PEG. After the removal of Boc groups with 50% (v/v) trifluoroacetic acid (TFA) in dichloromethane (DCM), (Fmoc)Cys(Trt)-OH, (Fmoc)Ebes-OH and Cholic acid NHS ester were coupled step by step to the terminal end of dendritic polylysine. The Trt groups on cysteines were removed by TFA/H2O/ethanedithiol (EDT)/triethylsilane (TIS) (94:2.5:2.5:1, v/v) resulting in PEG$^{5k}$-Cys$_4$-L$_8$-CA$_8$ thiolated telodendrimer (FIG. 10). The thiolated telodendrimer was recovered from the mixture by three cycles of dissolution/reprecipitation with DMF and ether, respectively. Finally, the thiolated telodendrimer was dissolved in acetonitrile/water and lyophilized. The PEG$^{5k}$-CA$_8$ thiol free telodendrimer was synthesized to prepare the non-cross-linked micelles according to our previously reported method. BODIPY650/665 (NIRF dye) labeled telodendrimers were synthesized by coupling BODIPY NHS ester to the amino group of the proximal lysine between PEG and cholic acid after the removal of 1-(4,4-dimethyl-2,6-dioxocyclohex-1-yldine)ethyl (Dde) protecting group by 2% (v/v) hydrazine in DMF.

Ellman's test was used to determine the number of cysteines conjugated to telodendrimers by free thiol groups. After adding Ellman reagents to a standard thiol (cysteine) for 15 min, a calibration curve was prepared by plotting the absorbance at 412 nm as function of cysteine concentrations. Based on the calibration curve, the number of cysteines on the telodendrimers was calculated from the absorbance of samples in Ellman's test. The mass spectra of the telodendrimers were collected on ABI 4700 MALDI TOF/TOF mass spectrometer (linear mode) using R-cyano-4-hydroxycinnamic acid as a matrix. $^1$H NMR spectra of the polymers were recorded on an Avance 500 Nuclear Magnetic Resonance Spectrometer using CDCl$_3$ and D$_2$O as solvents. The concentration of the polymers was kept at 5×10$^{-4}$ M for NMR measurements.

As determined by quantitative Ellman's test by using free cysteine to create a standard curve, the number of covalently attached cysteines in PEG$^{5k}$-Cys$_4$-L$_8$-CA$_8$ was 3.97, which was consistent with the molecular formula of the target telodendrimer. The molecular weight of PEG$^{5k}$-Cys$_4$-L$_8$-CA$_8$ was determined with MALDI-TOF Mass Spectrometry comparing with the starting PEG and PEG$^{5k}$-CA$_8$. The mono-dispersed mass traces were detected for the starting PEG and the telodendrimers, and the molecular weights of the telodendrimers from MALDI-TOF MS were almost identical to the theoretical value. The chemical shift of PEG chains (3.5-3.7 ppm) and cholic acid (0.6-2.4 ppm) could be observed in the $^1$H NMR spectra of the PEG$^{5k}$-Cys$_4$-L$_8$-CA$_8$ in CDCl$_3$. The integration of these peaks can be used to calculate the chemical compositions of the telodendrimers. The number of cholic acids determined by $^1$H-NMR for the telodendrimers was consistent with the molecular formula of the target telodendrimers. These results demonstrate the well-defined structure of telodendrimers. When the NMR spectrum of PEG$^{5k}$-Cys$_4$-L$_8$-CA$_8$ was recorded in D$_2$O, the cholic acid proton peaks were highly suppressed, indicating the entanglement of cholanes by the formation of core-shell micellar structure in the aqueous environment. The CMC of PEG$^{5k}$-CA$_8$ micelles and PEG$^{5k}$-Cys$_4$-L$_8$-CA$_8$ micelles before cross-linking were measured using pyrene as a hydrophobic fluorescent probe and found to be 5.53 μM and 5.96 μM, respectively. The PEG$^{5k}$-Cys$_4$-L$_8$-CA$_8$ micelles exhibited a size of 26 nm before cross-linking, which is also similar to PEG$^{5k}$-CA$_8$ micelles. These results indicate that PEG$^{5k}$-CA$_8$ micelles and PEG$^{5k}$-Cys$_4$-L$_8$-CA$_8$ micelles have similar physical properties.

Example 2. Preparation of Disulfide Cross-Linked Micelles 20 mg PEG$^{5k}$-Cys$_4$-L$_8$-CA$_8$ telodendrimer was dissolved in 1 mL phosphate buffered saline (PBS) to form micelles and then sonicated for 10 min. The thiol groups on the telodendrimer were oxidized to form disulfide linkages by purging oxygen into the micelle solution. The level of free thiol groups were monitored by Ellman's test over time. The micelle solution was used for further characterizations without dialysis after the level of free thiol groups remained at a constant low value.

Example 3. Preparation of PTX Loaded Disulfide Cross-Linked Micelles

Loaded with Paclitaxel

PTX was loaded into the micelles by the solvent evaporation method as described in our previous studies. Briefly, PTX (1, 2, 3, 5, 7.5, 9 mg) and PEG$^{5k}$-Cys$_4$-L$_8$-CA$_8$ telodendrimers (20 mg) were first dissolved in chloroform in a 10 mL round bottom flask. The chloroform was evaporated under vacuum to form a thin film. PBS buffer (1 mL) was added to re-hydrate the thin film, followed by 30 min of sonication. The PTX-loaded micelles were then cross-linked via O$_2$-mediated oxidization as described above. The amount of drug loaded in the micelles was analyzed on a HPLC system (Waters) after releasing the drugs from the micelles by adding 9 times of acetonitrile and 10 min sonication. The drug loading was calculated according to the calibration curve between the HPLC area values and concentrations of drug standard. The loading capacity is defined as the highest drug concentration that can be achieved by the micelles in aqueous solution while the loading efficiency is defined as the ratio of drug loaded into micelles to the initial drug content. One part of the PTX-loaded micelle solutions was stored at 4° C. for characterizations and the rest was lyophilized. The PTX loaded non-cross-linked micelles were prepared by using PEG$^{5k}$-CA$_8$ thiol free telodendrimer as reported previously.

Figure 1:
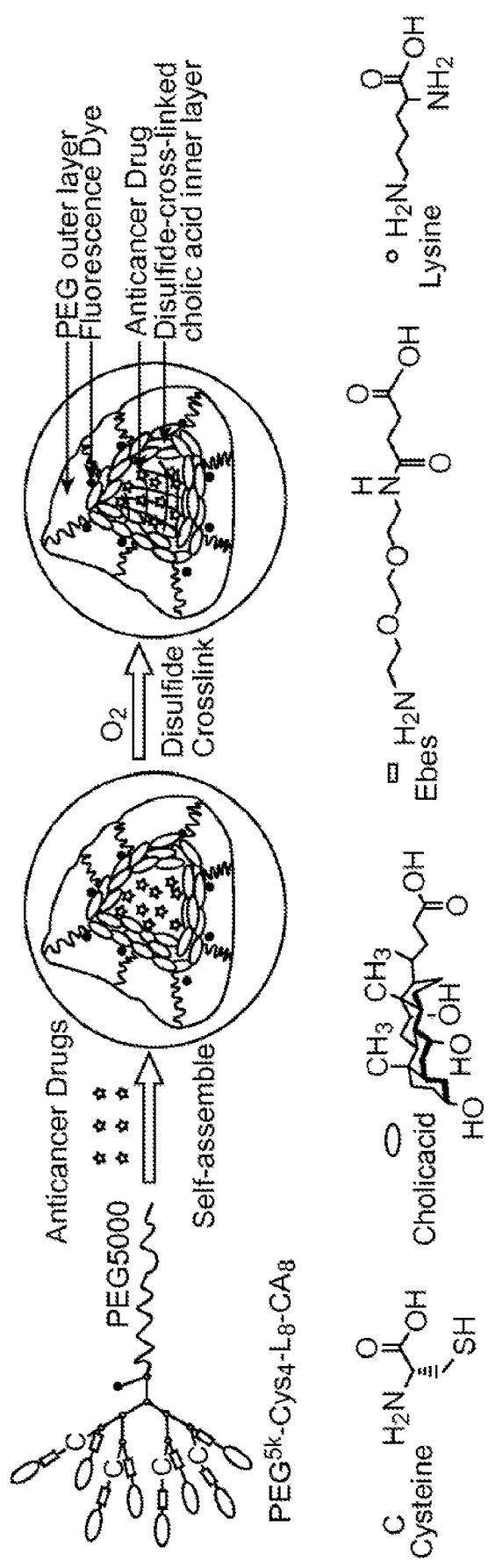
FIG. 1 shows a schematic presentation of the disulfide cross-linked micelles formed by oxidation of thiolated telodendrimer PEG$^{5k}$-Cys$_4$-L$_8$-CA$_8$ after self-assembly.
Figure 2:
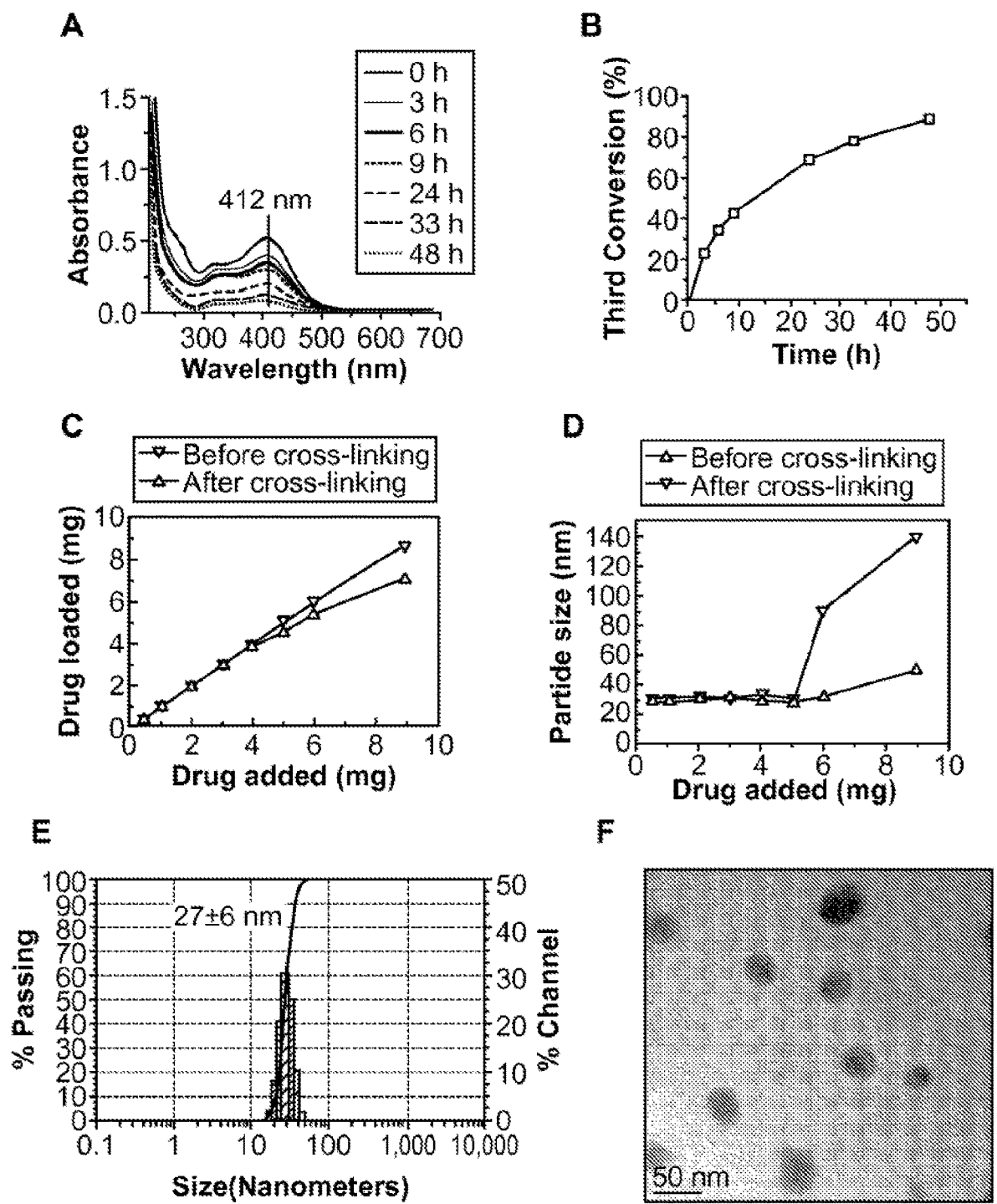
FIG. 2 shows the absorbance of PEG$^{5k}$-Cys$_4$-L$_8$-CA$_8$ micelle solutions in Ellman's test (A) and the thiol conversions (B) as a function of oxidation time. PTX loading (C) and size change (D) of PEG$^{5k}$-Cys$_4$-L$_8$-CA$_8$ micelle before and after cross-linking versus the level of drug added at initial loading. The volume of the final micelle solution was kept at 1 mL and the final concentration of the polymers at 20 mg/mL. DLS size distribution (E) and TEM image (F) of PTX-loaded cross-linked micelles (PTX loading was 4.6 mg/mL, TEM scale bar: 50 nm).

Before cross-linking, the PTX loading capacity in PEG$^{5k}$-Cys$_4$-L$_8$-CA$_8$ micelles was able to reach a level of 8.6 mg/mL (8.6 mg PTX loaded in 20 mg micelles in 1 mL PBS) (FIG. 2C). The loading efficiencies were almost 100% and the final particle sizes remained in the range of 25-50 nm (FIG. 2D) for all the loadings prior to cross-linking. After cross-linking via oxygen, the PTX loading capacity of the micelles decreased slightly from 8.6 mg/mL to 7.1 mg/mL, which is equivalent to 35.5% (w/w) of drug/micelle ratio (Table 1). It should be mentioned that the micelles retained the similar particle size and 100% PTX loading efficiency at a PTX loading of 5.0 mg/mL and lower after cross-linking. However, beyond 5.0 mg/mL, the particle sizes of the cross-linked micelles increased (FIG. 2D) while the loading efficiency decreased to 81%.

Loaded with 1,1'-dioctadecyl-3,3,3',3'-tetramethylindodicarbocyanine perchlorate (DiD)

DiD (hydrophobic NIRF dye) was loaded into the micelles using the same method as described above. The micelle solution was filtered with 0.22 μm filter to sterilize the sample.

Example 4. Characterization of PTX Loaded Disulfide Cross-Linked Micelles

General Characterization

The size and size distribution of the micelles were measured by dynamic light scattering (DLS) instruments (Microtrac). The micelle concentrations were kept at 1.0 mg/mL for DLS measurements. The zeta potential of these micelles was measured by DLS using the function of Zetatrac (Microtrac). All measurements were performed at 25° C., and data were analyzed by Microtrac FLEX Software 10.5.3. The morphology of micelles was observed on a Philips CM-120 transmission electron microscope (TEM). The aqueous micelle solution (1.0 mg/mL) was deposited onto copper grids, stained with phosphotungstic acid, and measured at room temperature. The critical micelle concentration (CMC) of the PEG$^{5k}$-CA$_8$ micelles and PEG$^{5k}$-Cys$_4$-L$_8$-CA$_8$ micelles before and after cross-linking was measured through fluorescence spectra by using pyrene as a hydrophobic fluorescent probe as described previously. Briefly, micelles were serially diluted in PBS to give the concentrations ranging from 5×10$^{-1}$ to 5×10$^{-4}$ M. The stock solution of pyrene in methanol was added into the micelle solution to make a final concentration of pyrene of 2×10$^{-6}$ M. The solution was mildly shaken over night. Excitation spectra were recorded ranging from 300 to 360 nm with a fixed emission at 390 nm. The ratios of the intensity at 337 to 332 nm from the excitation spectra of pyrene were plotted against the concentration of the micelles. The CMC was determined from the threshold concentration, where the intensity ratio 1337/1332 begins to increase markedly.

The PEG$^{5k}$-Cys$_4$-L$_8$-CA$_8$ micelles without drug loading (empty micelles) were further characterized with respect to particle size, apparent CMC and zeta potential following disulfide cross-linking. After the instant formation of micelles upon dispersion in aqueous solution, the free thiol groups of PEG$^{5k}$-Cys$_4$-L$_8$-CA$_8$ were oxidized by oxygen to form disulfide linkages. The O$_2$-mediated oxidization was monitored by Ellman's test. The free thiol groups were oxidized over time and more than 85% of thiol groups were reacted to form disulfide after 48 h of oxidation. Interestingly, the PEG$^{5k}$-Cys$_4$-L$_8$-CA$_8$ micelles retained a similar particle size of around 27 nm with the narrow distribution following disulfide cross-linking. This result suggests that the disulfide bond formation is an event that occurs within micelles. The PEG outer corona confines the cross-linking reaction intra-micellarly, preventing the formation of inter-micellar aggregates. After cross-linking, the apparent CMC of PEG$^{5k}$-Cys$_4$-L$_8$-CA$_8$ micelles decreased to 0.67 µM, which is 9 times lower than that of the non-cross-linked micelles. This observation for the cross-linked micelles is consistent with the reported cross-linked Pluronic L121 micelles. The zeta potential of the micelles was measured to be nearly neutral since these micelles were composed of uncharged PEG$^{5k}$-Cys$_4$-L$_8$-CA$_8$. PEG$^{5k}$-CA$_8$ micelles were selected as absolute non-cross-linked micelles (NCMs) in the following in vitro and in vivo evaluations, instead of the PEG$^{5k}$-Cys$_4$-L$_8$-CA$_8$ micelles prior to oxidation, because the latter will undoubtedly be partially cross-linked by oxygen in air upon storage. Furthermore, we want to directly compare the current cross-linked nanoformulation with our previously published non-cross-linked PEG$^{5k}$-CA$_8$ micelle.

TABLE 1

Physico-chemical properties of telodendrimers (PEG$^{5k}$-CA$_8$ and PEG$^{5k}$-Cys$_4$-L$_8$-CA$_8$) and the corresponding non-cross-linked and disulfide cross-linked micelles (NCMs and DCMs).

| Telodendrimers | Mw (theo.)[a] | Mw (MS)[b] | N$_{cysteines}$[c] | N$_{CA}$[d] | Micelles | CMC (µM)[f] | Size (nm)[g] | PTX loading capacity (mg/mL)[h] | Size with PTX (nm)[i] |
|---|---|---|---|---|---|---|---|---|---|
| PEG$^{5k}$-CA$_8$ | 9059 | 8918 | 0 | 7.5 | NCMs | 5.53 | 22 ± 5 | 9.0 | 26 ± 4 |
| PEG$^{5k}$-Cys$_4$-L$_8$-CA$_8$ | 11313 | 11198 | 3.97 | 7.3 | DCMs[e] | 0.67 | 28 ± 4 | 7.1 | 27 ± 6 |

[a]Theoretical molecular weight.
[b]Obtained via MALDI-TOF MS analysis (linear mode).
[c]Number of cysteines, obtained via Ellman's test.
[d]Number of cholic acids, calculated based on the average integration ratio of the peaks of methyl proton 18, 19, and 21 in cholic acid at 0.66, 0.87 and 1.01 ppm and methylene proton of PEG at 3.5-3.7 ppm in $^1$H-NMR spectra in CDCl$_3$. The molecular weight of the starting PEG was 4912.
[e]Formed by PEG$^{5k}$-Cys$_4$-L$_8$-CA$_8$ micelles after cross-linking.
[f]Measured via fluorescent method by using pyrene as a probe.
[g]Particle size of NCMs and DCMs, measured by dynamic light scattering particle sizer (Microtrac).
[h]PTX loading capacity of NCMs and DCMs, in the presence of 20 mg/mL of telodendrimers, measured by HPLC.
[i]Measured by dynamic light scattering particle sizer. The PTX loading of NCMs and DCMs was 5.0 mg/mL and 4.6 mg/mL, respectively.

Stability of Micelles in SDS and Human Plasma

The stability study was performed to monitor the change in particle size of the DCMs and NCMs in the presence of sodium dodecyl sulfate (SDS), which was reported to be able to efficiently break down polymeric micelles. An SDS solution (7.5 mg/mL) was added to aqueous solutions of micelles (1.5 mg/mL). The final SDS concentration was 2.5 mg/mL and the micelle concentration was kept at 1.0 mg/mL. The size and size distribution of the micelle solutions was monitored at predetermined time intervals. The stability of the micelles was also evaluated in the presence of GSH and NAC (20 mM) together with SDS. The lyophilized PTX-loaded micelle powder was re-hydrated with PBS and tested under the same conditions. At the end of the stability study, the samples were further observed under TEM. The stability of PTX-loaded NCMs and DCMs was further studied in 50% (v/v) plasma from healthy human volunteers. The mixture was incubated at physiological body temperature (37° C.) followed by size measurements at predetermined time intervals up to 96 h.

Figure 3:
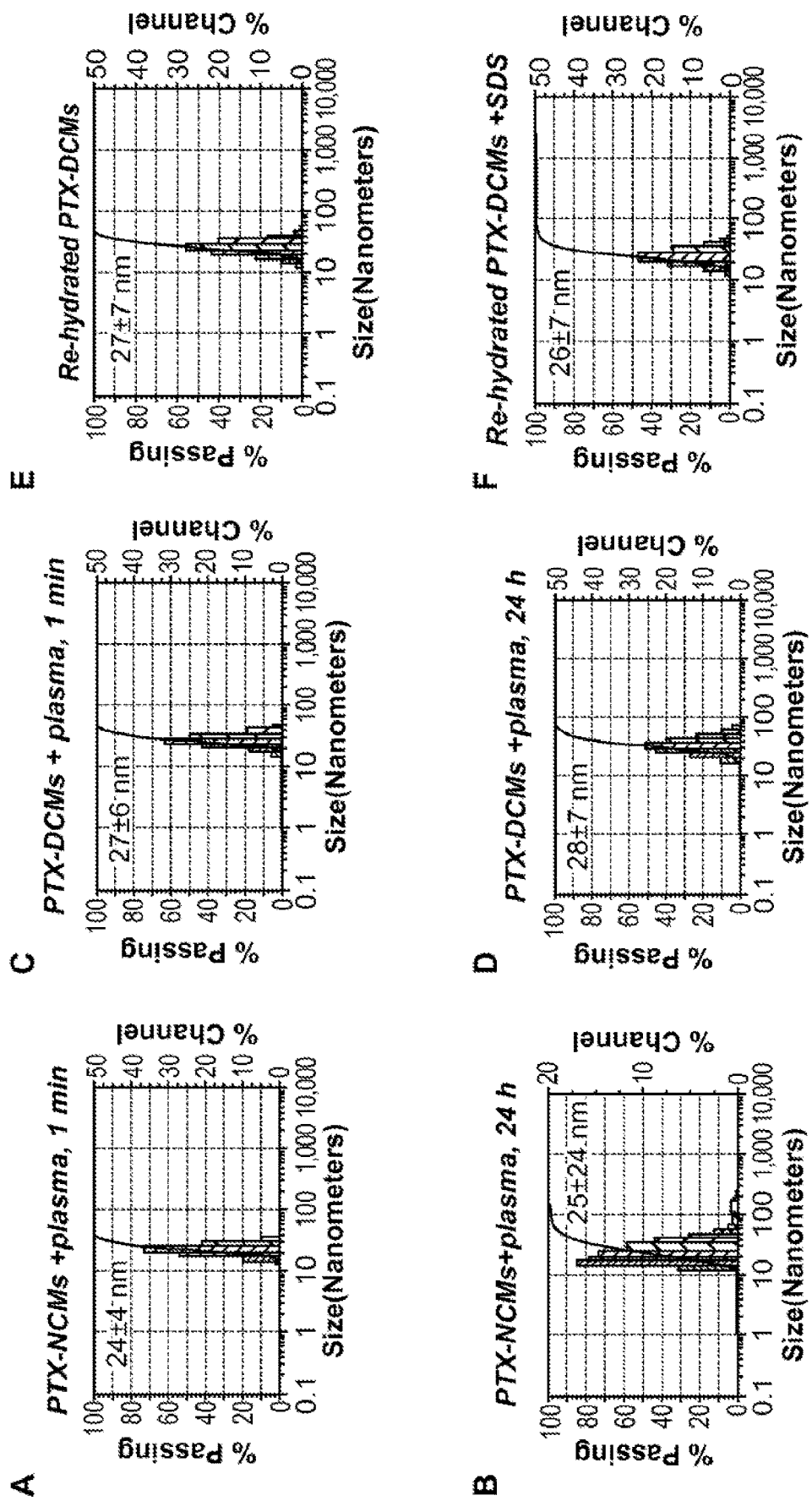
FIG. 3 shows the particle size of PTX loaded non-crosslinked micelles (NCMs) (PTX loading: 5.0 mg/mL) in human plasma 50% (v/v) for 1 min (A), 24 h (B) and PTX loaded disulfide crosslinked micelles (DCMs) (PTX loading: 4.6 mg/mL) in plasma 50% (v/v) for 1 min (C) and 24 h (D) at 37° C., respectively. The particle size of re-hydrated PTX-DCMs from lyophilized PTX-DCMs powder in the absence (E) and in the presence (F) of 2.5 mg/ml SDS.

Both PTX loaded non-cross-linked micelles (PTX-NCMs) and disulfide cross-linked micelles (PTX-DCMs) have been found to be stable at 4° C. The PTX-NCMs and PTX-DCMs were incubated with 50% human plasma, and the particle sizes of micelles were monitored by DLS over time. Both of the DCMs and NCMs micelles with similar PTX loading retained the average particle size around 30 nm in human plasma for 24 hours (FIG. 3). However, the PTX-DCMs still kept the uniformity and narrow distribution in size while the PTX-NCMs showed broader size distribution and population of size over 100 nm, indicating the formation of aggregates (FIG. 3).

Figure 4:
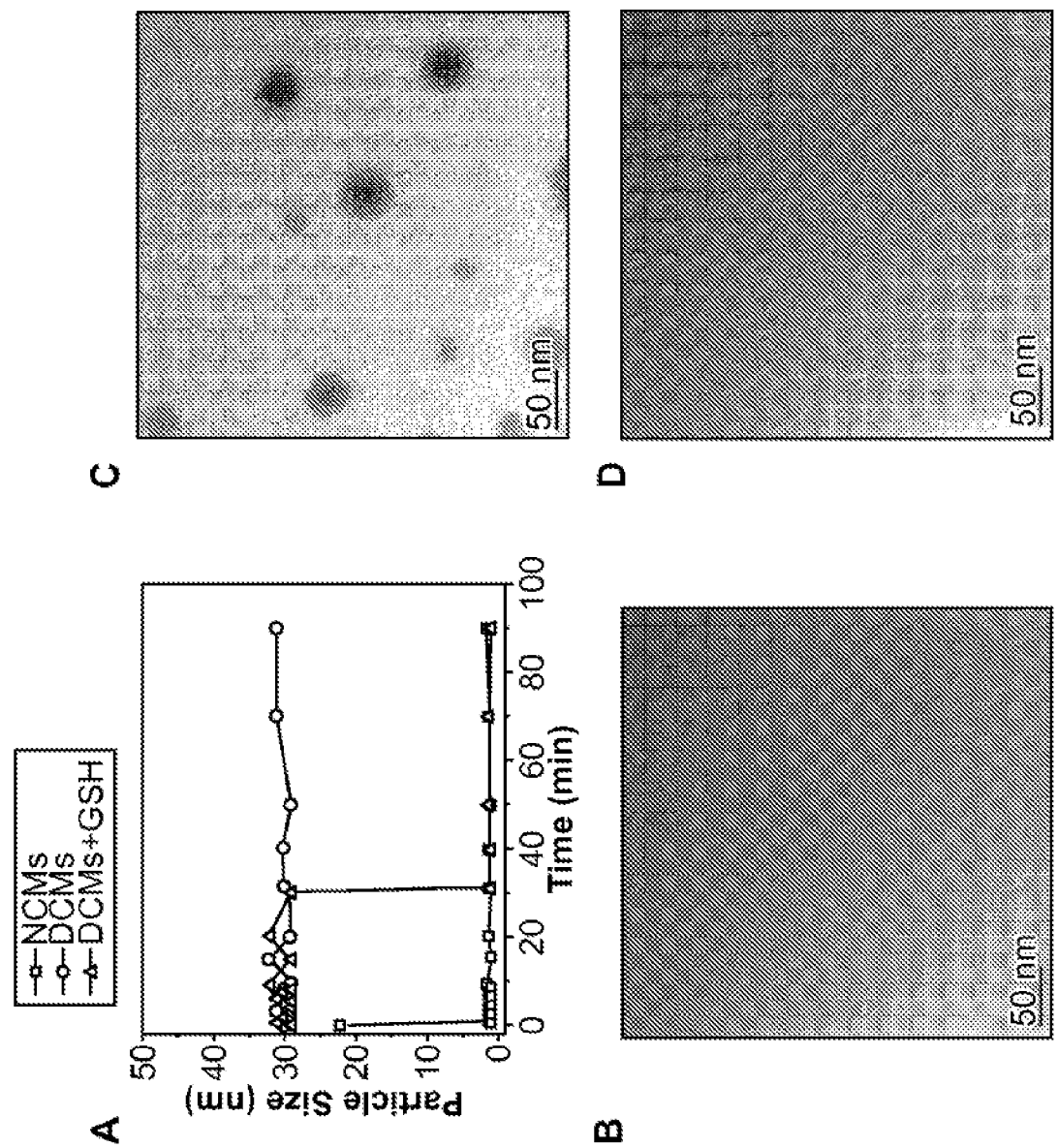
FIG. 4 shows (A) the stability in particle size of NCMs and DCMs in the presence of 2.5 mg/mL SDS measured by DLS. TEM images of NCMs (B), DCMs (C) and DCMs treated with 10 mM GSH for 30 mM (D) in the presence of 2.5 mg/mL SDS (scale bar: 50 nm).
Figure 13:
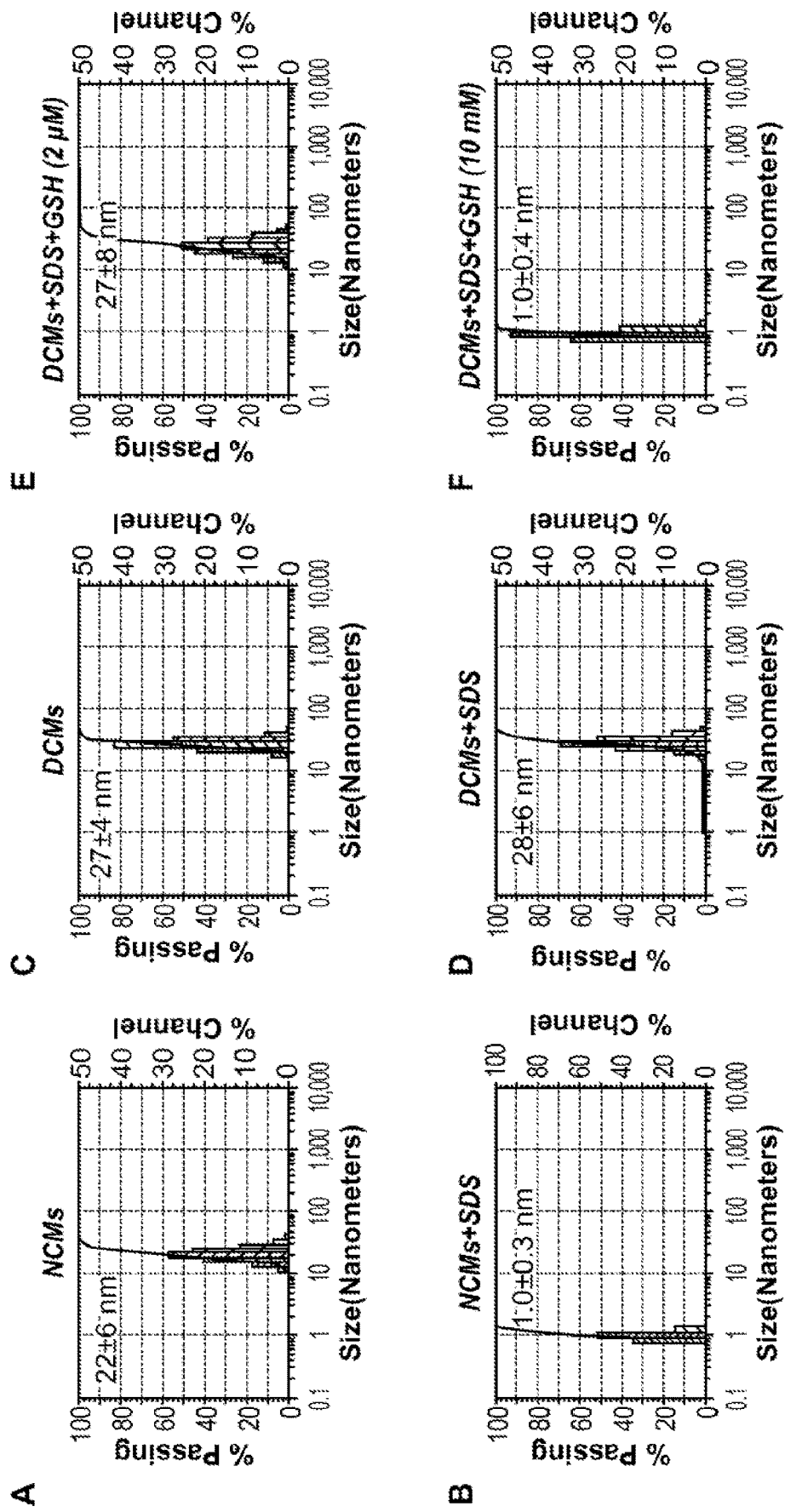
FIG. 13 shows the particle size of NCMs in the absence (A) and in the presence (B) of 2.5 mg/mL SDS for 10 sec. The particle size of DCMs in the absence (C) and in the presence of 2.5 mg/mL SDS (D), 2.5 mg/mL SDS+2 µM GSH (E), 2.5 mg/mL SDS+10 mM GSH (F) for 40 min. The particle size was measured by dynamic light scattering (Microtrac).

Sodium dodecyl sulfate (SDS), a strong ionic detergent, has been reported to be able to efficiently break down polymeric micelles. The exchange rate between polymeric micelles and unimers is accelerated by low concentrations of SDS while at higher concentrations, the presence of SDS micelles solubilize the amphiphilic block copolymers resulting in destabilization of the polymeric micelles. The stability of NCMs and DCMs was also tested in the presence of the reported micelle-disrupting SDS concentration of 2.5 mg/mL. The size of SDS background is below the detection limit of DLS analysis, showing a 0.9 nm population in the spectra. After each micelle solution (1.0 mg/mL) was mixed with an aqueous solution of SDS (2.5 mg/mL), the particle size was monitored at various time points. The immediate disappearance of particle size signal of the NCMs reflects the distinct dynamic association-dissociation property of non-cross-linked micelles (FIG. 4, FIGS. 13A & B). The constant particle size of the DCMs under similar condition over time indicated that such cross-linked micelles remained intact. The re-hydrated lyophilized PTX-DCMs also retained the particle size at around 26 nm in the presence of SDS (FIGS. 3E & F).

The GSH concentration inside cells (~10 mM) is known to be substantially higher than the extracellular level (~2 µM). As shown in FIG. 13E, the DCMs were stable in SDS solution with a cellular exterior level of GSH (~2 µM). However, in the presence of SDS and an intracellular reductive GSH level (10 mM), the disulfide cross-linked micelle particle size signal remained unchanged for 30 min until it decreased suddenly (within 10 sec), indicating that rapid dissociation of the micelle when a critical number of disulfide bonds were reduced (FIG. 4A, FIG. 13F). The responses of PTX-NCMs and PTX-DCMs to SDS and different levels of GSH were similar to those of empty NCMs and DCMs, respectively. We also found that N-acetyl cysteine (NAC) could efficiently cleave the disulfide bonds of the DCMs, as evidenced by the complete disappearance of particle size of DCMs after 40 min in the presence of SDS and NAC (10 mM) (data not shown). The samples of DCMs and NCMs were further examined by TEM at the end point of the stability study. It was further confirmed that the micellar structure of NCMs was destroyed in SDS solution (FIG. 4B). The TEM images also demonstrated the micellar structure of DCMs were well retained in the presence of SDS (FIG. 4C) but efficiently broken down in the presence of SDS and 10 mM of GSH (FIG. 4D).

Cell Uptake and MTT Assay

SKOV-3 ovarian cancer cells were seeded at a density of 50000 cells per well in eight-well tissue culture chamber slides (BD Biosciences, Bedford, Mass., USA), followed by 24 h of incubation in McCoy's 5a Medium containing 10% FBS. The medium was replaced, and DiD labeled micelles (100 µg/mL) were added to each well. After 30 min, 1 h, 2 h and 3 h, the cells were washed three times with PBS, fixed with 4% paraformaldehyde and the cell nuclei were stained with DAPI. The slides were mounted with cover slips and observed under confocal laser scanning microscope (Olympus, FV1000).

SKOV-3 cells were seeded in 96-well plates at a density of 10000 cells/well 24 h prior to the treatment. The cells were first treated with or without GSH-OEt (20 mM) for 2 h and then washed 3 times with PBS. Empty micelles and various formulations of PTX with different dilutions were added to the plate and then incubated for 2 h. The cells were washed with PBS and incubated for another 22 h in a humidified 37° C., 5% $CO_2$ incubator. MTT was added to each well and further incubated for 4 h. The absorbance at 570 nm and 660 nm was detected using a micro-plate ELISA reader (SpectraMax M2, Molecular Devices, USA). Untreated cells served as a control. Results were shown as the average cell viability [$(OD_{treat}-OD_{blank})/(OD_{control}-OD_{blank})\times 100\%$] of triplicate wells.

Figure 6:
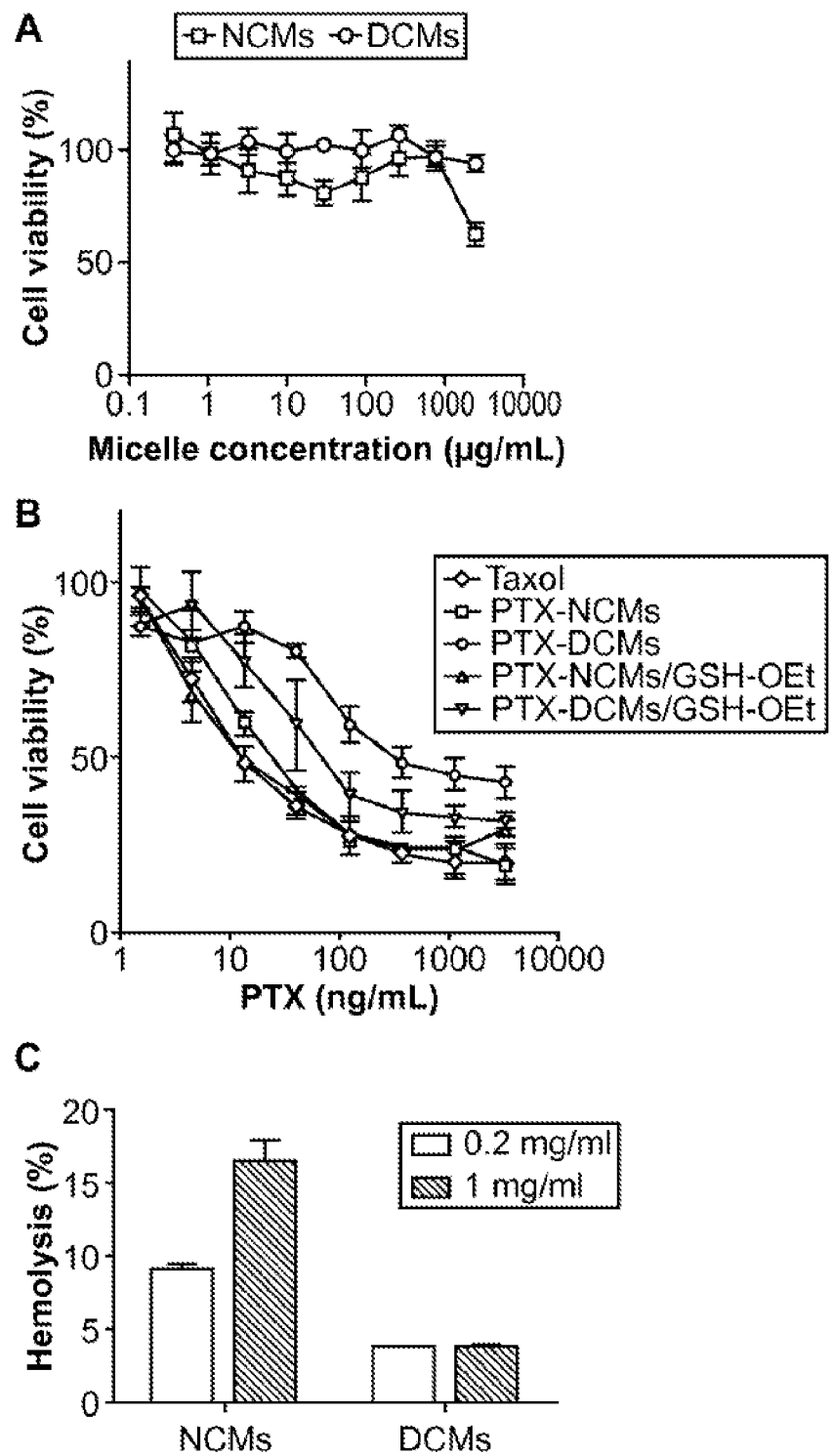
FIG. 6 shows MTT assays showing the viability of SKOV-3 cells after 2 h incubation with (A) different concentrations of empty NCMs and DCMs; and (B) Taxol®, PTX-NCMs and PTX-DCMs with and without pre-treatment of 20 mM GSH-OEt. (C) In vitro red blood cell (RBC) lysis of empty NCMs and DCMs. Values reported are the mean±SD for triplicate samples.

PTX-NCMs showed comparable in vitro anti-tumor effects against SKOV-3 cells as Taxol® (FIG. 6B). However, PTX-DCMs were found to be less cytotoxic than Taxol and PTX-NCMs, which was expected due to the slower release of PTX within the cell culture media as well as after the cellular uptake of PTX-DCMs (FIG. 6B). Pre-incubation of cells with GSH-OEt enhances the inhibition effect of PTX-DCMs when the concentration of PTX was higher than 10 ng/mL (FIG. 6B). In contrast, the toxicity profile of PTX-NCMs was not affected by the GSH-OEt pre-treatment. As described above, the addition of GSH-OEt increases the intracellular GSH concentration, and facilitates intracellular drug release because of the cleavage of intra-micellar disulfide bridges of DCMs, which results in enhanced cytotoxicity.

Hemolysis Assay

The hemolysis of NCMs and DCMs was investigated using fresh citrated blood from healthy human volunteers. The red blood cells (RBCs) were collected by centrifugation at 1000 rpm for 10 min, washed three times with PBS, and then brought to a final concentration of 2% in PBS. 200 µL of erythrocyte suspension was mixed with different concentrations (0.2 and 1.0 mg/mL) of NCMs and DCMs, respectively, and incubated for 4 h at 37° C. in an incubator shaker. The mixtures were centrifuged at 1000 rpm for 5 min, and 100 µL of supernatant of all samples was transferred to a 96-well plate. Free hemoglobin in the supernatant was measured by the absorbance at 540 nm using a micro-plate reader (SpectraMax M2, Molecular Devices, USA). RBC incubation with Triton-100 (2%) and PBS were used as the positive and negative controls, respectively. The percent hemolysis of RBCs was calculated using the following formula: RBCs hemolysis=$(OD_{sample}-OD_{negative\ control})/(OD_{positive\ control}-OD_{negative\ control})\times 100\%$.

As shown in FIG. 6C, empty NCMs were found to have dose dependent RBC lysis. The percentage of hemolysis increased from 9.0% to 16.3% with the increasing NCMs concentrations from 0.2 mg/mL to 1.0 mg/mL. In contrast, empty DCMs showed no observable hemolytic activities (<5%) in the RBCs at the same experimental concentrations. The intra-micellar disulfide bridges prevent DCMs from dissociation to form amphiphilic telodendrimers, thus minimizing the hemolytic activities.

In Vivo Blood Elimination Kinetics and Biodistribution

DiD or BODIPY labeled NCMs and DCMs were prepared for the blood elimination study. The concentration of BODIPY conjugated micelles was 5 mg/mL. The concentration of DiD loaded micelles was 20 mg/mL with DiD loading at 0.5 mg/mL. The fluorescence spectra of these fluorescently labeled micelles diluted 20 times by PBS were characterized by fluorescence spectrometry (SpectraMax M2, Molecular Devices, USA). 100 µL of BODIPY conjugated or DiD loaded NCMs and DCMs were injected into tumor free nude mice via tail vein. 50 µL blood was collected at different time points post-injection to measure the fluorescence signal of DiD or BODIPY.

Nude mice with subcutaneous SKOV-3 tumors of an approximate 8~10 mm diameter were subjected to in vivo NIRF optical imaging. At different time points post injection of DiD and PTX co-loaded cross-linked micelles (the concentrations of DiD and PTX were both 0.5 mg/mL), mice were scanned using a Kodak multimodal imaging system IS2000MM with an excitation bandpass filter at 625 nm and an emission at 700 nm. The mice were anaesthetized by intraperitoneal injection of pentobarbital (60 mg/kg) before each imaging. After in vivo imaging, animals were euthanized by $CO_2$ overdose at 24 h after injection. Tumors and major organs were excised and imaged with the Kodak imaging station.

Figure 7:
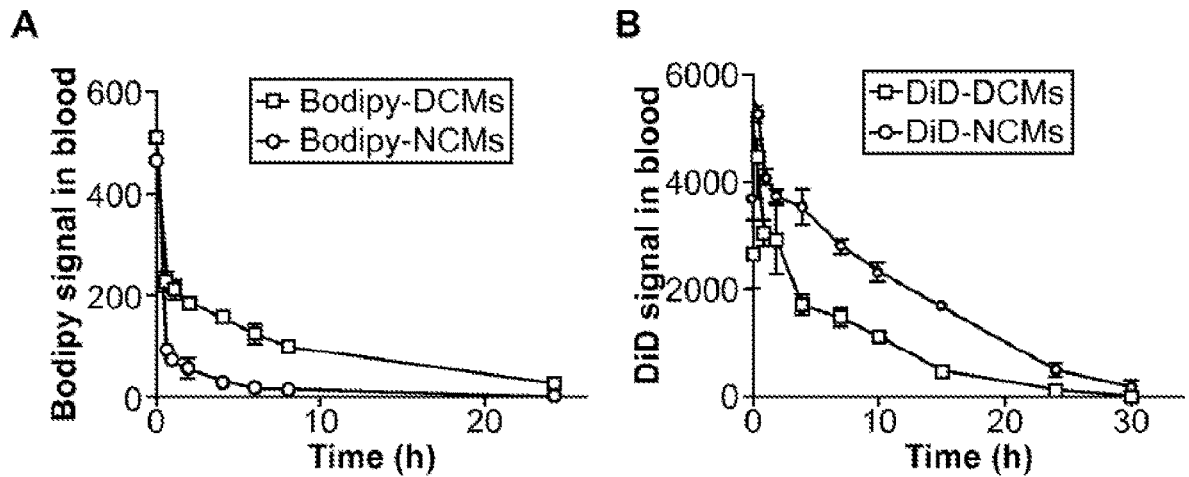
FIG. 7 shows the fluorescence signal of BODIPY labeled (A) and DiD loaded (B) DCMs and NCMs in the blood collected at different time points after i.v. injection in the nude mice.

The NIRF signal of blood background was found to be very low. DiD or BODIPY 6501665 labeled NCMs and DCMs had comparable in vitro near infrared fluorescence signals at an estimated in vivo concentration. After i.v. injection into mice, BODIPY signal of NCMs was rapidly eliminated from circulation and fell into the background level within 8 hours post injection. It should be mentioned that BODIPY signal of DCMs in blood was 8 times higher than that of NCMs at 8 hours post injection and sustained up to 24 hours (FIG. 7A). The overall micelle concentrations injected for DiD loaded NCMs or DCMs were 20 mg/mL, 4 times higher than that for BODIPY labeled NCMs or DCMs (5 mg/mL). Nevertheless, a similar trend of circulation kinetics was observed for the DiD loaded NCMs and DCMs. DiD signal of NCMs decreased faster in spite of the initial increase while that of the DCMs sustained in blood up to 30 h (FIG. 7B). The above profiles of elimination kinetics for both vehicle and payload indicated that the cross-linked micelles have longer blood circulation time than the non-cross-linked micelles.

Figure 8:
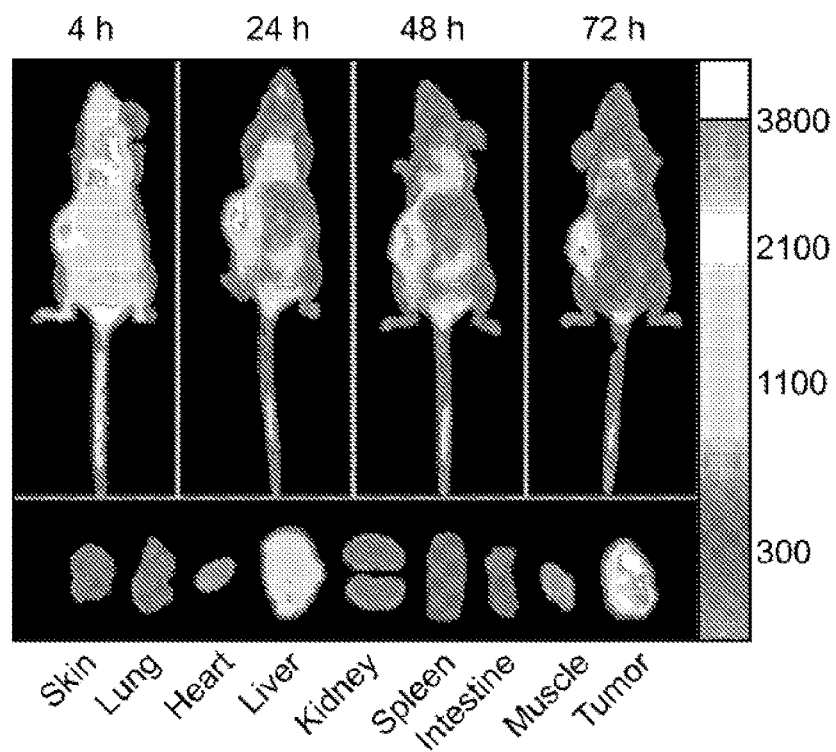
FIG. 8 shows in vivo and ex vivo near infra-red fluorescence (NIRF) optical imaging. Top: In vivo NIRF optical images of SKOV-3 xenograft bearing mouse were obtained with Kodak imaging system at different time points after i.v. injection of DCMs co-loaded with PTX and DiD; Bottom: Ex vivo NIR image of dissected organs and tumor was obtained at 72 h after injection.

Ex vivo imaging at 72 h post injection further confirmed the preferential uptake of DCMs in tumor compared to normal organs (FIG. 8). This is due to the prolonged in vivo circulation time of the micelles and the size-mediated EPR effect.

In Vivo Toxicity

In order to investigate for telodendrimer related toxicity, both empty non-cross-linked and cross-linked micelles were injected in tumor free nude mice at the single dose of 200 mg/kg and 400 mg/kg via tail vein. Mice were checked for possible signs of toxicity and the survival situation was monitored daily for two weeks.

At a single dose of 200 mg/kg, all the mice in NCMs group showed significant body weight loss and 1 of 4 mice died within 2 days post injection. All the mice in the group treated with a higher NCMs dose of 400 mg/kg died within 2 hours post injection. Bloody urine was observed for some mice, indicating the hemolytic potential caused by NCMs at high dosage. On the contrary, none of the mice treated with DCMs were dead at the single dose of 400 mg/kg and no obvious signs of toxicity were observed within two weeks post-injection.

Example 5. Drug Release from Disulfide Cross-Linked Micelle

PTX-loaded cross-linked micelle solution was prepared to determine the in vitro drug release profile. The initial PTX concentration was 4.6 mg/mL. Aliquots of PTX-loaded cross-linked micelle solution were injected into dialysis cartridges (Pierce Chemical Inc.) with a 3.5 kDa MWCO. The cartridges were dialyzed against 1 L PBS with various GSH concentrations (0, 2 µM, 1 mM, and 10 mM) at 37° C. In order to make an ideal sink condition, 10 g charcoal was added in the release medium. The concentration of PTX remaining in the dialysis cartridge at various time points was measured by HPLC. The drug release profiles of Taxol® and PTX loaded non-cross-linked micelles (PTX concentration: 5.0 mg/mL) were determined under identical condition for comparison. In some experiments, GSH or NAC (10 mM) were added to the release medium at a specific release time (5 h). The PTX release profiles of the lyophilized and rehydrated micelle solution were evaluated under the same conditions. Values were reported as the means for each triplicate sample.

Figure 5:
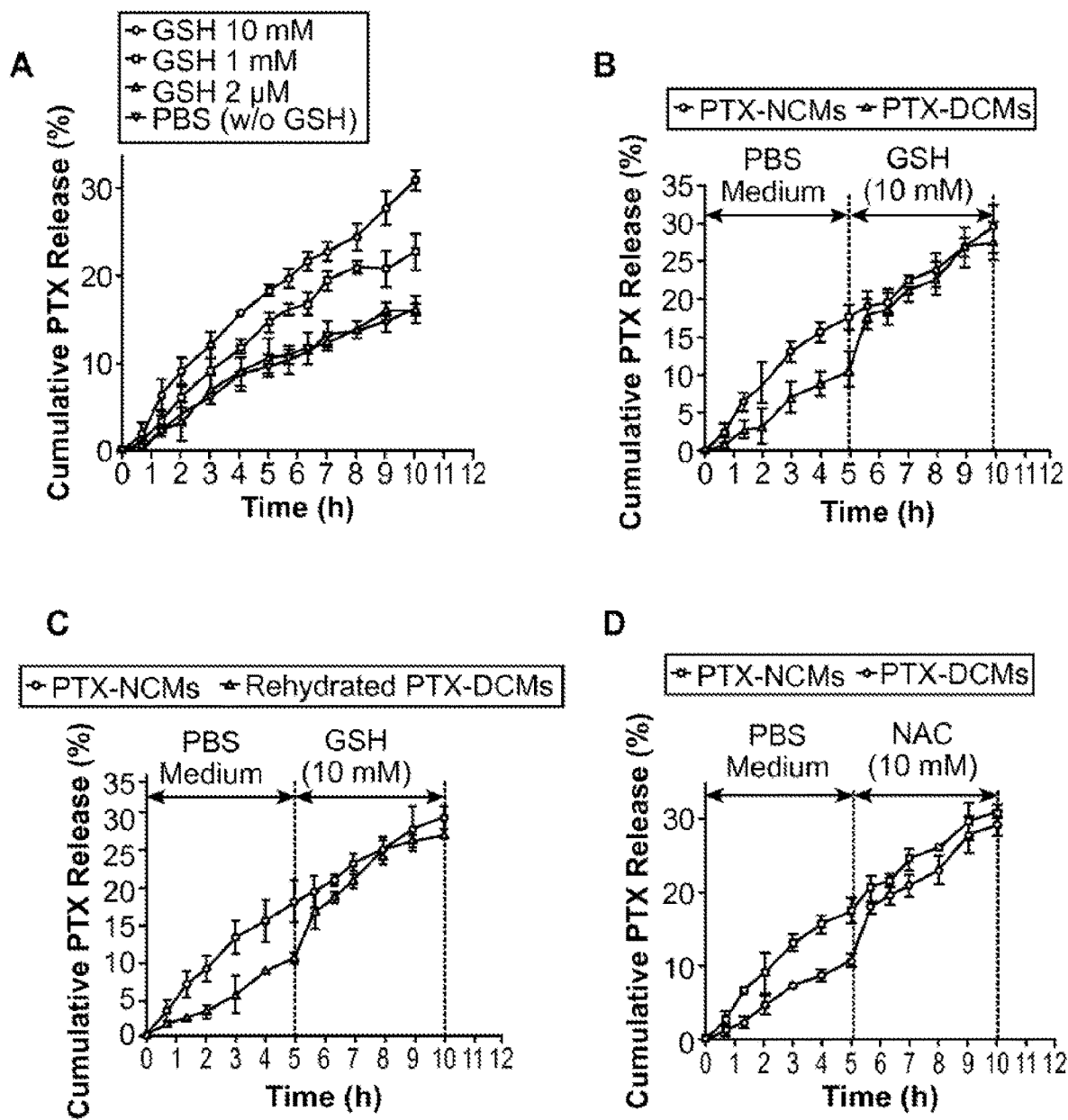
FIG. 5 shows (A) PTX release profiles of DCMs at different GSH concentrations. GSH-responsive PTX release profiles of fresh prepared PTX-DCMs (B) and re-hydrated lyophilized PTX-DCMs (C) by adding GSH (10 mM) at a specific release time (5 h) comparing with PTX-NCMs. NAC-responsive PTX release profiles of PTX-DCMs (D) by adding NAC (10 mM) at a specific release time (5 h). Values reported are the mean diameter±SD for triplicate samples.
Figure 14:
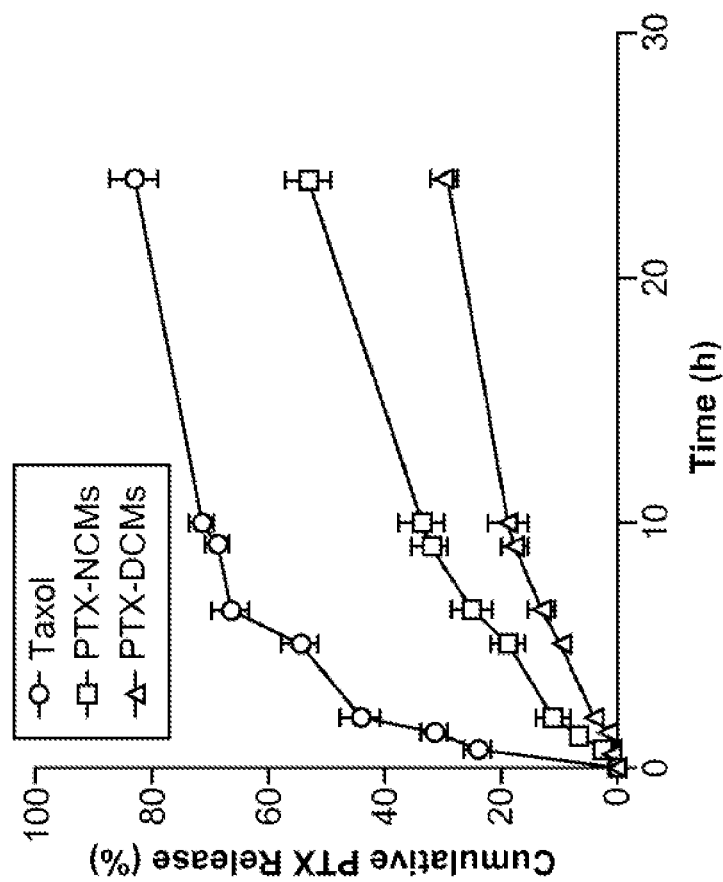
FIG. 14 shows cumulative PTX release profile from Taxol®, PTX loaded NCMs and DCMs.
Figure 15:
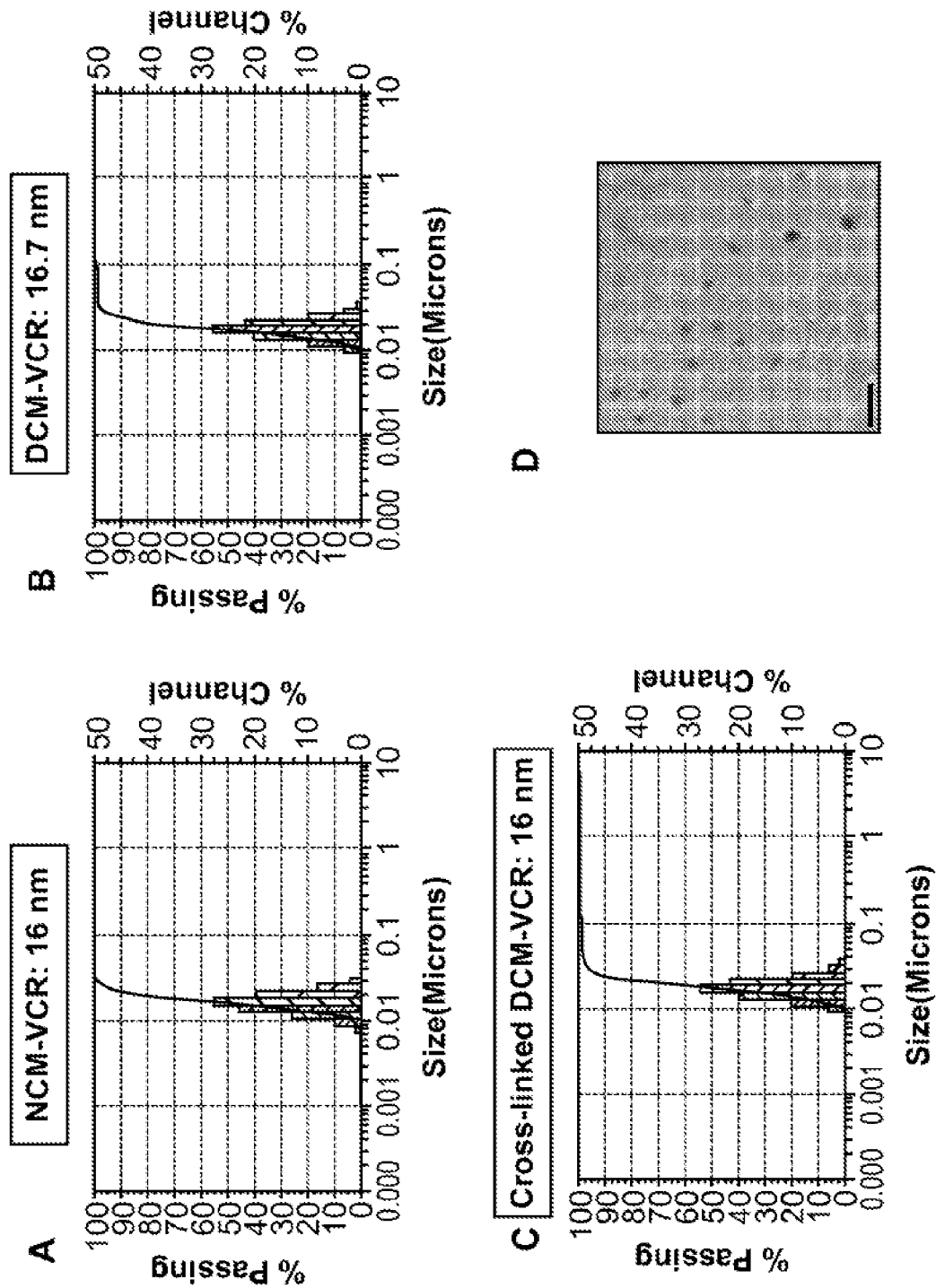
FIG. 15 shows particle size of NCM-VCR (A), DCM-VCR (B) and DCM-VCR after cross-linking (C). TEM image of DCM-VCR after cross-linking (D) (scale bar: 50 nm). Vincristine (VCR) loading was 20:1 telodendrimer to VCR (w/w).

The PTX release profiles from Taxol©, NCMs and DCMs were compared by using the dialysis method. PTX release from Taxol® was rapid and about 60% of PTX was released within the first 5 h. In contrast, PTX release from NCMs and DCMs was significantly slower (FIG. 14). In the presence of GSH at its extracellular level (2 µM), the PTX release profile from DCMs was similar to that in the release media without GSH. It was noted that the PTX release was gradually facilitated as the GSH concentration increased up to the intracellular level (10 mM) (FIG. 5A). This drug release study also indicated that PTX release from DCMs was significantly slower than that from NCMs (FIG. 14, FIG. 5B). When 10 mM GSH was added at the 5 h time point, there was a burst of drug release from the DCMs but not the NCMs (FIG. 5B). Subsequent release curves (after 6 h) of both preparations were identical (FIG. 5B). The PTX release profiles of the re-hydrated lyophilized PTX-DCMs were found to be very similar to the fresh sample and can be greatly facilitated by GSH (FIG. 5C). NAC, a FDA approved reducing agent, was demonstrated to have the same effect as GSH in triggering the PTX release from the disulfide cross-linked micelles (FIG. 5D). Therefore, NAC can be applied in vivo as an on-demand cleavage reagent via systemic i.v. injection to trigger drug release after nanotherapeutics have accumulated in tumor sites.

Example 6. Treatment of Ovarian Cancer with PTX Loaded Disulfide Cross-Linked Micelles Tumor Xenograft Model The subcutaneous xenograft model of ovarian cancer was established by injecting $7 \times 10^6$ SKOV-3 ovarian cells in a 100 µL of mixture of PBS and Matrigel (1:1 v/v) subcutaneously into the right flank of female nude mice.

In Vivo Therapeutic Study

Nude mice bearing SKOV-3 ovarian cancer xenografts were used to evaluate the therapeutic efficacy of the different formulations of PTX. The treatments were initiated when tumor xenograft reached a tumor volume of 100-200 $mm^3$ and this day was designated as day 0. On day 0, these mice were randomly divided into seven groups and injected intravenously via the tail vein with the formulations and repeated every 3 days for total 6 doses. Injection volume was 0.1 mL for each 10 g of mouse body weight. The seven groups (n=8-10) are shown in Table 1. Taxol® was given at a dose of 10 mg/kg which is close to its maximum tolerated dose (MTD). PTX loaded NCMs and DCMs were administered at the same PTX dose (10 mg/kg) for comparison. Because the micellar formulations of PTX are much more tolerated as we reported previously (MTD 75 mg/kg), The PTX loaded micelles were also administered at a higher dose (30 mg/kg) to determine if the anti-tumor effect could be enhanced. N-acetylcysteine (NAC) is a reducing agent and has been approved by FDA for mucolytic therapy (brand name: Mucomyst®) and the treatment of acetoaminophen overdose. In the seventh group, NAC was injected at a dose of 100 mg/kg into the mice via tail vein at 24 h after the administration of every dose of PTX loaded DCMs. Tumor size was measured with a digital caliper twice per week. Tumor volume was calculated by the formula $(L \times W^2)/2$, where L is the longest and W is the shortest in tumor diameters (mm). To compare between groups, relative tumor volume (RTV) was calculated at each measurement time point (where RTV equals the tumor volume at given time point divided by the tumor volume prior to initial treatment). To monitor potential toxicity, the body weight of each mouse was measured every 3 days. For humane reasons, animals were euthanized when the implanted tumor volume reached 1500 mm$^3$, which was considered as the end point of survival data.

Figure 9:
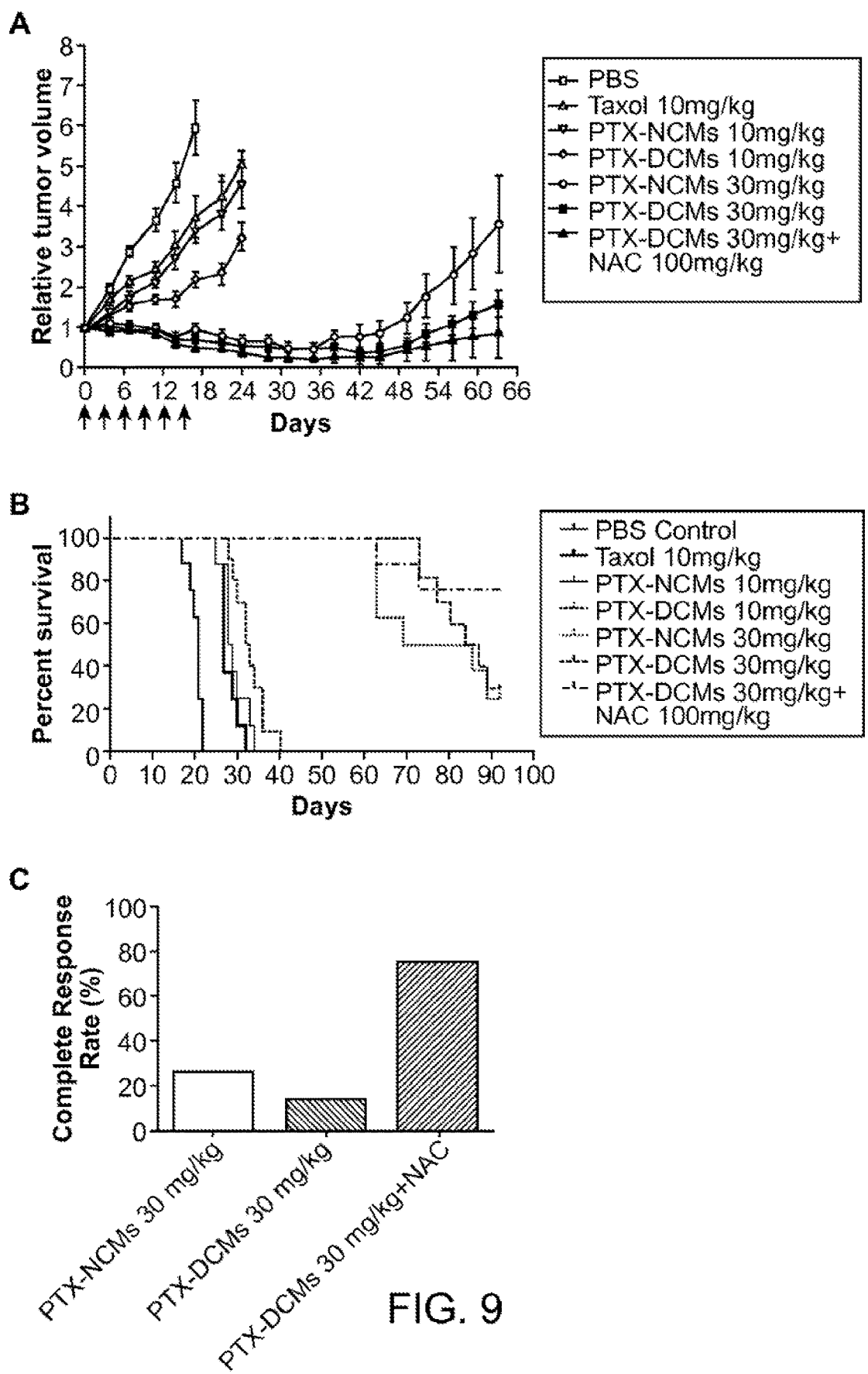
FIG. 9 shows (A) In vivo anti-tumor efficacy after intravenous treatment of different PTX formulations in the subcutaneous mouse model of SKOV-3 ovarian cancer. Tumor bearing mice were administered i.v. with PBS (control) and different PTX formulations on days 0, 3, 6, 9, 12 and 15 when tumor volume reached about 100~200 mm$^3$ (n=8-10). (B) Survival curve of mice in different treatment groups. (C) Complete tumor response rate of the three groups of mice treated with total six doses of PTX micellar formulations at the dose of 30 mg/kg.

The anti-tumor effects of PTX-DCMs and PTX-NCMs were evaluated in the subcutaneous SKOV-3 tumor bearing mice in comparison with the clinical formulation of PTX (Taxon. The seven groups (n=8-10) are shown in Table 1. The tumor growth inhibition and survival rate of SKOV-3 tumor bearing mice treated with PBS, Taxol®, PTX-NCMs, and PTX-DCMs were compared and the results are shown in FIG. 9. Compared with the control group, mice in all the treatment groups showed significant inhibition of tumor growth (P<0.05). However, at the dose of 10 mg PTX/kg (MTD of Taxol®), PTX-NCMs and PTX-DCMs exhibited superior tumor growth inhibition and longer survival time compared to Taxol®. The median survival time was 21 days for PBS, 27 days for 10 mg/kg Taxol®, 28.5 days for 10 mg/kg PTX-NCMs, and 32.5 days for 10 mg/kg PTX-DCMs, respectively. Importantly, the tumor growth rate of mice treated with 10 mg PTX/kg PTX-DCMs was lower compared to those treated with PTX-NCMs at 10 mg PTX/kg (P<0.05). PTX-DCMs showed increased in vivo therapeutic efficacy, regardless of their lower in vitro cytotoxicity against SKOV-3 cancer cells, which may due to the higher amount of PTX that reached the tumor site via their prolonged circulation time.

TABLE 2

Treatment groups of nude mice bearing SKOV-3 ovarian cancer xenografts.

| Group | Treatment[a] | Dose of PTX |
|---|---|---|
| 1 | PBS control | 0 |
| 2 | Taxol ® | 10 mg/kg |
| 3 | PTX-NCMs | 10 mg/kg |
| 4 | PTX-DCMs | 10 mg/kg |
| 5 | PTX-NCMs | 30 mg/kg |
| 6 | PTX-DCMs | 30 mg/kg |
| 7 | PTX-DCMs + NAC (100 mg/kg)[b] | 30 mg/kg |

[a]Administration started at the day when tumors reached a volume of 100-200 mm$^3$ and then every three days for six doses.
[b]In group 7, N-acetylcyseine (NAC) was administrated i.v. at a dose of 100 mg/kg 24 h after each dose of PTX-DCMs.

At the tumor site and particularly inside the tumor cells, the high glutathione level is expected to facilitate drug release from micelles and increase cytotoxicity. Three groups of mice were administrated at higher dose level: 30 mg PTX/kg PTX-NCMs, 30 mg PTX/kg PTX-DCMs and 30 mg PTX/kg PTX-DCMs followed by 100 mg/kg NAC 24 h later, respectively. It is important to realize that 30 mg/kg is more than double the maximum tolerated dose (MTD) for mice if it were given in the standard Cremophor EL/ethanol formulation of PTX (Taxol®). Tumor growth was inhibited in mice treated with all three micellar PTX formulations at 30 mg PTX/kg (FIG. 9A). The median relative tumor volume (RTV) for all the three high dose groups was less than 1.0 before day 36. However, tumor progression was subsequently noted for all these high dose groups. PTX-DCMs were demonstrated to be more efficacious in tumor inhibition than PTX-NCMs after day 36. It should be noted that the treatment of 30 mg PTX/kg PTX-DCMs followed with 100 mg/kg of NAC was efficacious for inhibiting tumor growth. No palpable tumors were detected in 6 of the 8 mice by day 93. The highest complete tumor response rate of 75% was achieved with the combination treatment of PTX-DCMs and NAC (FIG. 9C). NAC is commonly used in clinic as a reducing agent and has been approved by FDA for mucolytic therapy and for the treatment of acetoaminophen overdose. NAC has also been employed with a number of chemotherapy agents (e.g. cisplatin, carboplatin) as a means of reducing systemic toxicity. However, in some cases, the administration of NAC also reduced the therapeutic efficacy of these chemotherapy agents. In this study, the treatment of 30 mg PTX/kg PTX-DCMs followed by 100 mg/kg NAC exhibited a better anti-tumor effect than the treatment without NAC. This result indicated that NAC mainly played the role of a reducing agent when administered 24 hours after nanotherapeutic treatment to cleave the intra-micellar disulfide bridges and release the drug on-demand. This important in vivo observation has great translational potential and can be easily tested in clinical trials in the future.

Toxicities were assessed by analyzing effects on animal behavior and body weight change. The group of mice treated with 10 mg PTX/kg Taxol® frequently demonstrated decreased overall activity over 10 min post injection. This is likely due to the use of Cremophor EL and ethanol as vehicle for paclitaxel and the rapid high peak level of PTX in the blood. No noticeable change in activity was observed after administration of 10 mg PTX/kg PTX-NCMs and 10 mg PTX/kg PTX-DCMs. The group of mice receiving 30 mg PTX/kg PTX-DCMs followed with 100 mg/kg of NAC exhibited slight more body weight loss (12.2%) during the treatment cycle compared to other micellar PTX groups. Without being bound to any particular theory, one possible reason is the injection of high dose NAC. On the other hand, there may be still a small portion of PTX-DCMs in the blood circulation at 24 h post-injection. The administration of NAC may trigger the release of drug from circulating PTX-DCMs into blood stream, therefore resulting in toxicity to the mice. The systemic toxicity can probably be minimized by optimizing the dose and injection time of NAC.

Example 7. Preparation of Vincristine Loaded Disulfide Cross-Linked Micelles 1 mg of vincristine sulfate powder was dissolved with 3 molar equivalents of triethylamine (TEA) in chloroform and mixed with 20 mg PEG$^{5k}$-Cys$_4$-L$_8$-CA$_8$ telodendrimers in a 10 mL round bottom flask. Chloroform was evaporated under vacuum to form a thin film followed by hydration of the film with 1 mL PBS buffer and 30 min of sonication. The VCR-loaded micelles were then cross-linked via O$_2$-mediated oxidation as described above. 1 mg of vincristine sulfate powder was dissolved with 3 molar equivalents of triethylamine (TEA) in chloroform and mixed with 20 mg PEG$^{5h}$-Cys$_4$-L$_8$-CA$_8$ telodendrimers in a 10 mL round bottom flask. Chloroform was evaporated under vacuum to form a thin film followed by hydration of the film with 1 mL PBS buffer and 30 min of sonication. The VCR-loaded micelles were then cross-linked via O$_2$-mediated oxidation as described previously. The level of free thiol groups was monitored by Ellman's test over time.

Example 8. Characterization of Vincristine Loaded Disulfide Cross-Linked Micelles Characterization of the vincristine loaded disulfide cross-linked micelles was carried out using the methods described above, except where otherwise indicated.

Stability

Figure 16:
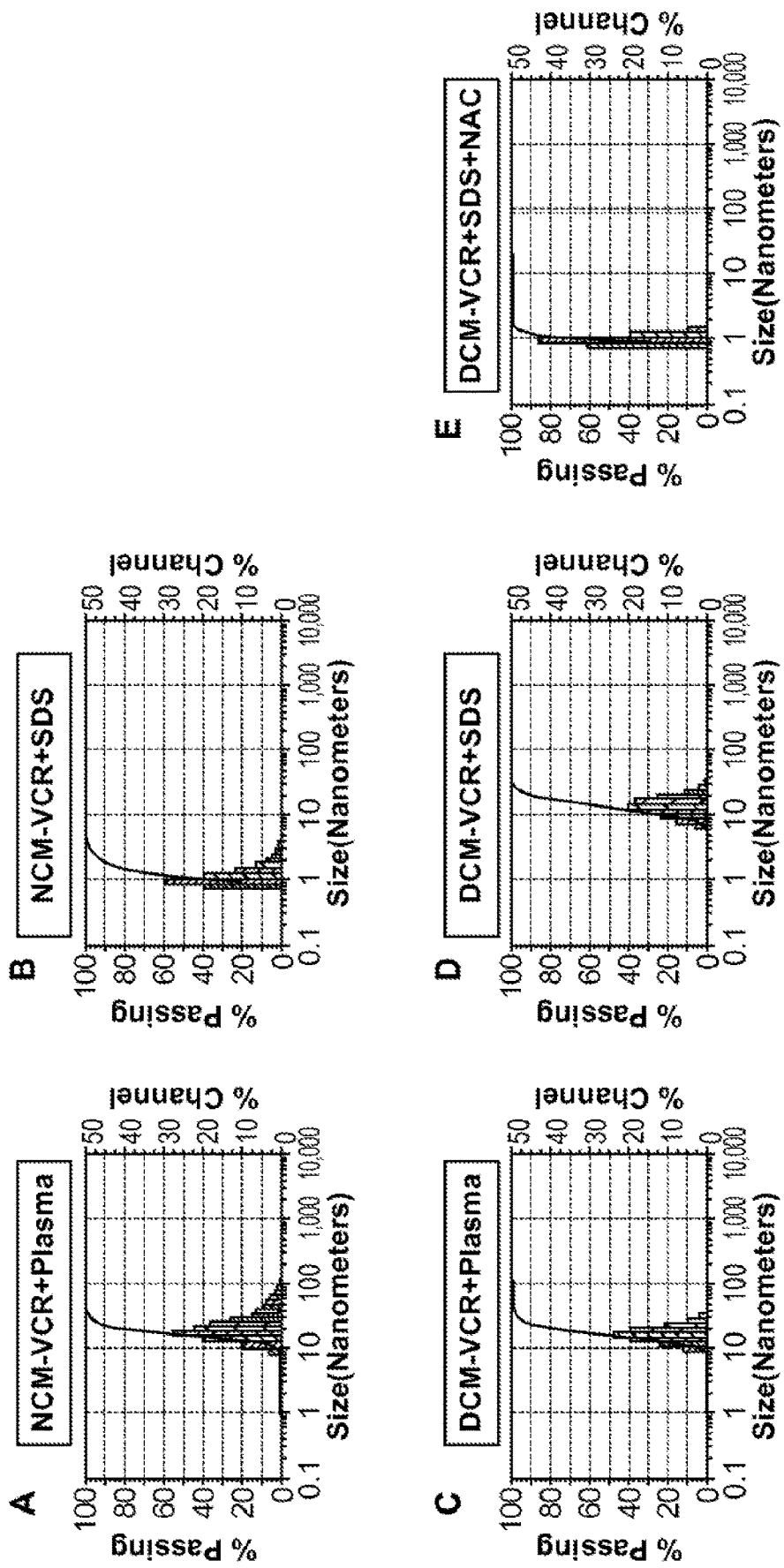
FIG. 16 shows particle size of NCM-VCR and DCM-VCR under micelle disrupting conditions. NCM-VCR (A) and DCM-VCR (C) were incubated in 50% human plasma (v/v) for 24 h at 37° C. Additionally, NCM-VCR (B) and DCM-VCR (D) were diluted to 2 mg/mL and incubated with 2.5 mg/mL SDS for 30 min. DCM-VCR (E) was incubated with both SDS and 20 mM N-acetylcysteine (NAC).
Figure 17:
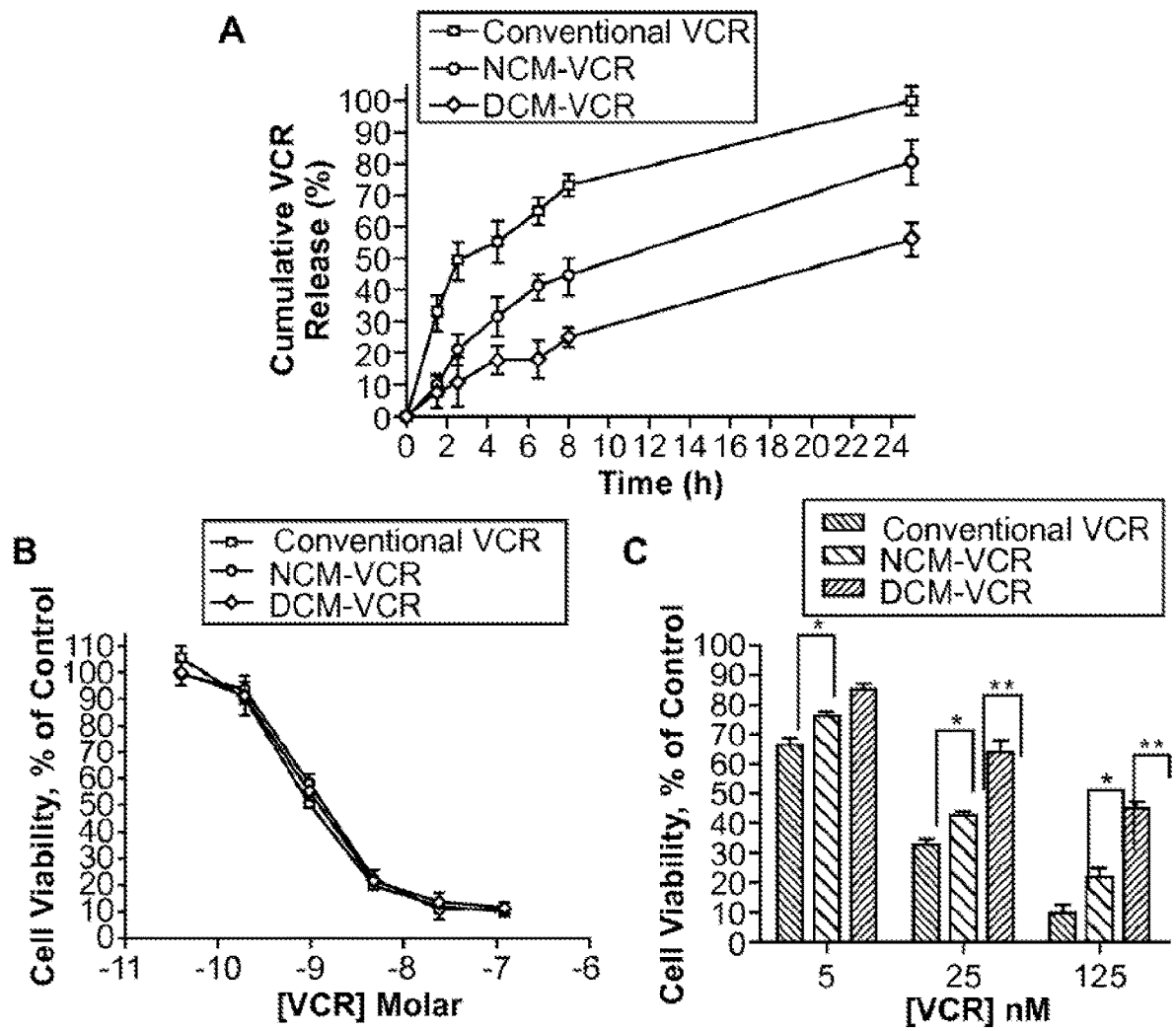
FIG. 17 shows drug release profile of conventional VCR, NCM-VCR and DCM-VCR (A). VCR formulations were dialyzed against 1 L PBS at 37° C. in the presence of 10 g/L charcoal to maintain sink conditions. The in vitro cytotoxicity of conventional VCR, NCM-VCR and DCM-VCR was assessed in Raji cells treated for 72 h continuously (B) or 2 h, washed and then incubated for 70 h (C). Cell viability was measured using an MTS assay. *, p<0.05; **, p<0.005.
Figure 18:
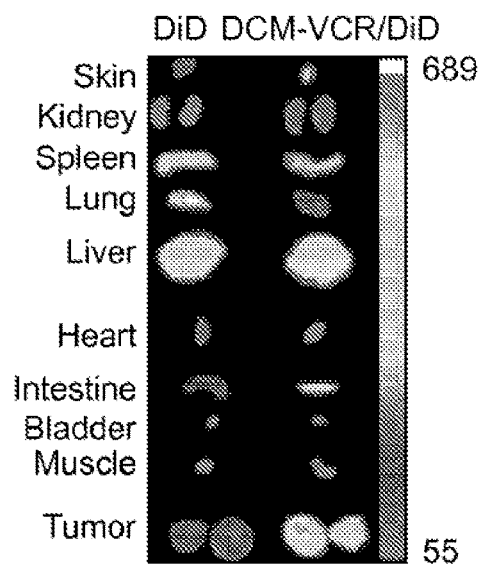
FIG. 18 shows ex vivo near-infrared optical imaging of Raji tumor bearing mice intravenously injected with free DiD or DCM co-loaded with VCR and DiD (DCM-VCR/DiD). 72 h post injection, tumors and major organs were excised and imaged using an excitation/emission filter of 625/700 nm.

The stability of NCM-VCR and DCM-VCR in physiological and severe micelle disrupting conditions was compared. Both types of micelles were incubated with 50% human plasma at 37° C. and their size was monitored over time using DLS. After 24 h, the size of NCM-VCR increased slightly from 16 to 31 nm and the particle size distribution was broadened with some particles as large as 100 nm (FIG. 16A). In comparison, the size of DCM-VCR was unchanged during the 24 h period (FIG. 16C). To further examine micelle stability, we monitored particle size after incubating NCM-VCR and DCM-VCR with 2.5 mg/mL SDS which is known to efficiently break down polymeric micelles. Immediately upon addition of SDS to NCM-VCR, micelle size was reduced from 15 to 1 nm, indicating complete micelle disruption (FIG. 16B). DCM-VCR resisted micelle disruption and maintained particle size (FIG. 16D). The intramicellar disulfide bonds which stabilize DCM-VCR are reversible which allows for drug release when inside the highly reducing environment of the target cell or upon external addition of a reducing agent such as N-acetylcysteine (NAC). In the presence of SDS and NAC (20 mM), the integrity of DCM-VCR was compromised and full disruption of the particle was observed after 1 h (FIG. 16E).

Drug Release

The in vitro drug release profiles for the different formulations of VCR were measured using the dialysis method. NCMs and DCMs were prepared with 20 mg/mL telodendrimer and loaded with 1 mg/mL VCR. Aliquots of the conventional formulation of VCR (1 mg/mL), NCM-VCR and DCM-VCR were injected into dialysis cartridges with a molecular-weight cutoff (MWCO) of 3.5 kDa (Thermo Scientific, Rockford, Ill.). Cartridges were dialyzed against 1 L PBS at 37° C. with shaking at 100 rpm in the presence of 10 g/L activated charcoal to create a sink condition. The concentration of VCR remaining in the dialysis cartridge at various time points was measured by spectrophotometry after releasing the drug from the micelles by adding 9 volumes of DMSO and 10 minutes of sonication. Values were reported as the means for each triplicate sample.

After 8 h, the conventional VCR sample had released 73% VCR compared to 44% and 24% for NCM-VCR and DCM-VCR, respectively. By 24 h, almost 100% of the conventional VCR had been released while NCM-VCR and DCM-VCR retained 20% and 43% of their original VCR content. We have previously demonstrated that when a reducing agent such as NAC or glutathione (GSH) is added to the dialysate, drug release can be rapidly facilitated.

In Vitro Toxicity

Raji cells were seeded in 96-well plates at a density of 10,000 cells/well. The cells were treated with the conventional formulation of VCR, NCM-VCR and DCM-VCR continuously for 72 h. In a separate experiment, Raji cells were incubated with the VCR formulations for 2 h, washed 3 times with PBS, resuspended in media and incubated for an additional 70 h. After 72 h, cell viability was assessed using the CellTiter 96 AQueous One Solution Cell Proliferation Assay according to the manufacturer's instructions. MTS solution (20 μL) was added to each well and cell viability assessed after a 1 h incubation. Cell viability as a percent of the untreated control for triplicate wells was calculated as follows: [($OD_{490}$ treated−$OD_{490}$ background)/($OD_{490}$ control−$OD_{490}$ background)*100].

Between the two VCR micelle formulations, NCM-VCR was more cytotoxic than DCM-VCR. Conventional VCR at a concentration of 25 nM killed 68% of cells while the same concentration of NCM-VCR and DCM-VCR killed 58% and 36% of cells, respectively.

Example 9. Treatment of B-Cell Lymphoma with Vincristine Loaded Disulfide Cross-Linked Micelles Xenograft Model The Burkitt's B-cell lymphoma cell line, Raji, was purchased from the American Type Culture Collection (ATCC; Manassas, Va., USA). Cells were cultured in ATCC formulated RPMI-1640 medium supplemented with 10% fetal bovine serum (FBS), 100 U/mL penicillin G and 100 μg/mL streptomycin at 37° C. using a humidified 5% $CO_2$ incubator. 3 days before tumor cell implantation, mice received 400 rads of whole body radiation. To establish tumors, $5\times10^6$ Raji cells resuspended in PBS were subcutaneously implanted on to the flank of each mouse.

In Vivo Therapeutic Study

NHL Raji tumors were allowed to grow until they reached a range of 100-200 mm³ and this was designated as day 0. Mice were then randomly separated into 5 treatment groups (n=6-8 per group). The first treatment group consisted of PBS as a control. The second and third groups consisted of the conventional formulation of VCR and DCM-VCR, both at a dose of 1 mg/kg. The fourth group consisted of DCM-VCR (1 mg/kg) plus N-acetylcysteine (NAC) at 100 mg/kg. NAC is a reducing agent and has been approved by FDA for mucolytic therapy (Mucomyst®) and the treatment of acetaminophen overdose. NAC was given intravenously 24 h after the administration of DCM-VCR. The fifth group consisted of DCM-VCR alone at a dose of 2.5 mg/kg. Treatments were administered on days 0 and 9 and were injected through the tail vein. Body weight and tumor volume were measured twice per week with tumor volume assessed using digital calipers and calculated using the equation: $(L \times W^2)/2$. Mice were sacrificed when tumor volume exceeded 1500 mm³ or 20 mm in either dimension.

Figure 19:
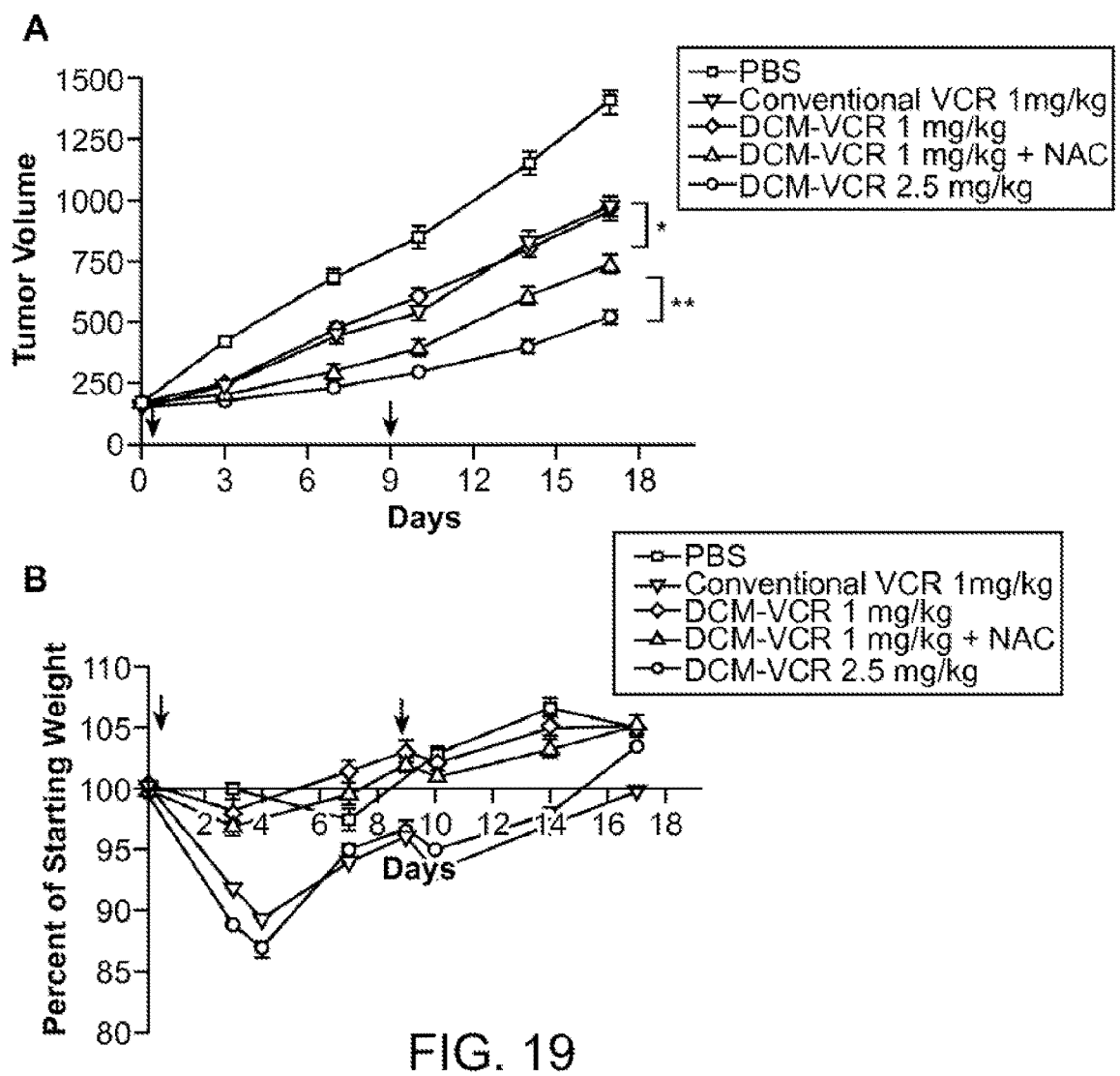
FIG. 19 shows in vivo anti-tumor efficacy (A) and body weight loss (B) of Raji tumor bearing nude mice treated with PBS, conventional VCR (1 mg/kg), DCM-VCR (1 mg/kg) plus or minus 100 mg/kg NAC or DCM-VCR (2.5 mg/kg). Arrows indicate the days when mice were treated. *, p<0.05; **, p<0.005.

All VCR treatments caused a (p<0.05) reduction in tumor growth as compared to the PBS control. Mice receiving 1 mg/kg DCM-VCR did not exhibit a superior anti-tumor effect compared with conventional VCR at the same dose. However, mice receiving 1 mg/kg DCM-VCR followed by 100 mg/kg NAC 24 h later, did exhibit a greater reduction in tumor volume compared with conventional VCR at the same dose (p<0.05). We attribute the greater efficacy to the on-demand drug release from DCM-VCR once it accumulated at the tumor site. Although 1 mg/kg conventional VCR and DCM-VCR without NAC exhibited equivalent efficacy, the group of mice receiving DCM-VCR (with and without NAC) lost significantly less weight than the group of mice receiving conventional VCR (FIG. 19B). In terms of a clinical benefit, DCM-VCR may offer a less toxic treatment option that does not sacrifice efficacy. The greatest reduction in tumor volume was observed in the group receiving 2.5 mg/kg DCM-VCR which exhibited a significantly greater tumor reduction than all treatment groups (p<0.005). It should be noted that the 2.5 mg/kg DCM-VCR treatment group lost an equivalent amount of weight as the 1 mg/kg conventional VCR group (FIG. 19B).

TABLE 3

Eight days after the final treatment, the blood of mice (n = 3) from each group was collected for determination of complete blood count.

|  | WBC (K/uL) | RBC (M/uL) | Hemoglobin (g/dL) | Platelets (K/uL) |
|---|---|---|---|---|
| PBS | 7.26 ± 2.31 | 10.17 ± 0.18 | 15.6 ± 0.24 | 695.3 ± 144.2 |
| Conventional VCR 1 mg/kg | 5.69 ± 1.51 | 9.58 ± 0.80 | 15.2 ± 0.60 | 971 ± 103.3 |
| DCM-VCR 1 mg/kg | 5.65 ± 1.60 | 9.30 ± 0.43 | 14.8 ± 0.51 | 876 ± 162.4 |
| DCM-VCR 1 mg/kg + N-Ac 100 mg/kg | 7.01 ± 1.67 | 9.98 ± 0.95 | 15.5 ± 1.25 | 811.7 ± 232.2 |
| DCM-VCR 2.5 mg/kg | 6.45 ± 1.22 | 8.95 ± 0.43 | 14.8 ± 0.81 | 1268 ± 206.9 |

TABLE 4

Eight days after the final treatment, the blood of mice (n = 3) from the PBS, conventional VCR 1 mg/kg and DCM-VCR 2.5 mg/kg groups was collected for serum chemistry analysis including alanine aminotransferase (ALT), aspartate aminotransferase (AST), total bilirubin, blood urea nitrogen (BUN) and creatinine.

|  | ALT (K/uL) | AST (M/uL) | BUN (K/uL) | Creatinine (K/uL) | Total Bilirubin (g/dL) |
|---|---|---|---|---|---|
| PBS | 38.5 ± 3.35 | 109.4 ± 6.5 | 25.7 ± 2.6 | .149 ± .01 | .128 ± .006 |
| Conventional VCR 1 mg/kg | 33.6 ± 1.06 | 101.1 ± 19.6 | 32.2 ± 3.8 | .202 ± .02 | .12 ± .017 |
| DCM-VCR 2.5 mg/kg | 31.9 ± 6.92 | 91 ± 7.8 | 33.1 ± 2.9 | .174 ± .02 | .089 ± .008 |

Figure 20:
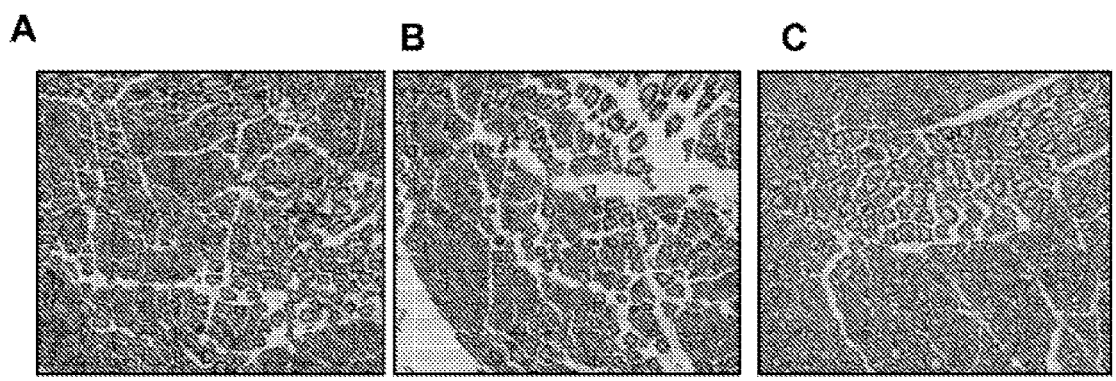
FIG. 20 shows mice (n=3) from the PBS (A), conventional VCR 1 mg/kg (B) and DCM-VCR 2.5 mg/kg (C) groups were sacrificed 8 days after the final treatment and the sciatic nerve was dissected. The nerves were processed into epoxy blocks and 500 nm sections were cut, collected onto slides and stained with Methylene Blue and Azur B stain.
Figure 21:
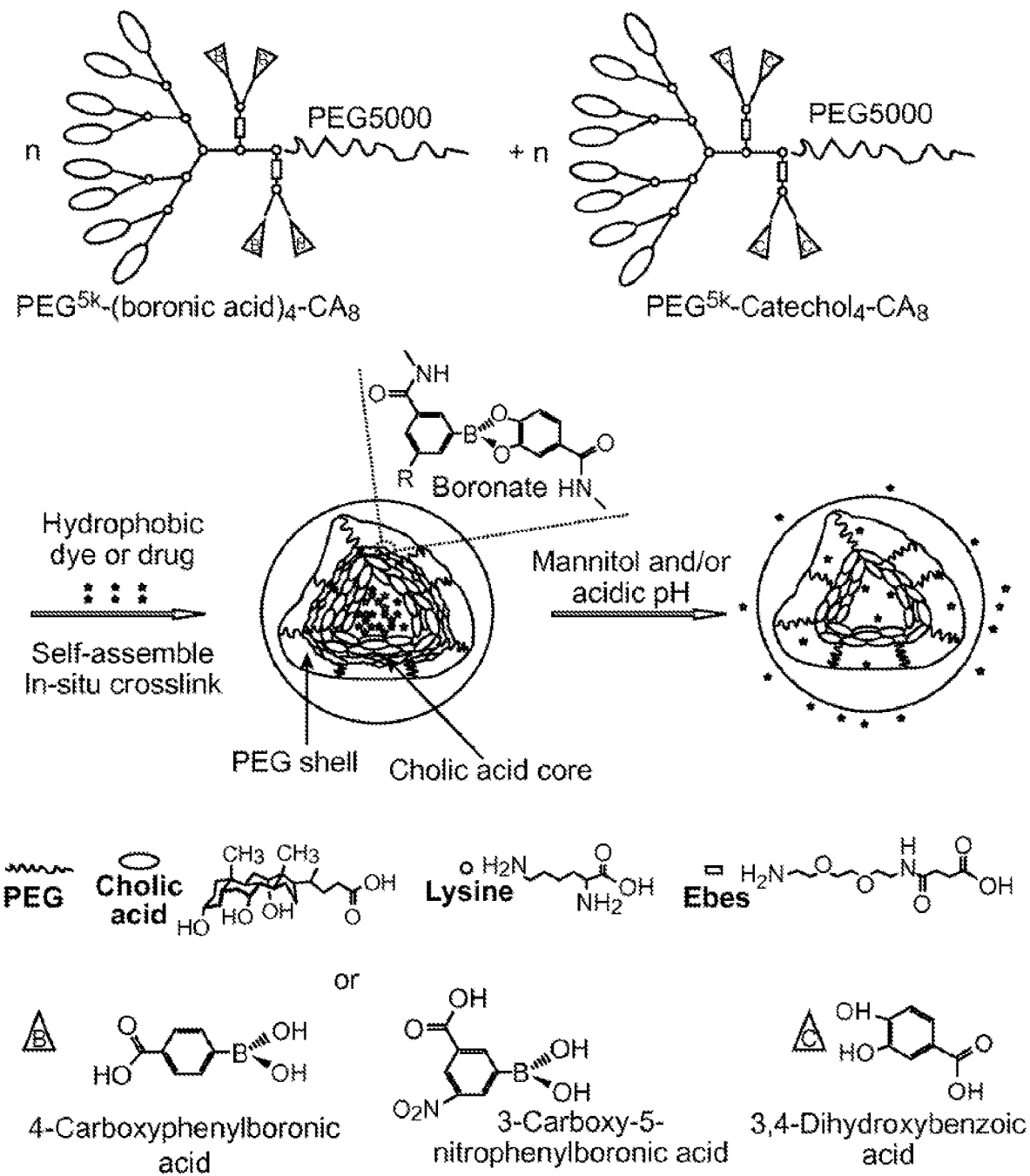
FIG. 21 shows a schematic representation of the telodendrimer pair [PEG$^{5k}$-(boronic acid/catechol)$_4$-CA$_8$] and the resulting boronate crosslinked micelles (BCM) in response to mannitol and/or acidic pH.

Eight days after the final treatment we dissected the sciatic nerve from mice of the PBS, conventional VCR (1 mg/kg) and DCM-VCR (2.5 mg/kg) groups to assess the acute eurotoxic effects of VCR by histological analysis. VCR is known to cause axonal degeneration and demyelination of nerve fibers which can be observed with either light or electron microscopy. Histological analysis revealed no obvious damage to the nerve fibers from the groups treated with conventional VCR (1 mg/kg) and DCM-VCR (2.5 mg/kg) and no differences compared to the PBS control group (FIG. 20).

Maximum Tolerated Dose

The maximum tolerated dose of the conventional formulation of VCR and DCM-VCR was investigated in healthy female balb/c mice. Mice (n=4) were treated with the conventional formulation of VCR or DCM-VCR at doses of 1.5, 2.5, 3.5 and 4.5 mg VCR/kg. VCR was administered through the tail vein every 10 days for a total of two treatments. Body weight and other symptoms of toxicity (unkempt fur, ataxia, piloerection, hind limb paralysis) were observed daily for 20 days. The MTD was defined as the allowance of a median body weight loss of 20% and causes neither death due to toxic effects nor remarkable changes in the general signs within 2 weeks after administration.

Mice treated with 1.5 mg/kg of conventional VCR had significant weight loss (18%). After day 4, these mice started to regain weight and reached their initial weight on day 10. The mice treated with doses higher than 1.5 mg/kg of conventional VCR lost >20% of their initial weight and were sacrificed. The MTD of conventional VCR determined in this study was similar to the MTD observed previously by other groups. Mice treated with the same doses of VCR in the form of DCM-VCR exhibited significantly less weight loss at all doses. Only the group of mice receiving the highest dose of 4.5 mg/kg DCM-VCR lost >20% of their initial weight and were sacrificed. Thus, DCM-VCR was able to increase the MTD of VCR from 1.5 to 3.5 mg/kg (>2-fold). Dose intensification of VCR in a clinical setting is significant as it may allow patients to receive a full dose of chemotherapy without the limiting toxicities.

Toxicity

Mice from the above mentioned therapeutic study were also used to investigate VCR hematologic and neurotoxicity. Eight days after the final treatment, the blood of mice (n=3) from each group was collected for determination of complete blood count as well as analysis of serum chemistry including alanine aminotransferase (ALT), aspartate aminotransferase (AST), total bilirubin, blood urea nitrogen (BUN) and creatinine. To compare the neurotoxic effects of the vincristine formulations, mice (n=3) were sacrificed eight days after the final treatment and the sciatic nerve was carefully dissected from the proximal aspect of the thigh to the knee joint proximal to its point of division into common peroneal, tibial, and sural nerves. The nerves were processed into epoxy blocks and 500 nm sections were cut, collected onto slides and stained with Methylene Blue and Azure B stain. Sections were imaged on an Olympus BH-2 microscope and images acquired using a Spot Insight digital camera (Diagnostic Instruments, Inc.).

Example 10. Preparation of Catechol Modified Conjugates (PEG$^{5k}$-Catechol$_2$-CA$_8$ and PEG$^{5k}$-Catechol$_4$-CA$_8$)

The telodendrimers containing two and four 3,4-Dihydroxybenzoic acids (named as PEG$^{5k}$-Catechol$_2$-CA$_8$ and PEG$^{5k}$-Catechol$_4$-CA$_8$, respectively) were synthesized via solution-phase condensation reactions from MeO-PEG-NH$_2$ via stepwise peptide chemistry. The typical procedure for synthesis of PEG$^{5k}$-Catechol$_2$-CA$_8$ and PEG$^{5k}$-Catechol$_4$-CA$_8$ was as follows: (Fmoc)Lys(Boc)-OH (3 eq.) was coupled onto the N terminus of PEG using DIC and HOBt as coupling reagents until a negative Kaiser test result was obtained, thereby indicating completion of the coupling reaction. PEGylated molecules were precipitated by adding cold ether and then washed with cold ether twice. Fmoc groups were removed by the treatment with 20% (v/v) 4-methylpiperidine in dimethylformamide (DMF), and the PEGylated molecules were precipitated and washed three times by cold ether. White powder precipitate was dried under vacuum and one coupling of (Fmoc)Lys(Boc)-OH and three couplings of (Fmoc)lys(Fmoc)-OH were carried out respectively to generate a third generation of dendritic polylysine terminated with eight Fmoc groups on one end of PEG. Cholic acid NHS ester were then coupled to the terminal end of dendritic polylysine. (Fmoc)Ebes-COOH was coupled to the amino groups of the proximal lysines between PEG and cholic acid upon the removal of Boc groups with 50% (v/v) trifluoroacetic acid (TFA) in dichloromethane (DCM). After the removal of Fmoc groups, one part of the polymer was coupled with 3,4-Dihydroxybenzoic acid resulting in $PEG^{5k}$-$L_2$-$Catechol_2$-$CA_8$ telodendrimer (Scheme S-1). The other part of the polymer was coupled with (Fmoc)lys(Fmoc)-OH and 3,4-Dihydroxybenzoic acid subsequently to generate $PEG^{5k}$-$Catechol_4$-$CA_8$ telodendrimer (Scheme S-1).

In order to prepare Rhodamine B labeled telodendrimers, (Fmoc)Lys(Dde)-OH was coupled to MeO-PEG-$NH_2$ initially to introduce an 1-(4,4-dimethyl-2,6-dioxocyclohex-1-yldine)ethyl (Dde) protected amino group. Rhodamine B isothiocyanate was conjugated to the amino group of the proximal lysine between PEG and cholic acids in the final telodendrimers after the removal of Dde protecting group by 2% (v/v) hydrazine in DMF.

Example 11. Preparation of 4-Carboxyphenyl Boronic Acid Modified Conjugates ($PEG^{5k}$-$BA_2$-$CA_8$ and $PEG^{5k}$-$BA_4$-$CA_8$) and 3-Carboxy-5-Nitrophenyl Boronic Acid Modified Conjugates ($PEG^{5k}$-$NBA_2$-$CA_8$ and $PEG^{5k}$-$NBA_4$-$CA_8$)

The telodendrimers containing two or four 4-Carboxyphenylboronic acid and 3-Carboxy-5-nitrophenylboronic acids (named as $PEG^{5k}$-$BA_2$-$CA_8$, $PEG^{5k}$-$BA_4$-$CA_8$, $PEG^{5k}$-$NBA_2$-$CA_8$ and $PEG^{5k}$-$NBA_4$-$CA_8$, respectively) were synthesized via the similar strategy as described above. 4-Carboxyphenylboronic acid pinacol ester and 3-Carboxy-5-nitrophenylboronic acid pinacol ester were coupled to the Ebes linkers or lysines between PEG and cholic acids at the last step. The four kinds of boronic acid containing telodendrimers were generated upon the removal of the pinacol esters with 50% (v/v) TFA in DCM. The telodendrimers was recovered from the mixture by three cycles of dissolution/reprecipitation with DMF and ether, respectively. Finally, the telodendrimers were dissolved in acetonitrile/water and lyophilized. The $PEG^{5k}$-$CA_8$ parent telodendrimer was synthesized to prepare the non-cross-linked micelles according to our previously reported method.

Example 12. Preparation of Boronate Cross-Linked Micelles

Two distinct boronic acid-containing telodendrimer and catechol-containing telodendrimer (total 20 mg) were first dissolved in anhydrous chloroform in a 10 mL round bottom flask. The chloroform was evaporated under vacuum to form a thin film. PBS buffer (1 mL) was added to re-hydrate the thin film, followed by 30 min of sonication. Boronate ester bonds formed between boronic acids and catechols of adjacent telodendrimers, upon self-assembly in PBS, resulted in the formation of boronate cross-linked micelles (BCM). The micelle solution was filtered with 0.22 μm filter to sterilize the sample.

Example 13. Preparation of Drug Loaded Boronate Cross-Linked Micelles

Hydrophobic anti-cancer drug, such as paclitaxel (PTX), doxorubicin (DOX) and vincristine (VCR), were loaded into the micelles by the solvent evaporation method as described in our previous studies. Briefly, drug (2.0 mg) and telodendrimers (total 20 mg) were first dissolved in anhydrous chloroform in a 10 mL round bottom flask. The chloroform was evaporated under vacuum to form a thin film. PBS buffer (1 mL) was added to re-hydrate the thin film, followed by 30 min of sonication. The unloaded PTX was removed by running the micelle solutions through centrifugal filter devices (MWCO: 3.5 kDa, Microcon®). The PTX loaded micelles on the filters were recovered with PBS. The amount of drug loaded in the micelles was analyzed on a HPLC system (Waters) after releasing the drugs from the micelles by adding 9 times of acetonitrile and 10 min sonication. The drug loading was calculated according to the calibration curve between the HPLC area values and concentrations of drug standard. The loading efficiency is defined as the ratio of drug loaded into micelles to the initial drug content. Hydrophobic dye (DiO or DiD) was loaded into the micelles using the same strategy. The amount of dye loaded in the micelles was analyzed on a fluorescence spectrometry (SpectraMax M2, Molecular Devices, USA) after releasing the drugs from the micelles by adding 9 times of acetonitrile and 10 min sonication. The dye loading was calculated according to the calibration curve between the fluorescence intensity and concentrations of dye standard in acetonitrile.

Example 14. Characterization of Drug Loaded Boronate Cross-Linked Micelles

General Characterization

The size and size distribution of the micelles were measured by dynamic light scattering (DLS) instruments (Microtrac). The micelle concentrations were kept at 1.0 mg/mL for DLS measurements. All measurements were performed at 25° C., and data were analyzed by Microtrac FLEX Software 10.5.3. The morphology of micelles was observed on a Philips CM-120 transmission electron microscope (TEM). The aqueous micelle solution (1.0 mg/mL) was deposited onto copper grids, stained with phosphotungstic acid, and measured at room temperature. The apparent critical micelle concentration (CMC) of the NCM and BCMs was measured through fluorescence spectra by using pyrene as a hydrophobic fluorescent probe as described previously. Briefly, micelles were serially diluted in PBS to give the concentrations ranging from $5 \times 10^{-7}$ to $5 \times 10^{-4}$ M. The stock solution of pyrene in methanol was added into the micelle solution to make a final concentration of pyrene of $2 \times 10^{-6}$ M. The solution was mildly shaken over night. Excitation spectra were recorded ranging from 300 to 360 nm with a fixed emission at 390 nm. The ratios of the intensity at 337 to 332 nm from the excitation spectra of pyrene were plotted against the concentration of the micelles. The CMC was determined from the threshold concentration, where the intensity ratio I337/I332 begins to increase markedly.

TABLE 5

Characterization of boronate cross-linked micelles and non-cross-linked micelles.

| Micelle Formulation | Telodendrimer pair | Size (nm)[a] | CMC (μg/mL)[b] | Stability In SDS[c] | PTX Content[d] |
|---|---|---|---|---|---|
| BCM1 | PEG$^{5k}$-BA$_2$-CA$_8$, PEG$^{5k}$-Catechol$_2$-CA$_8$ | 23 ± 4 | 10.5 | 2 min | 9.9% |
| BCM2 | PEG$^{5k}$-NBA$_2$-CA$_8$, PEG$^{5k}$-Catechol$_2$-CA$_8$ | 26 ± 6 | 8.7 | 30 min | 9.8% |
| BCM3 | PEG$^{5k}$-BA$_4$-CA$_8$, PEG$^{5k}$-Catechol$_4$-CA$_8$ | 22 ± 3 | 7.4 | 5 min | 9.9% |
| BCM4 | PEG$^{5k}$-NBA$_4$-CA$_8$, PEG$^{5k}$-Catechol$_4$-CA$_8$ | 27 ± 5 | 4.2 | Long term | 9.9% |
| NCM | PEG$^{5k}$-CA$_8$ | 22 ± 6 | 50.1 | <10 sec | 10.0% |

[a]Measured by dynamic light scattering (DLS).
[b]Measured via fluorescent method by using pyrene as a probe.
[c]The total period of time that the micelles retained their sizes in SDS, continuously measured by DLS every 10 sec at pH 7.4.
[d]PTX loading content of micelles (drug/polymer, w/w), in the presence of 20 mg/mL of total telodendrimers and 2.0 mg/mL PTX initial loading, measured by HPLC.

TABLE 6

Characterization of the telodendrimers.

| Telodendrimers | Mw (theo.)[a] | Mw (MS)[b] | $N_{CA}$[c] (NMR) | $N_{BA}$[e] (NMR) | $N_{NBA}$[f] (NMR) | $N_{catechol}$[d] (NMR) | $N_{BA}$[g] (ARS assay) | $N_{NBA}$[h] (ARS assay) |
|---|---|---|---|---|---|---|---|---|
| PEG$^{5k}$-CA$_8$ | 9059 | 8918 | 7.5 | — | — | — | — | — |
| PEG$^{5k}$-Catechol$_2$-CA$_8$ | 9893 | 9928 | 8.1 | — | — | 2.1 | — | — |
| PEG$^{5k}$-Catechol$_4$-CA$_8$ | 10419 | 10376 | 7.6 | — | — | 4.1 | — | — |
| PEG$^{5k}$-BA$_2$-CA$_8$ | 9917 | 9801 | 7.6 | 1.7 | — | — | 2.5 | — |
| PEG$^{5k}$-BA$_4$-CA$_8$ | 10467 | 10393 | 7.6 | 3.8 | — | — | 4.2 | — |
| PEG$^{5k}$-NBA$_2$-CA$_8$ | 9971 | 9837 | 7.7 | — | 1.8 | — | — | 2.3 |
| PEG$^{5k}$-NBA$_4$-CA$_8$ | 10650 | 10278 | 7.5 | — | 4.0 | — | — | 4.1 |

[a]Theoretical molecular weight.
[b]Obtained via MALDI-TOF MS analysis (linear mode). The boronic acid containing telodendrimers were measured in the pinacol ester form and the molecular weight was calculated as described above.
[c]Number of cholic acids, calculated based on the average integration ratio of the peaks of methyl proton 18, 19, and 21 in cholic acid at 0.66, 0.87 and 1.01 ppm and methylene proton of PEG at 3.5-3.7 ppm in $^1$H-NMR spectra in DMSO-d6 (90° pulse) The molecular weight of the starting PEG was 4912.
[e]Number of phenylboronic acids, calculated based on the average integration ratio of the peaks of the phenyl protons of phenylboronic acids (6.7-7.2 ppm) and methylene proton of PEG to in $^1$H-NMR spectra in DMSO-d6 (90° pulse).
[f]Number of nitro-phenylboronic acids, calculated based on the average integration ratio of the peaks of the phenyl protons of nitro-phenylboronic acids (8.6-8.9 ppm) and methylene proton of PEG to in $^1$H-NMR spectra in DMSO-d6 (90° pulse).
[d]Number of 3,4-Dihydroxybenzoic acids (catechols), calculated based on the average integration ratio of the peaks of the phenyl protons of catechols (6.7-7.5 ppm) and methylene proton of PEG to in $^1$H-NMR spectra in DMSO-d6 (90° pulse).
[g]Number of phenylboronic acids, determined by ARS colorimetric assay.
[h]Number of nitro-phenylboronic acids, determined by ARS colorimetric assay.

ARS Based Colorimetric and Fluorescence Assay

ARS is a catechol dye displaying dramatic changes in color and fluorescence intensity upon binding to boronic acid. In this study, we utilized ARS indicator based colorimetric assay to estimate the concentration of boronic acid on telodendrimers. Briefly, as the concentration of boronic acid is increased, a visible color change from burgundy to yellow was observed. The color and absorbance changes of ARS were observed with adding 3-Carboxy-5-nitrophenylboronic acid. The absorbance of the free ARS at 520 nm decreases as boronic acids added, and a new absorbance at 460 nm appears. A calibration curve was prepared by plotting the absorbance changes at 460 urn (AA) as function of concentrations of 4-Carboxyphenylboronic acid ([BA]) and 3-Carboxy-5-nitrophenylboronic acid ([NBA]). Based on the calibration curve, the number of boronic acids on the telodendrimers was calculated from the absorbance of samples in the colorimetric assay (Table 6).

ARS also displays a dramatic change in fluorescence intensity in response to the binding of boronic acids. Boronic acid containing telodendrimers solutions (boronic acid concentrations: 0-5 mM) were mixed ARS solution in PBS at pH 7.4 and the fluorescence signal of the mixtures was measured by fluorescence spectrometry (Nanodrop3000, Microtrac). The final concentration of ARS was fixed at 0.1 mM. ARS fluorescence assay was further used to characterize the binding between the boronic acid containing telodendrimers and catechol containing telodendrimers. In this experiment, the final concentration of ARS and boronic acid of boronic acid containing telodendrimers were fixed at 0.1 mM. Different molar ratio of catechol containing telodendrimers was premixed with boronic acid containing telodendrimers (0.1 mM) in anhydrous chloroform. The chloroform was evaporated and the thin film on the inner surface of flask was re-hydrated with PBS buffer to generate boronate cross-linked micelles. ARS solution was then mixed with the above micelle solutions and the fluorescence signal of the mixtures was measured by fluorescence spectrometry (Nanodrop3000, Microtrac).

Figure 22:
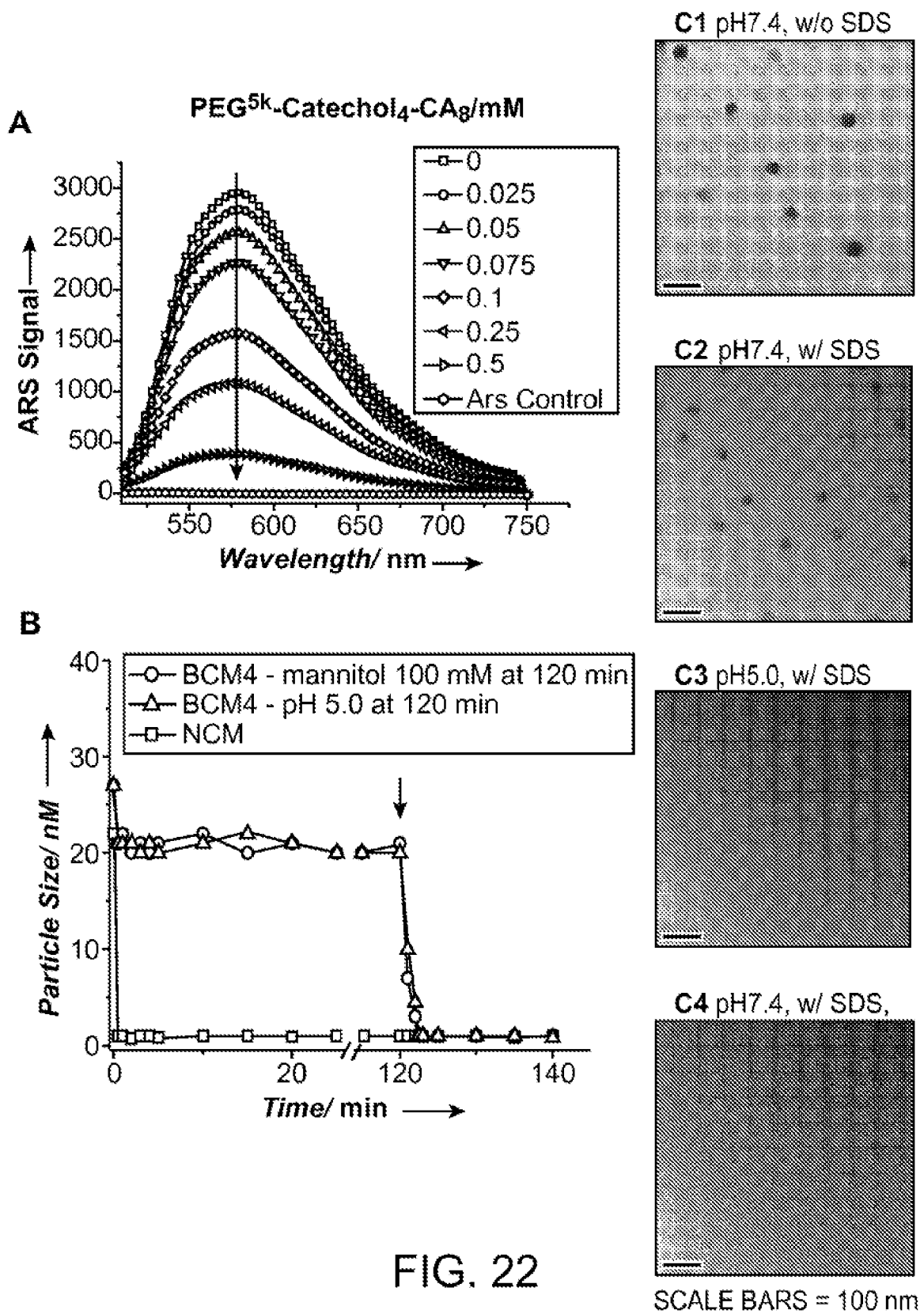
FIG. 22 shows (A) the fluorescent intensity of ARS (0.1 mM) upon mixing with micelles formed by PEG$^{5k}$-NBA$_4$-

When the concentrations of ARS and boronic acid containing telodendrimers were fixed at 0.1 mM, the fluorescence of ARS was dramatically suppressed with increasing amounts of PEG$^{5k}$-Catechol$_4$-CA$_8$ (0 to 0.5 mM) (FIG. 22). These results are a qualitative indication of the formation of catechol-boronate crosslinking esters as ARS was prevented from complexation with boronic acid containing telodendrimers.

Stability

The stability study was performed to monitor the change in particle size of the NCM and BCMs in the presence of sodium dodecyl sulfate (SDS), which was reported to be able to efficiently break down polymeric micelles. An SDS solution (7.5 mg/mL) was added to aqueous solutions of micelles (1.5 mg/mL). The final SDS concentration was 2.5 mg/mL and the micelle concentration was kept at 1.0 mg/mL. The size and size distribution of the micelle solutions was monitored continuously via dynamic light scattering (DLS) instruments (Microtrac) for 2 days. The stability of the micelles was also evaluated in PBS at different pH levels or in presence of mannitol and glucose (0, 10 mM, 50 mM, and 100 mM), together with SDS. Hydrogen chloride and sodium hydroxide solutions were used to prepare PBS at different pH levels. The pH values of the buffer were determined by a digital pH meter (0350 pH/Temp/mV meter, Beckman Coulter, USA) which gave pH values within 0.01 units. During the stability study, a small portion of the samples were taken out and further observed under TEM. The stability of NCM and BCMs was further studied in 50% (v/v) plasma from healthy human volunteers. The mixture was incubated at physiological body temperature (37° C.) followed by size measurements at predetermined time intervals up to 96 h.

The rapid disappearance (<10 sec) of the particle size signal for the NCM reflects the loss of integrity (FIGS. 30A & C). The BCM1, BCM2 and BCM3 retained the size in SDS for 2 min, 5 min and 30 min, respectively (Table 5). Despite an initial decrease, the constant particle size was observed over 2 days for BCM4 treated under the same conditions indicating that the cross-linked micelles self-assembled from the telodendrimer pair of PEG$^{5k}$-NBA$_4$-CA$_8$ and PEG$^{5k}$-Catechol$_4$-CA$_8$ remained intact (FIG. 22B, FIG. 30). BCM3 and BCM4, containing double the number of boronate esters retained their structural integrity significantly longer in the presence of SDS, when compared to BCM1 and BCM2, respectively. BCM2 and BCM4 crosslinked via nitro phenyl boronate esters were more stable than the corresponding phenyl boronate esters crosslinked micelles BCM1 and BCM3.

We further investigated the response to pH- and diol- for BCM4 in the presence of SDS. The particle size signal of BCM4 decreased suddenly (within 2 min) in SDS after 120 min incubation in pH 5.0, indicating that the micelle rapidly dissociated when a critical percentage of boronate bonds were hydrolyzed (FIG. 22B, FIG. 30G). We found that mannitol (containing three cis-diol pairs) could also efficiently cleave the crosslinking boronate bonds of the BCM4, as evidenced by the rapid reduction in particle size of BCM4 in the presence of SDS and excess of mannitol (100 mM) (FIG. 22A, FIG. 30H). On the contrary, the size of BCM4 persisted in the presence of both SDS and 100 mM glucose (containing one cis-diol) (FIG. 30I). TEM permitted the confirmation that the micellar structure of NCM was disrupted in SDS solution. The TEM graphs also demonstrated the micellar structure of BCM4 was well retained in SDS at pH 7.4 (FIG. 22C2) but was rapidly disrupted in SDS at pH 5.0 or in the presence of 100 mM mannitol (FIG. 22C3, C4).

Cell Uptake and MTT Assay

SKOV-3 ovarian cancer cells were seeded at a density of 50000 cells per well in eight-well tissue culture chamber slides (BD Biosciences, Bedford, Mass., USA), followed by 24 h of incubation in McCoy's 5a Medium containing 10% FBS. The medium was replaced, and DiD labeled micelles (100 μg/mL) were added to each well. After 30 min, 1 h, 2 h and 3 h, the cells were washed three times with PBS, fixed with 4% paraformaldehyde and the cell nuclei were stained with DAPI. The slides were mounted with cover slips and observed under confocal laser scanning microscope (Olympus, FV1000). For the DiD channel, the excitation was set to 625 nm while the emission was set to 700 nm.

SKOV-3 ovarian cancer cells were seeded in 96-well plates at a density of 5000 cells/well 24 h prior to the treatment. The culture medium was replaced with fresh medium containing various formulations of PTX with different dilutions at pH 7.4 or 5.0, in the absence or in the presence of 100 mM mannitol. The cells were washed with PBS and incubated for another 23 h in a humidified 37° C., 5% CO$_2$ incubator. MIT was added to each well and further incubated for 4 h. The absorbance at 570 nm and 660 nm was detected using a micro-plate ELISA reader (SpectraMax M2, Molecular Devices, USA). Untreated cells served as a control. Results were shown as the average cell viability [(OD$_{treat}$−OD$_{blank}$)/(OD$_{control}$−OD$_{blank}$)×100%] of triplicate wells. The cells were also treated with telodendrimers and empty crosslinked micelles with different dilutions and incubated for total 72 h in order to evaluate telodendrimer related toxicity.

PTX-NCM showed comparable in vitro anti-tumor effects against SKOV-3 cells as Taxol® (free drug of paclitaxel). PTX-BCM4 was found to be considerably less cytotoxic than Taxol® and PTX-NCM at equal dose levels. There were minimal changes in the toxicity profile of PTX-NCM and free drug triggered with acidic pH and mannitol. PTX-BCM4 showed significantly enhanced cancer cell inhibition at pH 5.0 in the presence of mannitol (100 mM).

In Vivo Blood Elimination Kinetics and Biodistribution

Rhodamine B labeled NCM and BCMs were prepared for the blood elimination study. The concentration of rhodamine B conjugated micelles was 2.0 mg/mL. The absorbance and fluorescence spectra of these micelles diluted 20 times by PBS were characterized by fluorescence spectrometry (SpectraMax M2, Molecular Devices, USA). 100 μL of Rhodamine B conjugated NCM and BCMs were injected into tumor free nude mice via tail vein. 50 μL blood was collected at different time points post-injection to measure the fluorescence signal of Rhodamine B.

After intravenous injection into mice, rhodamine B signal of NCM was rapidly eliminated from blood circulation and fell into the background level within 10 hr post injection (FIG. 24F). Rhodamine B signal of BCM4 in blood was 6 times higher than that of NCM at 10 hr post injection and sustained for more than 24 hr.

In Vivo Toxicity

PTX loaded NCM have been safely applied for in vivo cancer treatment. The single treatment MTD in mice was observed to be 75 mg PTX/kg, the corresponding telodendrimer dosage was 200 mg/kg. However, without the encapsulation of hydrophobic PTX inside NCM to keep the telodendrimers together, the micelles tend to be more dynamic and dissociate more easily upon dilution, which may cause hemolytic side-effect. In order to investigate for telodendrimer related toxicity in vivo, both empty non-cross-linked and cross-linked micelles were injected in tumor free nude mice at the single dose of 200 mg/kg via tail vein. PBS was injected into the mice as a control. Mice were checked for possible signs of toxicity and the survival situation was monitored daily for two weeks. At day 7 after injection, blood samples were obtained from all the mice for the measurement of blood cell counts, serum chemistry including alanine aminotransferase (ALT), aspartate aminotransferase (AST) and blood urea nitrogen (BUN).

Example 15. Release of Drug from Boronate Cross-Linked Micelle

PTX-loaded NCM and BCMs was prepared to determine the in vitro release profile. The PTX loading for NCM, BCM1, BCM2, BCM3 and BCM4 were 9.9%, 9.8%, 9.8%, 9.9%, 10.0% (w/w, PTX/micelle) in the presence of total 20 mg telodendemers measured. Aliquots of PTX-loaded micelle solution were injected into dialysis cartridges (Pierce Chemical Inc.) with a 3.5 kDa MWCO. In order to make an ideal sink condition, 10 g charcoal was added in the release medium. The cartridges were dialyzed against PBS at different pH levels (pH6.5, pH6.0, pH 5.5 and pH5.0) or in the presence of various concentrations of glucose or mannitol (0, 10 mM, 50 mM, and 100 mM) at 37° C. The release medium was stirred at a speed of 100 rpm. The concentration of PTX remaining in the dialysis cartridge at various time points was measured by HPLC. In some experiments, the release medium (pH7.4) was replaced with fresh medium at different pH levels (pH6.5, pH6.0, pH5.5 and pH5.0) and/or in the presence of mannitol or glucose (10 and 100 mM) at a specific release time (5 h). Values were reported as the means for each duplicate samples.

PTX release from NCM was rapid with almost 30% of PTX released within the first 9 h independently from the pH of the release medium or the presence of diols. PTX release from BCM3 crosslinked via phenyl boronate was significantly slower than NCM but faster than BCM4 with nitrophenyl boronate crosslinking at pH 7.4. PTX release from BCM3 was promoted when decreasing the pH of the medium from 7.4 to 6.5 while that of BCM4 was accelerated at pH 5.5. In the presence of glucose at its physiological level (2-10 mM) or even higher concentration (50 mM), PTX release from BCM3 and BCM4 was similar to that in the release media without glucose. It was noted that PTX release was not sensitive to 10 mM mannitol but could be gradually facilitated as the concentration of mannitol increased up to the range of 50-100 mM.

In order to simulate the in vivo situations, the PTX release from BCM4 was first incubated under psychological pH for a period of time (e.g. 5 hr) and then was triggered with acidic pH and/or mannitol. The PTX release from BCM4 was significantly slower than that from NCMs at the initial 5 h. When 100 mM mannitol was added or the pH of the medium was adjusted to 5.0 at the 5 hr time point, there was a burst of drug release from the BCM4. It should be noted that the PTX release can be further accelerated via the combination of 100 mM of mannitol and pH 5.0. This two-stage release strategy can be exploited so that premature drug release can be minimized during circulation in vivo followed by rapid drug release triggered by the acidic tumor microenvironment, or upon micelle exposure to the acidic compartments of cancer cells or by the additional administration of mannitol.

Example 16. Treatment of Asthma

To evaluate the therapeutic efficacy of micelle-encapsulated dexamethasone, we use an asthma mouse model that employs an ovalbumin (OVA) in alum (Ova/alum) sensitization and OVA aerosol exposure regimen. This mimics the pathological features of asthma in terms of T cell and eosinophil driven-inflammatory and mucous hypersecretory responses and exhibits the structural airway changes of chronic asthma (ref 1 & 2). This experiment was done in collaboration with Dr. Nick Kenyon of UC Davis. Dexamethasone was nanoformulated with $PEG^{5k}$-$CA^8$ and $PEG^{2k}$-$CA_4$. OVA exposed mice were treated with dexamethasone-loaded nanoparticles, dexamethasone alone, or PBS. Both dexamethasone nanoformulations decreased lung lavage cell counts and eosinophil counts more than Dex alone (FIG. 34).

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound having a structure selected from the group consisting of:

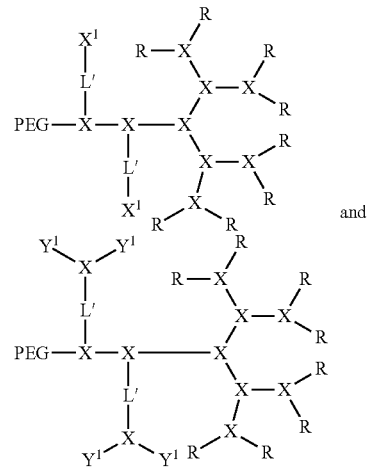

wherein
each branched monomer X is a lysine;
L' is a Ebes linker with the following formula:

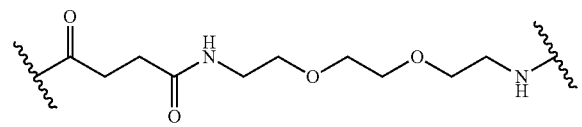 [SMILES: *NCCOCCOCCNC(=O)CCC(*)=O]

each PEG is a polyethyleneglycol (PEG) polymer, wherein each PEG polymer is PEG5k;
each R is cholic acid; and
each $Y^1$ is a crosslinking group selected from the group consisting of carboxyphenylboronic acid, carboxynitrophenyl boronic acid and 3,4-dihydroxybenzoic acid.

* * * * *